US012128055B2

(12) United States Patent
Birrell

(10) Patent No.: US 12,128,055 B2
(45) Date of Patent: Oct. 29, 2024

(54) PHARMACEUTICAL FORMULATIONS AND SYSTEMS FOR DELIVERY OF AN ANDROGENIC AGENT AND AN AROMATASE INHIBITOR WITH SUSTAINED MULTI-PHASIC RELEASE PROFILES AND METHODS OF USE

(71) Applicant: Havah Therapeutics Pty Ltd., Picadilly SA (AU)

(72) Inventor: Stephen Nigel Birrell, Picadilly (AU)

(73) Assignee: Havah Therapeutics Pty Ltd., North Adelaide (AU)

(*) Notice: Subject to any disclaimer, the term of this patent is extended or adjusted under 35 U.S.C. 154(b) by 269 days.

(21) Appl. No.: 17/661,215

(22) Filed: Apr. 28, 2022

(65) Prior Publication Data

US 2023/0088473 A1   Mar. 23, 2023

Related U.S. Application Data

(63) Continuation of application No. 17/437,525, filed as application No. PCT/AU2020/050562 on Jun. 3, 2020, now Pat. No. 11,524,014.

(30) Foreign Application Priority Data

Jun. 3, 2019   (AU) .............................. 2019901911

(51) Int. Cl.
*A61K 31/568*   (2006.01)
*A61K 9/00*   (2006.01)
(Continued)

(52) U.S. Cl.
CPC .......... *A61K 31/568* (2013.01); *A61K 9/0024* (2013.01); *A61K 31/4196* (2013.01); *A61P 37/02* (2018.01)

(58) Field of Classification Search
CPC .. A61K 31/568; A61K 9/0024; A61K 9/0019; A61K 31/4196; A61K 2300/00; A61P 37/02; A61P 5/24
See application file for complete search history.

(56) References Cited

U.S. PATENT DOCUMENTS

| 4,147,783 A | 4/1979 | van der Vies |
| 4,412,993 A | 11/1983 | Sokolowski |
(Continued)

FOREIGN PATENT DOCUMENTS

| WO | 1990010462 | 9/1990 |
| WO | 1994016709 | 8/1994 |
(Continued)

OTHER PUBLICATIONS

Glaser et al, Subcutaneous Testosterone Anastrozole Therapy in Men: Rationale, Dosing, and Levels on Therapy, International Journal of Pharmaceutical Compounding, vol. 23, No. 4. (Year: 2019).*

(Continued)

*Primary Examiner* — Carlos A Azpuru
(74) *Attorney, Agent, or Firm* — Cynthia Hathaway; Brock Levin

(57) ABSTRACT

The present disclosure is directed formulations, delivery systems and/or methods of use that have a novel a sustained release multi-phasic concentration pattern that may be used, among other things, for reducing mammographic breast density and/or breast stiffness in warm-blooded animals. For example, the formulation may comprise: the administration of an effective amount of androgenic agent and an effective amount of an aromatase inhibitor to a subject that provides a sustained release multi-phasic concentration pattern in the blood of the subject over time as measured by serum concentration for the androgen and plasma concentration for the aromatase inhibitor and improves, among other things, (Continued)

breast tissue stabilization and/or increases of the levels of androgen receptor expression. The present disclosure is also directed to the use of an effective amount of an androgenic agent in combination with an effective amount of an aromatase inhibitor for the prophylaxis or treatment of autoimmune inflammatory mastitis (AIM) in a patient in need thereof. Autoimmune inflammatory mastitis includes the conditions of idiopathic inflammatory macromastia, plasma cell mastitis, granulomatous mastitis.

23 Claims, 29 Drawing Sheets

(51) Int. Cl.
    *A61K 31/4196*      (2006.01)
    *A61P 37/02*      (2006.01)

(56) References Cited

U.S. PATENT DOCUMENTS

| | | | |
|---|---|---|---|
| 5,824,286 | A | 10/1998 | Hodgen |
| 5,861,387 | A | 1/1999 | Labrie |
| 6,200,593 | B1 | 3/2001 | Place |
| 6,241,529 | B1 | 6/2001 | Place |
| 6,569,896 | B2 | 5/2003 | Dalton |
| 6,593,313 | B2 | 7/2003 | Place |
| 6,696,432 | B1 | 2/2004 | Elliesen |
| 6,995,284 | B2 | 2/2006 | Dalton |
| 7,772,433 | B2 | 8/2010 | Dalton |
| 8,003,689 | B2 | 8/2011 | Veverka |
| 8,008,348 | B2 | 8/2011 | Steiner |
| 8,980,569 | B2 | 3/2015 | Weinberg |
| 8,980,840 | B2 | 3/2015 | Truitt, III |
| 9,150,501 | B2 | 10/2015 | Dalton |
| 9,168,302 | B2 * | 10/2015 | Birrell ..................... A61P 15/00 |
| 9,351,977 | B2 | 5/2016 | Birrell |
| 9,616,072 | B2 | 4/2017 | Birrell |
| 10,064,874 | B2 | 9/2018 | Birrell |
| 10,471,073 | B2 | 11/2019 | Birrell |
| 10,525,063 | B2 | 1/2020 | Birrell |
| 11,040,044 | B2 | 6/2021 | Birrell |
| 11,524,014 | B2 | 12/2022 | Birrell |
| 11,883,414 | B2 | 1/2024 | Birrell |
| 2003/0087885 | A1 | 5/2003 | Masini-Eteve |
| 2004/0191311 | A1 | 9/2004 | Liang |
| 2005/0032750 | A1 | 2/2005 | Steiner |
| 2005/0176692 | A1 | 8/2005 | Amory |
| 2005/0233970 | A1 | 10/2005 | Garnick |
| 2006/0069067 | A1 | 3/2006 | Bhatnagar |
| 2007/0066568 | A1 | 3/2007 | Dalton |
| 2008/0085874 | A1 | 4/2008 | Kushner |
| 2009/0264534 | A1 | 10/2009 | Dalton |
| 2010/0144687 | A1 | 6/2010 | Glaser |
| 2014/0018433 | A1 | 1/2014 | Dalton |
| 2014/0080905 | A1 | 3/2014 | Dalton |
| 2014/0162991 | A1 | 6/2014 | Glaser |
| 2022/0079954 | A1 | 3/2022 | Birrell |
| 2022/0088035 | A1 | 3/2022 | Birrell |

FOREIGN PATENT DOCUMENTS

| | | |
|---|---|---|
| WO | 2000069467 | 11/2000 |
| WO | 2001087334 | 11/2001 |
| WO | 2002009721 | 2/2002 |
| WO | 2002030355 | 4/2002 |
| WO | 2004034978 | 4/2004 |
| WO | 2004035739 | 4/2004 |
| WO | 2004064747 | 8/2004 |
| WO | 2005011705 | 2/2005 |
| WO | 2005037263 | 4/2005 |
| WO | 2005070434 | 8/2005 |
| WO | 2007045027 | 4/2007 |
| WO | 2008127717 | 10/2008 |
| WO | 2009036566 | 3/2009 |
| WO | 2010065358 | 6/2010 |
| WO | 2010118287 | 10/2010 |
| WO | 2013067170 | 5/2013 |
| WO | 2016061615 | 4/2016 |
| WO | 2017066827 | 4/2017 |
| WO | 2020243777 | 12/2020 |

OTHER PUBLICATIONS

Abu Hashim, H. et al., "Randomized Comparison of Superovulation with Letrozole vs. Clomiphene Citrate in an IUI Program for Women with Recently Surgically Treated Minimal to Mild Endometriosis", Acta. Obstet. Gynecol. Scand., 91(3):338-345, (2012).

Alexander, H. et al., "Proteomic Analysis to Identify Breast Cancer Biomarkers in Nipple Aspirate Fluid", Clin. Cancer Res., 10(22):7500-7510, (2004).

Arendt, L. et al., "Working Stiff: How Obesity Boosts Cancer Risk", Sci. Transl. Med., 7(301), 301fs34, 3 pages, (2015).

Ashbeck, E. et al., "Benign Breast Biopsy Diagnosis and Subsequent Risk of Breast Cancer", Cancer Epidemiol Biomarkers Prev., 16(3):467-472, (2007).

Baker, E. et al., "Cancer Cell Stiffness: Integrated Roles of Three-Dimensional Matrix Stiffness and Transforming Potential", Biophys J., 99(7):2048-57, (2010).

Beattie, M. et al., "Endogenous Sex Hormones, Breast Cancer Risk, and Tamoxifen Response: An Ancillary Study in the NSABP Breast Cancer Prevention Trial (P-1)", J. Natl. Cancer Inst., 98(2):110-115, (2006).

Beckmann, K. et al., "Impact of Hormone Replacement Therapy use on Mammographic Screening Outcomes", Cancer Causes Control, 24(7): 1417-1426, (2013).

Beer, B. et al., "Development and Validation of a Liquid Chromatography-Tandem Mass Spectrometry Method for the Simultaneous Quantification of Tamoxifen, Anastrozole, and Letrozole in Human Plasma and its Application to a Clinical Study", Anal. Bioanal. Chem., 398(4):1791-1800, (2010).

Bercoff, J., "ShareWave™ Elastography—White Paper" Super Sonic Imagine, S.A. copyright (2008).

Bhasin, S. et al., "Selective Androgen Receptor Modulators (SARMs) as Function Promoting Therapies", Curr. Opin. Clin. Nutr. Metab. Care, 12(3):232-240, (2009).

Birrell, S. et al., "Combined Hormone Replacement Therapy and Breast Cancer", Expert Report, 34 pages, dated Apr. 1, 2008.

Birrell, S. et al., "Disruption of Androgen Receptor Signaling by Synthetic Progestins May Increase Risk of Developing Breast Cancer", FASEB J., 21(10):2285-2293, (2007).

Bolduc, C. et al., "Transcriptomic Characterization of the Long-Term Dihydrotestosterone Effects in Adipose Tissue", Obesity, 15(5):1107-1132, (2007).

Boyd, N. et al., "Breast-Tissue Composition and Other Risk Factors for Breast Cancer in Young Women: A Cross-Sectional Study", Lancet Oncol., 10(6), 569-580, (2009).

Boyd, N. et al., "Evidence That Breast Tissue Stiffness Is Associated with Risk of Breast Cancer", PLoS One, 9(7):e100937, 8 pages, (2014).

Boyd, N. et al., "Mammographic Densities and Breast Cancer Risk", Breast Dis., 10(3,4):113-126, (1998).

Boyd, N. et al., "Mammographic Density, Response to Hormones, and Breast Cancer Risk", J. Clin. Oncol., 29(22):2985-2992, (2011).

Braunstein, G., "Safety of Testosterone Treatment in Postmenopausal Women", Fertil. Steril., 88(1):1-17, (2007).

Byrne, C. et al., "Mammographic Density Change With Estrogen and Progestin Therapy and Breast Cancer Risk", J. Natl. Cancer Inst., 109(9):djx001, 7 pages, (2017).

Chen, R. et al., "Antiproliferative Effects of Anastrozole on MCF-7 Human Breast Cancer Cells In Vitro are Significantly Enhanced by Combined Treatment with Testosterone Undecanoate", Mol. Med. Rep., 12(1):769-775, (2015).

(56) References Cited

OTHER PUBLICATIONS

Cheng, Q. et al., "Overexpression of CD36 in mammary fibroblasts suppresses colony growth in breast cancer cell lines", Biochem Biophys Res Commun., 526(1):41-7, (2020).

Chiu, S. et al., "Effect of Baseline Breast Density on Breast Cancer Incidence, Stage, Mortality, and Screening Parameters: 25-Year Follow-up of a Swedish Mammographic Screening", Cancer Epidemiol. Biomarkers Prev., 19(5):1219-1228, (2010).

Chlebowski, R. et al., "Influence of Estrogen Plus Progestin on Breast Cancer and Mammography in Healthy Postmenopausal Women: The Women's Health Initiative Randomized Trial", JAMA, 289(24):3243-3253, (2003).

Cilotti, A. et al., "Male Osteoporosis and Androgenic Therapy: From Testosterone to SARMs", Clin. Cases Miner. Bone Metab., 6(3):229-233, (2009).

Crandall, C. et al., "Breast Tenderness After Initiation of Conjugated Equine Estrogens and Mammographic Density Change", Breast Cancer Res. Treat., 131(3):969-979, (2012).

Cuzick, J. et al., "Impact of Preventive Therapy on the Risk of Breast Cancer Among Women with Benign Breast Disease", Breast, 24:S51-S55, (2015).

Cuzick, J. et al., "Tamoxifen-Induced Reduction in Mammographic Density and Breast Cancer Risk Reduction: A Nested Case-Control Study", J. Natl. Cancer Inst., 103(9):744-752, (2011).

D'Orsi, C. et al., "Breast Imaging Reporting and Data System", ACR BI-RADS® Atlas, Reston, VA: American College of Radiology, (2013).

Dalton, J. et al., "The Selective Androgen Receptor Modulator GTx-024 (Enobosarm) Improves Lean Body Mass and Physical Function in Healthy Elderly Men and Postmenopausal Women: Results of a Double-Blind, Placebo-Controlled Phase II Trial", J. Cachexia Sarcopenia Muscle, 2(3):153-161, (2011).

Das, L. et al., "Idiopathic gigantomastia: newer mechanistic insights implicating the paracrine milieu", Endocrine, 66(2):166-77, (2019).

Davis, S. et al., "The effect of transdermal testosterone on mammographic density in postmenopausal women not receiving systemic estrogen therapy", J Clin Endocrinol Metab., 94(12):4907-13, (2009).

Davis, S. et al., "Androgen Treatment of Postmenopausal Women", J. Steroid Biochem. Mol. Biol., 142:107-114, (2014).

Dawson, C. et al., "Tissue-resident ductal macrophages survey the mammary epithelium and facilitate tissue remodelling", Nat Cell Biol., 22(5):546-58, (2020).

Defilippis, R. et al., "CD36 Repression Activates a Multicellular Stromal Program Shared by High Mammographic Density and Tumor Tissues", Cancer Discov., 2(9):826-839, (2012).

Defilippis, R. et al., "Stress Signaling from Human Mammary Epithelial Cells Contributes to Phenotypes of Mammographic Density", Cancer Res., 74(18):5032-5044, (2014).

Dilley, W. et al., "Androgen Stimulation of Gross Cystic Disease Fluid Protein and Carcinoembryonic Antigen in Patients with Metastatic Breast Carcinoma", J. Natl. Cancer Inst., 70(1):69-74, (1983).

Dixon, JM et al., "Risk of Breast Cancer in Women with Palpable Breast Cysts: A Prospective Study", Lancet, 353:1742-1745, (1999).

Duhan, N. et al., "Role of the Aromatase Inhibitor Letrozole in the Management of Uterine Leiomyomas in Premenopausal Women", Eur. J. Obstet. Gynecol. Reprod. Biol., 171:329-332, (2013).

Eigeliene, N. et al., "Androgens Inhibit the Stimulatory Action of 17beta-Estradiol on Normal Human Breast Tissue in Explant Cultures", J. Clin. Endocrinol. Metab., 97(7), 12 pages, (2012).

European Patent No. 1945224; Extended European Search Report and Written Opinion, dated Aug. 24, 2009; 7 pages.

European Patent No. 3209301; Extended European Search Report and Written Opinion, dated Feb. 12, 2018; 8 pages.

Fabian, C. et al., "Reduction in proliferation with six months of letrozole in women on hormone replacement therapy", Breast Cancer Res Treat., 106(1):75-84, (2007).

Freer, P., "Mammographic Breast Density: Impact on Breast Cancer Risk and Implications for Screening", RadioGraphics, 35(2)302-315, (2015).

Gao, W. et al., "Expanding the Therapeutic use of Androgens via Selective Androgen Receptor Modulators (SARMs)", Drug Discov. Today, 12(5-6):241-248, (2007).

Gao, W. et al., "Ockham's Razor and Selective Androgen Receptor Modulators (SARMs): Are We Overlooking the Role of 5alpha-Reductase?", Mol. Interv., 7(1):10-13, (2007).

Gascard, P. et al., "Epigenetic and Transcriptional Determinants of the Human Breast", Nat. Commun., 6:6351, 10 pages (2015).

Gaubin, M. et al., "Potent Inhibition of CD4/TCR-Mediated T Cell Apoptosis by a CD4-Binding Glycoprotein Secreted from Breast Tumor and Seminal Vesicle Cells", J. Immunol., 162:2631-2638, (1999).

Ghajar, C., "A Stiffness-Mediated Oncogenic Hammer", Sci. Transl. Med., 6(237):237fs21, 3 pages, (2014).

Ghosh, S. et al., "Mechanical Phenotype is Important for Stromal Aromatase Expression", Steroids, 76(8):797-801, (2011).

Giess, C. et al., "Background Parenchymal Enhancement at Breast MR Imaging: Normal Patterns, Diagnostic Challenges, and Potential for False-Positive and False-Negative Interpretation", RadioGraphics, 34(1):234-247, (2014).

Gilliver, SC et al., "5alpha-Dihydrotestosterone (DHT) Retards Wound Closure by Inhibiting Re-Epithelialization", J. Pathol., 217:73-82, (2009).

Glaser, R. "Subcutaneous Testosterone-Anastrozole Implant Therapy in Breast Cancer Survivors", 2010 Breast Cancer Symposium, Abstract 221, Jan. 2010; 1 page.

Glaser, R. et al., "Beneficial Effects of Testosterone Therapy in Women Measured by the Validated Menopause Rating Scale {MRS)", Maturitas, 68(4):355-361, (2011).

Glaser, R. et al., "Rapid Response of Breast Cancer to Neoadjuvant Intramammary Testosterone-Anastrozole Therapy: Neoadjuvant Hormone Therapy in Breast Cancer", Menopause, 21(6):673-678, (2014).

Glaser, R. et al., "Reduced Breast Cancer Incidence in Women Treated with Subcutaneous Testosterone, or Testosterone with Anastrozole: A Perspective, Observational Study", Maturitas, 76:342-349, (2013).

Glaser, R. et al., "Subcutaneous Testosterone-Letrozole Therapy Before and Concurrent with Neoadjuvant Breast Chemotherapy: Clinical Response and Therapeutic Implications", Menopause: The Journal of The North American Menopause Society, 24(7):859-864, (2017).

Glaser, R. et al., "Subgroups of Patients Treated With An Aromatase Inhibitor (Anastrozole) Delivered Subcutaneously in Combination With Testosterone", Abstract, 9th European Congress on Menopause and Andropause, Maturitas, vol. 71, Supplement 1, Mar. 28, 2012; 1 page.

Glaser, R. et al., "Testosterone and Breast Cancer Prevention", Maturitas, 82(3), 290-294, (2015).

Glaser, R. et al., "Testosterone Implants in Women: Pharmacological Dosing for a Physiologic Effect," Maturitas, 74:179-184, (2013).

Glaser, R. et al., "Testosterone Therapy in Women: Myths and Misconceptions", Maturitas, 74:230-234, (2013).

Golatta, M. et al., "Evaluation of Virtual Touch Tissue Imaging Quantification, a New Shear Wave Velocity Imaging Method, for Breast Lesion Assessment by Ultrasound", Biomed. Res. Int., 2014:960262, 7 pages, (2014).

Goss, P. et al., "Anastrozole: A New Selective Nonsteroidal Aromatase Inhibitor", Oncology, 11(11): Abstract only (Complete copy from www.cancernetwork.com), 8 pages, (1997).

Goss, P. et al., "Chemoprevention with Aromatase Inhibitors-Trial Strategies", J. Steroid Biochem. Mol. Biol., 79:143-149, (2001).

Goulabchand, R. et al., "Mastitis in Autoimmune Diseases: Review of the Literature, Diagnostic Pathway, and Pathophysiological Key Players", J Clin Med., 9(4):958, (2020).

Gubbels-Bupp, M. et al., "Androgen-Induced Immunosuppression", Front Immunol., 9:974, (2018).

Guhl, S. et al., "Testosterone exerts selective anti-inflammatory effects on human skin mast cells in a cell subset dependent manner", Exp Dermatol., 21(11):878-80, (2012).

Gunter, M. et al., "Circulating Adipokines and Inflammatory Markers and Postmenopausal Breast Cancer Risk", J. Natl. Cancer Inst., 107(9), 10 pages, (2015).

(56) References Cited

OTHER PUBLICATIONS

Haagensen, D. et al., "Breast Gross Cystic Disease Fluid Analysis. I. Isolation and Radioimmunoassay for a Major Component Protein", J. Natl. Cancer Inst., 62(2):239-247, (1979).
Henry, N. et al., "Aromatase inhibitor-induced modulation of breast density: clinical and genetic effects", Br J Cancer, 109(9):2331-9, (2013).
Hodgson, M. et al., "Reduced Androgen Receptor Expression Accelerates the Onset of ERBB2 Induced Breast Tumors in Female Mice", PLoS One, 8(4):e60455, 12 pages, (2013).
Hubalek, M, et al., "Does Obesity Interfere With Anastrozole Treatment? Positive Association Between Body Mass Index and Anastrozole Plasma Levels", Clin. Breast Cancer, 14(4), 6 pages, (2014).
International Application No. PCT/AU2006/001539; International Search Report and Written Opinion of the International Searching Authority, Date of Mailing Jan. 3, 2007; 5 pages.
International Application No. PCT/AU2015/000633; International Preliminary Report on Patentability, Date of Issuance Apr. 25, 2017; 6 pages.
International Application No. PCT/AU2015/000633; International Search Report and Written Opinion of the International Searching Authority, Date of Mailing Dec. 16, 2015; 11 pages.
International Application No. PCT/AU2016/050973; International Search Report and Written Opinion of the International Searching Authority, Date of Mailing Nov. 22, 2016; 9 pages.
International Application No. PCT/AU2020/050562; International Search Report and Written Opinion of the International Searching Authority, Date of Mailing Sep. 2, 2020; 15 pages.
Iobagiu, C. et al., "Loss of Heterozygosity in Tumor Tissue in Hormonal Receptor Genesis Associated with Poor Prognostic Criteria in Breast Cancer", Cancer Genet., 208(4):135-142, (2015).
Ironside, A. et al., "Stromal Characteristics May Hold the Key to Mammographic Density: The Evidence to Date", Oncotarget, 13 pages, (2016).
Japanese Application No. 2008-535845; Office Action with English Translation; dated Jul. 3, 2012; 7 pages.
Javed, A. "Development of the Human Breast", Semin. Plast. Surg., 27(1):5-12 (2013).
Kass, L. et al., "Mammary Epithelial Cell: Influence of Extracellular Matrix Composition and Organization During Development and Tumorigenesis", Int. J. Biochem. Cell Biol., 39(11):1987-1994, (2007).
Li, C. et al., "Effect of Depo-Medroxyprogesterone Acetate on Breast Cancer Risk Among Women 20 to 44 Years of Age", Cancer Res., 72(8):2028-2035, (2012).
Li, X. et al, "Determination of the Elasticity of Breast Tissue During the Menstrual Cycle Using Real-Time Shear Wave Elastography", Ultrasound Med. Biol., 41(12):3140-3147, (2015).
Lienart, V. et al., "Effect of Preventive Hormonal Therapy on Breast Density: A Systematic Qualitative Review", Scientific World Journal, 2014:942386, 24 pages, (2014).
Lillie, E. et al., "Polymorphism in the Androgen Receptor and Mammographic Density in Women Taking and Not Taking Estrogen and Progestin Therapy", Cancer Res., 64(4):1237-1241, (2004).
Linton, L. et al., "Associations of Serum Levels of Sex Hormones in Follicular and Luteal Phases of the Menstrual Cycle with Breast Tissue Characteristics in Young Women", PLoS One, 11(10):e0163865, 14 pages, (2016).
Liu, Y. et al., "Sinomenine hydrochloride inhibits the progression of plasma cell mastitis by regulating IL-6/JAK2/STAT3 pathway", Int Immunopharmacol., 81:106025, (2020).
Lombard, J. et al., "Aromatase Inhibitor Induced Musculoskelelal Syndrome: A Significant Problem with Limited Treatment Options", Support Care Cancer, doi: 10.1007/s00520-015-3001-5, 8 pages, (2015).
Loprinzi, C., "Randomized Double-Blind Placebo Controlled Study of Testosterone in the Adjuvant Treatment of Postmenopausal Women with Aromatase Inhibitor Induced Arthralgias", Alliance for Clinical Trials in Oncology, Study A221102, NCI Version Date (Update #6) Sep. 10, 2018; 130 pages.
Lowdon, R. et al., "Regulatory Network Decoded from Epigenomes of Surface Ectoderm-Derived Cell Types", Nat. Commun., 5:5442, 27 pages, (2014).
Lundin, K. et al., "Androgen Receptor Genotypes Predict Response to Endocrine Treatment in Breast Cancer Patients", Br. J. Cancer, 105(11):1676-1683, (2011).
Miller, WR et al., "The Therapeutic Potential of Aromatase Inhibitors", Expert Opin. Invest. Drugs, 12(3):337-351, (2003).
Mocellin, S. et al., "Breast Cancer Chemoprevention: A Network Meta-Analysis of Randomized Controlled Trials", J. Natl. Cancer Inst., 108(2), 9 pages, (2016).
Mockus, M. et al., "First Pregnancy Characteristics, Postmenopausal Breast Density, and Salivary Sex Hormone Levels in a Population at High Risk for Breast Cancer", BBA Clin., 3:189-195, (2015).
Moshina, N. et al., "Mammographic Density and Histopathologic Characteristics of Screen-Detected Tumors in the Norwegian Breast Cancer Screening Program", Acta Radiol. Open, 4(9), 4 pages, (2015).
Mousa, N. et al., "Aromatase Inhibitors and Mammographic Breast Density in Postmenopausal Women Receiving Hormone Therapy" Menopause, 15(5):875-84, (2008).
Narayanan, R. et al., "Selective Androgen Receptor Modulators (SARMs) Negatively Regulate Triple-Negative Breast Cancer Growth and Epithelial: Mesenchymal Stem Cell Signaling", PLoS One, 9(7):e103202, 12 pages, (2014).
Ng, K-H et al., "Vision 20/20: Mammographic Breast Density and its Clinical Applications", Med. Phys., 42(12):7059-7077, (2015).
Niravath, P., "Aromatase Inhibitor-Induced Arthralgia: A Review", Ann. Oncol., 24(6):1443-1449, (2013).
Ochnik, A. et al., "Antiandrogenic Actions of Medroxyprogesterone Acetate on Epithelial Cells Within Normal Human Breast Tissues Cultured Ex Vivo", Menopause, 21(1):79-88, (2014).
Olsen, N. et al., "Evidence that Androgens Modulate Human Thymic T Cell Output", J. Investig. Med., 59(1):32-35, (2011).
Ouimet-Oliva, D. et al., "Effect of Danazol on the Radiographic Density of Breast Parenchyma", Medline, XP002321074, Nov. 17, 2004; 1 page.
Ozkaya, E. et al., "Is Hyperandrogenemia Protective for Fibrocystic Breast Disease in PCOS?", Gynecol. Endocrinol., 28(6):468-471, (2012).
Park, S. et al., "Androgen Receptor Expression is Significantly Associated With Better Outcomes in Estrogen Receptor-Positive Breast Cancers", Annals of Oncology, 22:1755-1762, (2011).
Parsanezhad, M. et al., "A Randomized, Controlled Clinical Trial Comparing the Effects of Aromatase Inhibitor (Letrozole) and Gonadotropin-Releasing Hormone Agonist (Triptorelin) on Uterine Leiomyoma Volume and Hormonal Status", Fertil. Steril., 93(1):192-198, (2010).
Peres, J., "Why Is Breast Cancer Chemoprevention Such a Hard Sell?", J. Natl. Cancer Inst., 106(5):4-6, (2014).
Pettersson, A. et al., "Mammographic Density Phenotypes and Risk of Breast Cancer: A Meta-Analysis", J. Natl. Cancer Inst., 106(5):dju078, 11 pages, (2014).
Pike, MC et al., "Mammographic Density, MRI Background Parenchymal Enhancement and Breast Cancer Risk", Ann. Oncol., 24(Suppl 8):viii37-viii41, (2013).
Plourde, P. et al., "Arimidex®: A Potent and Selective Fourth-Generation Aromatase Inhibitor", Breast Cancer Res. Treat., 30:103-111, (1994).
Priority document AU 2005905768, dated Oct. 19, 2005, for International Application No. PCT/ AU2006/001539, publicly made available on WIPO on Feb. 26, 2007; 23 pages.
Priority document U.S. Appl. No. 60/732,662, dated Nov. 3, 2005, for International Application No. PCT/ AU2006/001539, publicly made available on WIPO on Feb. 26, 2007; 21 pages.
Priority document U.S. Appl. No. 60/798,308, dated May 8, 2006, for International Application No. PCT/ AU2006/001539, publicly made available on WIPO on Feb. 26, 2007; 33 pages.

(56) References Cited

OTHER PUBLICATIONS

Rhoden, EL et al., "Treatment of Testosterone-Induced Gynecomastia with the Aromatase Inhibitor, Anastrozole", Intl. J. of Impotence Res., 16:95-97, (2004).
Rinsho, et al., Japanese Journal of Clinical and Experimental Medicine, 70(11):3428-3433, 7 pages, (1993).
Robinson, J. et al., "Androgen Receptor Driven Transcription in Molecular Apocrine Breast Cancer is Mediated by FoxA1", EMBO J., 30(15):3019-3027, (2011).
Robinson, J. et al., "FoxA1 is a Key Mediator of Hormonal Response in Breast and Prostate Cancer", Front. Endocrin., 3(68):1-6, (2012).
Santen, R., "Recent Progress in Development of Aromatase Inhibitors", J. Steroid Biochem. Molec. Biol., 37(6):1029-1035, (1990).
Scurr, J. et al., "The Prevalence, Severity, and Impact of Breast Pain in the General Population", Breast J., 20(5):508-13, (2014).
Smith, J. et al., "A Pilot Study of Letrozole for One Year in Women at Enhanced Risk of Developing Breast Cancer: Effects on Mammographic Density", Anticancer Res., 32(4):1327-31, (2012).
Smith, R. et al., "Evaluation and Management of Breast Pain", Mayo Clin. Proc., 79:353-372, (2004).
Somboonporn, W. et al., "Postmenopausal Testosterone Therapy and Breast Cancer Risk", Maturitas, 49:267-275, (2004).
Tarone, R. et al., "Breast Reduction Surgery and Breast Cancer Risk: Does Reduction Mammaplasty Have a Role in Primary Prevention Strategies for Women at High Risk of Breast Cancer?", Plasl. Reconstr. Surg., 113(7):2104-2110, (2004).
The Merck Index, 13th ed., Merck & Co., Inc., Entry Nos. 632 (p. 105), 3944 (p. 692) and 9255 (p. 1638), (2001).
The North American Menopause Society, "The Role of Testosterone Therapy in Postmenopausal Women: Position Statement of The North American Menopause Society", Menopause, 12(5):497-511, (2005).
Titus-Ernstoff, L. et al, "Breast Cancer Risk Factors in Relation to Breast Density (United States)", Cancer Causes Control, 17(10):1281-1290, (2006).
Tiwary, B. et al., "Parallel Evolution Between Aromatase and Androgen Receptor in the Animal Kingdom", Mol. Biol. Evol., 26(1):123-129, (2009).
Touraine, P. et al., "Breast inflammatory gigantomastia in a context of immune-mediated diseases", J Clin Endocrinol Metab., 90(9):5287-94, (2005).
U.S. Appl. No. 15/460,895; Non-Final Office Action, dated Dec. 19, 2017; 17 pages.
U.S. Appl. No. 17/437,525; Corrected Notice of Allowance, dated May 11, 2022; 6 pages.
U.S. Appl. No. 17/437,525; Non-Final Office Action, dated Jan. 27, 2022; 36 pages.
U.S. Appl. No. 17/437,525; Notice of Allowance, dated Apr. 26, 2022; 13 pages.
Uray, I. et al., "Estradiol down-regulates CD36 expression in human breast cancer cells", Cancer Lett., 207(1):101-7, (2004).
Vachon, C. et al., "Mammographic Breast Density Response to Aromatase Inhibition", Clin. Cancer Res., 19(8):2144-2153, (2013).
Viacava, P. et al., "Spectrum of GCDFP-15 Expression in Human Fetal and Adult Normal Tissues", Virchows Arch, 432:255-260, (1998).
Walecki, M. et al., "Androgen receptor modulates Foxp3 expression in CD4+CD25+Foxp3+ regulatory T-cells", Mol Biol Cell., 26(15):2845-57, (2015).
Wanders, J. et al., "The Effect of Weight Change on Changes in Breast Density Measures Over Menopause in a Breast Cancer Screening Cohort", Breast Cancer Res., 8 pages, (2015).
Wang, H. et al., "CD36-mediated metabolic adaptation supports regulatory T cell survival and function in tumors", Nat Immunol., 21(3):298-308, (2020).
Warwick, J. et al., "Mammographic Breast Density Refines Tyrer-Cuzick Estimates of Breast Cancer Risk in High-Risk Women: Findings from the Placebo Arm of the International Breast Cancer Intervention Study I", Breast Cancer Res., 16:451, 6 pages, (2014).

Wasaff, Barbara, "Current Status of Hormonal Treatments for Metastatic Breast Cancer in Postmenopausal Nomen," Oncol. Nurs. Forum, 24(9), 1515-1520 (1997).
Wu, S. et al., "Quantitative Assessment of Background Parenchymal Enhancement in Breast MRI Predicts Response to Risk-Reducing Salpingo-Oophorectomy: Preliminary Evaluation in a Cohort of BRCA 1/2 Mutation Carriers", Breast Cancer Res., 11 pages, (2015).
Yang, Y. et al., "Influence of Factors on Mammographic Density in Premenopausal Chinese Women", Eur. J. Cancer Prev., 6 pages, (2015).
Youk, J. et al., "Quantitative Lesion-to-Fat Elasticity Ratio Measured by Shear-Wave Elastography for Breast Mass: Which Area Should Be Selected as the Fat Reference?", PLoS One, 10(9):e0138074, 11 pages, (2015).
Zhong, A. et al., "Stromal-Epithelial Cell Interactions and Alteration of Branching Morphogenesis in Macromastic Mammary Glands", J. Cell Mol. Med., 18(7):1257-1266, (2014).
Zhou, J. et al., "Testosterone Inhibits Estrogen-Induced Mammary Epithelial Proliferation and Suppresses Estrogen Receptor Expression", FASEB J., 14:1725-1730 (2000).
Zimmerman, Y. et al., "The Effect of Combined Oral Contraception on Testosterone Levels in Healthy Women: A Systematic Review and Meta-Analysis," Hum. Reprod. Update, 20(1):76-105, (2014).
Atakpa, E. et al., "Mammographic density, endocrine therapy and breast cancer risk: a prognostic and predictive biomarker review", Cochrane Database Syst Rev., 10(10):CD013091, (2021).
Brown, P., "Targeted Therapy—Anastrozole Prevents Breast Cancer", Nature Reviews Clinical Oncology, 11:127-128, (2014).
Cigler, T. et al., "A randomized, placebo-controlled trial (NCIC CTG MAP1) examining the effects of letrozole on mammographic breast density and other end organs in postmenopausal women", Breast Cancer Res Treat., 120(2):427-35, (2010).
De Gooyer, M. et al., "Tibolone is not converted by human aromatase to 7α-methyl-17α-ethynylestradiol (7α-MEE): analyses with sensitive bioassays for estrogens and androgens and with LC-MSMS", Steroids, 68(3):235-43, (2003).
EP Application No. 20818587.6; Extended European Search Report and Written Opinion, dated Jun. 12, 2023; 6 pages.
Glaser, R. et al., "Subcutaneous Testosterone Anastrozole Therapy in Men: Rationale, Dosing, and Levels on Therapy", Int J Pharma Compd., 23(4):325-39, (2019).
Imahori, K., "Substrate specificity of enzymatic reaction", High Polymers, pp. 794-7, (1971).
Li, G. et al., "Effects of aromatizable and nonaromatizable androgens on the sex inversion of red-spotted grouper (Epinephelus akaara)", Fish Physiol Biochem., 32(1):25-33, (2006).
Mor, G. et al., "17α-Methyl testosterone is a competitive inhibitor of aromatase activity in Jar choriocarcinoma cells and macrophage-like THP-1 cells in culture", J Steroid Biochem Mol Biol., 79(1-5):239-46, (2001).
Mukawa, F., "Aromatase inhibitors", J Synth Org Chem., 46(8):742-52, (2008).
Passaperuma, K. et al., "Is mammographic breast density a breast cancer risk factor in women with BRCA mutations?", J Clin Oncol., 28(23):3779-83, (2010).
Pitot, H., "The molecular biology of carcinogenesis", Cancer, 72(S3):962-70, (1993).
Saria, M., "Overview of Cancer", Oncol Nursing Soc., pp. 1-11, (2018).
Seo, J. et al., "Automated volumetric breast density estimation: a comparison with visual assessment", Clin Radiol., 68(7):690-5, (2013).
Shawky, M. et al., "Mammographic density: a potential monitoring biomarker for adjuvant and preventative breast cancer endocrine therapies", Oncotarget, 8(3):5578-91, (2017).
Simpson, E. et al., "Aromatase and its inhibitors: significance for breast cancer therapy", Recent Prog Horm Res., 57:317-38, (2002).
Smith, I. et al., "Comparative Efficacy and Safety of Adjuvant Letrozole Versus Anastrozole in Postmenopausal Patients With Hormone Receptor-Positive, Node-Positive Early Breast Cancer:

(56) References Cited

OTHER PUBLICATIONS

Final Results of the Randomized Phase III Femara Versus Anastrozole Clinical Evaluation (FACE) Trial", J Clin Oncol., 35(10):1041-8, (2017).
U.S. Appl. No. 17/344,052; Notice of Allowance, dated Sep. 13, 2023; 13 pages.

* cited by examiner

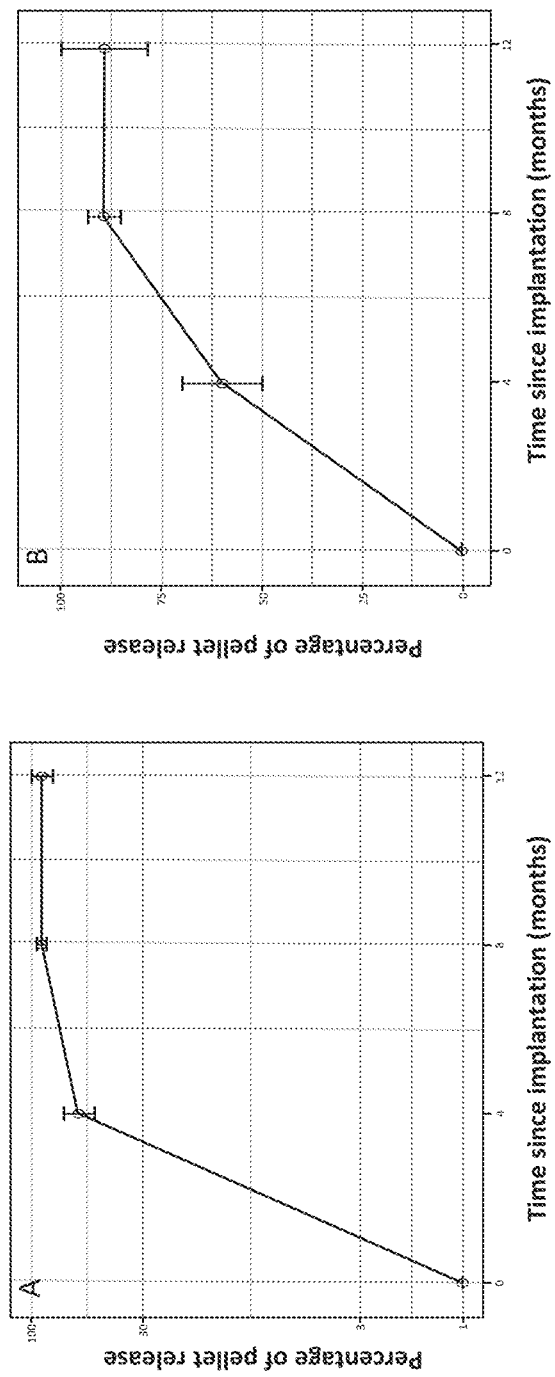
Figures 7A-B

Figure 19
A
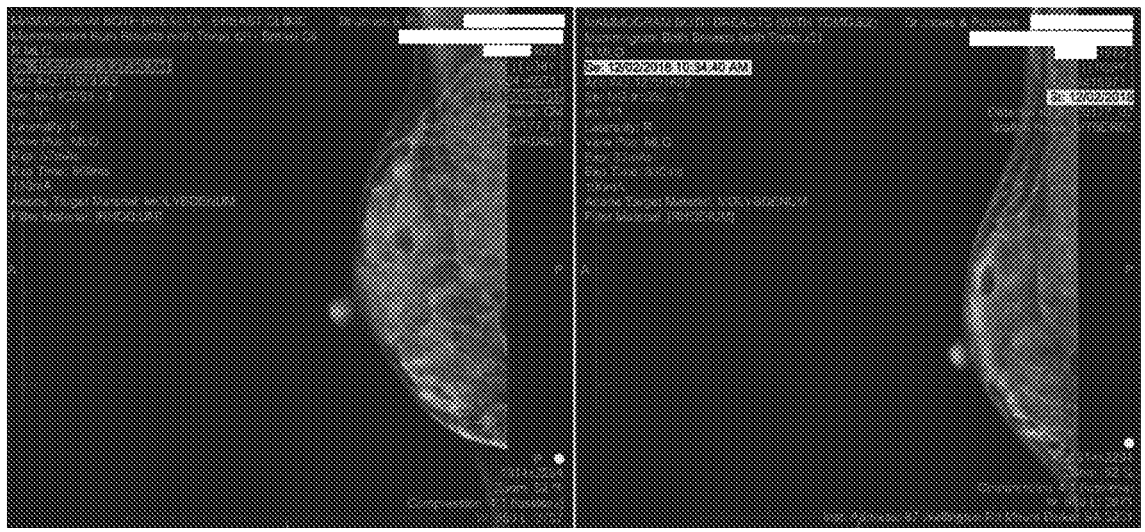
B
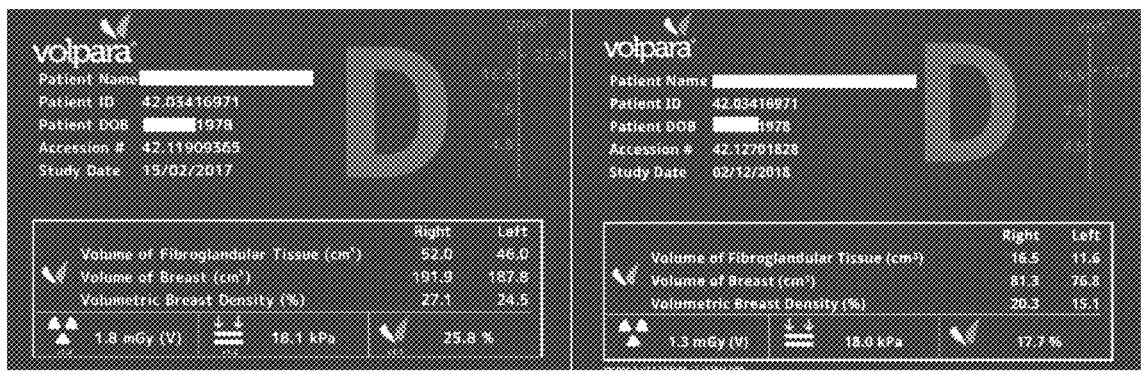
C

Figure 20
A
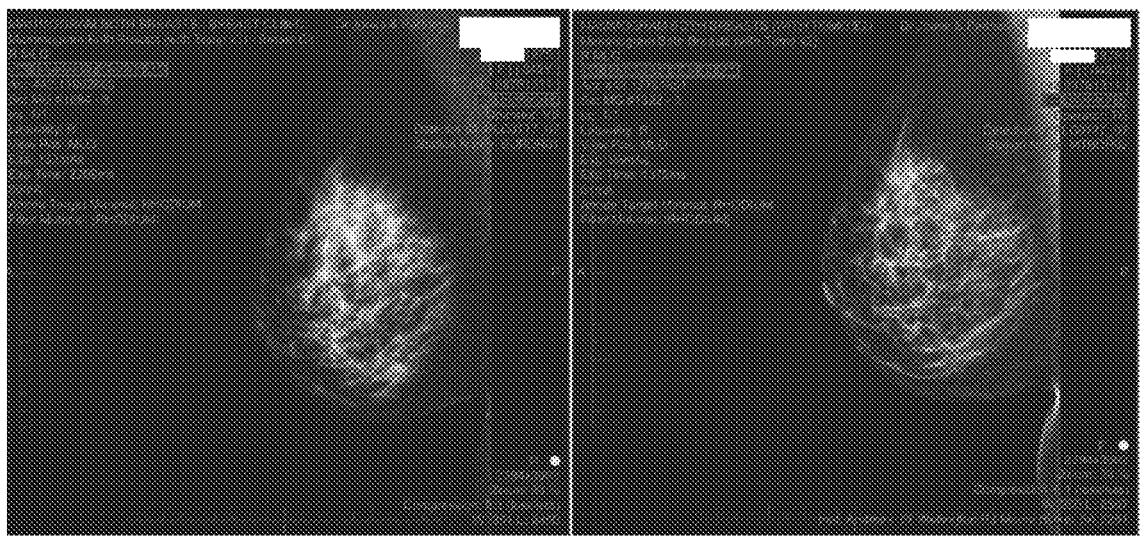
B
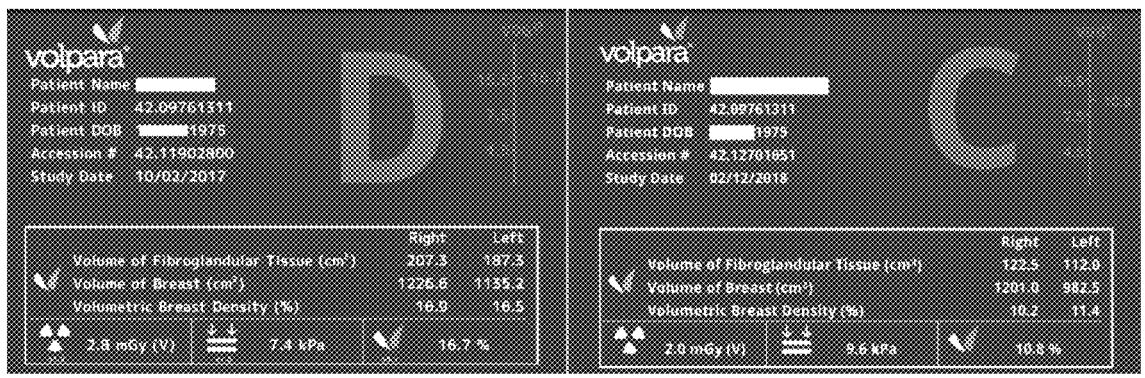

Figure 21
A
B
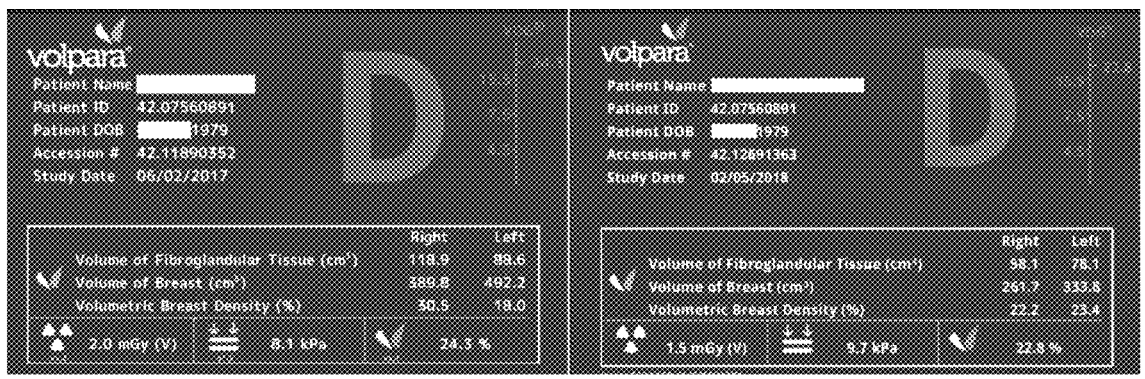

Figure 22
A
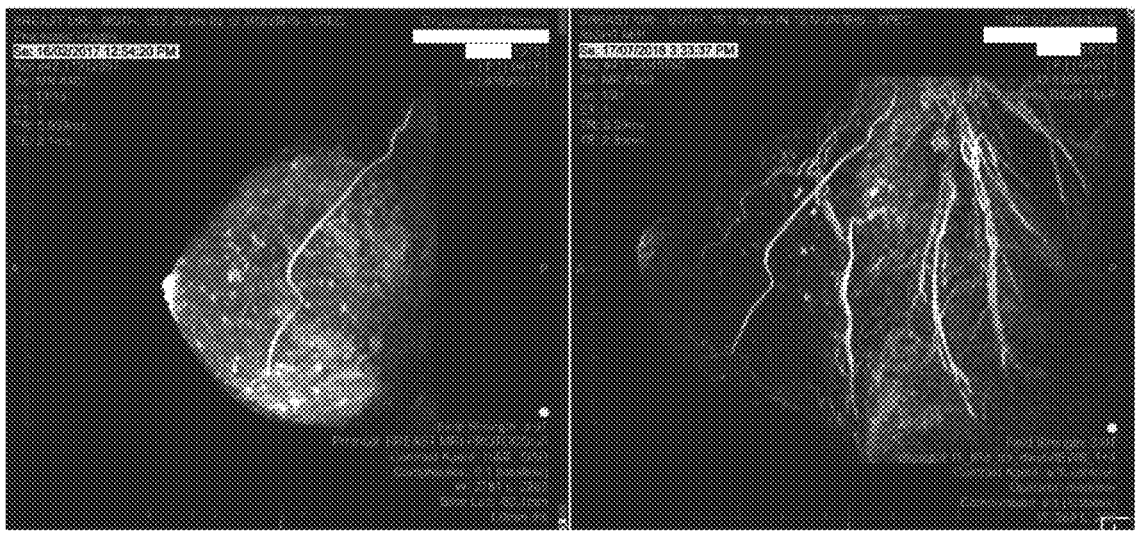
B
C
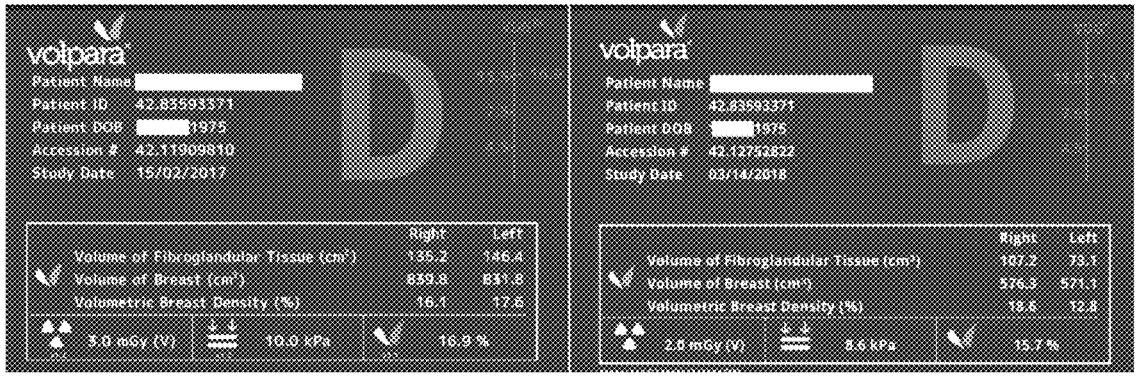

PHARMACEUTICAL FORMULATIONS AND SYSTEMS FOR DELIVERY OF AN ANDROGENIC AGENT AND AN AROMATASE INHIBITOR WITH SUSTAINED MULTI-PHASIC RELEASE PROFILES AND METHODS OF USE

BACKGROUND

Testosterone is critical in the regulation of immune function in both men and women (Gubbels Bupp, 2018). There are several physiological and disease states where it is desirable to increase the tissue level of 5 alpha dihydrotestosterone (DHT) while at the same time reducing oestradiol level within the same tissue without causing significant perturbations in serum oestradiol levels. DHT is predominantly an intra-tissue hormone derived from testosterone which is delivered to that tissue via the circulation. Delivery of testosterone to the tissue which requires treatment in women is problematic due to the relatively small therapeutic window available to dose with testosterone without causing androgenic side-effects.

Within most tissues, there is also five alpha reductase enzyme which converts testosterone to DHT. Therefore, in a therapeutic situation where it is desirable to increase DHT without increasing oestradiol there is an unmet need which the present disclosure is directed to provide pharmaceutical formulations that work towards inhibition of aromatase enzyme and induction of 5 alpha reductase enzyme to effect an alteration in the DHT to oestradiol ratio within that tissue.

Both in men and women subcutaneous testosterone has been used to deliver zero-order kinetic dosing of testosterone. However, the use of testosterone alone in many physiological and disease states is not desirable due to the high level of aromatase enzyme within the tissue, which is undergoing therapeutic intervention. An example of this is women with high mammographic breast density where there is a very high level of aromatase enzyme within the tissue, which converts testosterone preferentially to oestradiol. It has been estimated that 43% of women in the United States of America from 40 and 75 years of age have mammographic breast density (MBD), which is categorized as high, i.e., having a Breast Imaging-Reporting and Data System (BI-RADS®) score of 3 and 4 (or c and d). The American Cancer Foundation has suggested that this high breast density is a significant risk factor for the development of breast cancer. Traditionally, therapeutic intervention for the perimenopausal transition is either a low dose combination oral contraceptive or continuous estradiol and a synthetic progestin delivery system to protect the uterus from both increased endometrial cancer risk and unwanted uterine bleeding. This an inappropriate treatment for women with high breast density and/or breast stiffness as they reduce an already precarious testosterone level and increase breast density and/or breast stiffness. However, these are the current recommendations of the Menopause Society of North America and the Menopause Society of Australia.

Another problem in the prior art is breast pain and its treatment. Breast pain is a significant problem in female health. It has been estimated that 45% of woman in their thirties indicated that breast pain impinges on their quality of life, and 10% indicated that they had experienced breast pain for at least half their life. There is little in the way of treatment; tamoxifen and aromatase inhibitors have been used as an off-label medication for this condition. However, tamoxifen is associated with significant side effects that impact on its compliance in patients, and aromatase inhibitors have been contraindicated in pre-menopausal women as a single agent due to resultant purterbations in the hypothalamic-pituitary-ovarian axis. There is a need in the art for better treatments to reduce breast pain in women.

The elasticity of breast tissue is recognized as a factor in the formation of breast cancer. It has been demonstrated that increased elasticity in breast cells results in an increased mechano-transduction across the genome of a cell, which may result in greater malignant transformation. There is a need in the art for compositions that provide pharmaceutical formulations that decreases mechano-transduction on the genome of a cell to reduce the risk of malignant transformation.

A further problem in the art is that of tissue specific autoimmune inflammatory conditions, particularly those presenting in the breast. These conditions may be termed Autoimmune Inflammatory Mastitis (AIM). The anatomical, histological, and physiological roles of salivary glands and mammary glands are similar as they both belong to the effector sites of the associated mucosal immune system leaving them vulnerable to autoimmunity. Autoimmune breast tissue, compared to normal breast tissue, has been demonstrated to have elevated aromatase (that converts androgens to estradiol) and other factors associated with inflammation, such as IGF2, EGFR, TGF-β, PDGFR-α and β, which have been found to be upregulated. AIM is usually treated with heavy immunosuppressive therapy and/or disfiguring surgery and there is therefore a need for an improved therapy.

How a drug composition is delivered and it impacts on a body may be related to the pharmacokinetics and/or pharmacodynamics profile of the drug composition, the drug delivery system and/or where the drug is delivered to the subject's body. In broad terms, pharmacokinetics is a description of the rate and extent of uptake, distribution and/or elimination of drugs in the body. In other words, how a body, or a portion of the body, affects a drug composition. In broad terms, pharmacodynamics is a description of how drugs affect the body or a portion of the body. Drug compositions may have different pharmacokinetics and/or pharmacodynamics profiles. For example, some drug compositions may have zero order, first order, or second order kinetics. The kinetics and/or dynamics may have an impact on the efficacy of a drug composition and/or the efficacy of the on treatment. Thus, the role that pharmacokinetics and/or pharmacodynamics plays in certain drug compositions, or certain drug delivery systems may be relevant to a particular drug, drug composition, and/or outcome for a subject.

Previously implants have been produced that combine testosterone with an aromatase inhibitor so that there may be an inhibition of the conversion of testosterone to oestradiol. However, if the manufacture and concentration of the compounds result in the active ingredients being delivered via zero-order kinetics, the end result is a lowering of serum oestradiol level which is not desirable in many situations as it results in estrogen deprivation symptoms and the potential for side effects from higher sustained levels of the aromatase inhibitor. There is an ongoing need for a pharmaceutical formulation and/or delivery system for providing a high intra-tissue DHT to oestradiol ratio. There is also an ongoing need for alternatives to currently available treatments for diseases and conditions for which an increase in the tissue level of 5 alpha-dihydrotestosterone (DHT) whilst at the same time reducing oestradiol level within the same tissue without causing significant perturbations in serum oestradiol levels is beneficial.

The present disclosure in one or more embodiments is directed to addressing and/or ameliorating one or more of the disadvantages of the prior art, or to at least provide a useful pharmaceutical formulation or therapeutic delivery system, as will become apparent from the disclosure herein. The present disclosure in one or more embodiments may also provide other advantages and/or improvements as discussed herein.

SUMMARY

To obtain high intra-tissue DHT to oestradiol ratio, the present inventor has recognised there is an urgent need for a delivery system which delivers testosterone and aromatase inhibitor in a multi-phasic release pattern. In one or more embodiments of a pharmaceutical formulation described herein there may be provided an early peak of serum testosterone, which is rapidly blocked by a high level of aromatase inhibitor allowing the induction of 5 alpha reductase conversion of testosterone to DHT. The formulation may then provide for a rapid reduction of the aromatase inhibitor to ensure that there is not a blockade globally of oestradiol production and symptomatic lowering of oestradiol level in the serum. The alteration of the axis towards an elevated DHT to oestradiol level in tissues where there is overexpression of aromatase may be achieved with the utilisation of this multi-phasic release pattern. If, for example, zero-order kinetics for both components is utilised there will not be a release of the genesis of oestradiol which will result in detrimental effects to the woman and the unwanted long-term exposure of the woman to higher levels of an aromatase inhibitor than is required for a therapeutic response.

In an aspect of the invention there is provided a pharmaceutical formulation comprising: an effective amount of an androgenic agent, an effective amount of an aromatase inhibitor and a binding agent; the formulation upon administration to a subject provides a sustained release multi-phasic concentration pattern in the blood of the subject over time as measured by serum concentration for the androgenic agent and plasma concentration for the aromatase inhibitor; and the sustained release multi-phasic concentration pattern in the serum or plasma of the subject comprising:
  a first time period in which the androgenic agent, has a first peak in concentration (Tmax) in the serum and the aromatase inhibitor is increasing in concentration in the plasma but is below its Tmax concentration in the plasma; and
  a second time period in which the androgenic agent, has initially a decreasing serum level concentration and then an increasing serum level concentration and the aromatase inhibitor has its Tmax concentration in the plasma.

In another aspect of the invention there is provided a pharmaceutical formulation comprising: an effective amount of an androgenic agent, an effective amount of an aromatase inhibitor and a binding agent; the formulation upon administration to a subject provides a sustained release multi-phasic concentration pattern in the blood of the subject over time as measured by serum concentration for the androgenic agent and plasma concentration for the aromatase inhibitor; and the sustained release multi-phasic concentration pattern in the serum or plasma of the subject comprising:
  a first time period in which the androgenic agent, has a first peak in concentration (Tmax) in the serum and the aromatase inhibitor is increasing in concentration in the plasma but is below its Tmax concentration in the plasma;
  a second time period in which the androgenic agent, has initially a decreasing serum level concentration and then an increasing serum level concentration and the aromatase inhibitor has its Tmax concentration in the plasma;
  a third time period in which the androgenic agent, has a second peak concentration in the serum that is less than the Tmax and the aromatase inhibitor is gradually decreasing in concentration in the plasma and in the third time period falls below the concentration of the androgenic agent; and
  a fourth time period in which the androgenic agent has a gradually decreasing serum level concentration and the aromatase inhibitor has a gradually decreasing concentration in the plasma and both decreasing levels approximately parallel each other.

In another aspect of the invention there is provided a pharmaceutical formulation comprising: an effective amount of an androgenic agent, an effective amount of an aromatase inhibitor and a binding agent; the pharmaceutical formulation is compressed into a pellet; the pellet upon subcutaneous administration to a subject provides a sustained release multi-phasic concentration pattern in the blood of the subject over time as measured by serum concentration for the androgenic agent and plasma concentration for the aromatase inhibitor; and the sustained release multi-phasic concentration pattern in the serum or plasma of the subject comprising:
  a first time period in which the androgen, has a first peak in concentration (Tmax) in the serum and the aromatase inhibitor is increasing in concentration in the plasma but is below its Tmax concentration in the plasma; and
  a second time period in which the androgenic agent, has initially a decreasing serum level concentration and then an increasing serum level concentration and the aromatase inhibitor has its Tmax concentration in the plasma.

In another aspect of the invention there is provided a pharmaceutical formulation comprising: an effective amount of an androgenic agent, an effective amount of an aromatase inhibitor and a binding agent; the pharmaceutical formulation is compressed into a pellet; the pellet upon subcutaneous administration to a subject provides a sustained release multi-phasic concentration pattern in the blood of the subject over time as measured by serum concentration for the androgenic agent and plasma concentration for the aromatase inhibitor; and the sustained release multi-phasic concentration pattern in the serum or plasma of the subject comprising:
  a first time period in which the androgenic agent, has a first peak in concentration (Tmax) in the serum and the aromatase inhibitor is increasing in concentration in the plasma but is below its Tmax concentration in the plasma;
  a second time period in which the androgenic agent, has initially a decreasing serum level concentration and then an increasing serum level concentration and the aromatase inhibitor has its Tmax concentration in the plasma;
  a third time period in which the androgenic agent, has a second peak concentration in the serum that is less than the Tmax and the aromatase inhibitor is gradually decreasing in concentration in the plasma and in the third time period falls below the concentration of the androgenic agent; and a fourth time period in which the androgenic agent has a gradually decreasing serum level concentration and the aromatase inhibitor has a gradually decreasing concentration in the plasma and both decreasing levels approximately parallel each other.

In at least some embodiments the pharmaceutical formulation comprises: 60 mg to 120 mg of a testosterone, or an ester thereof, 2 mg to 6 mg of an aromatase inhibitor, more preferably 4 mg to 6 mg of an aromatase inhibitor, and stearic acid; the pharmaceutical formulation is compressed into a pellet that has a diameter of between 4.25 mm to 4.75 mm and a length of between 4 mm to 7 mm; the pellet upon subcutaneous administration to a subject provides a sustained release multi-phasic concentration pattern in the blood of the subject over time as measured by serum concentration for the testosterone or an ester thereof, and plasma concentration for the aromatase inhibitor; and the sustained release multi-phasic concentration pattern comprises:

a first time period in which the testosterone or an ester thereof, has a first peak in concentration (Tmax) in the serum and the aromatase inhibitor is increasing in concentration in the plasma but is below its Tmax concentration in the plasma; and a second time period in which the testosterone or an ester thereof, has initially a decreasing serum level concentration and then an increasing serum level concentration and the aromatase inhibitor has its Tmax concentration in the plasma.

In at least some embodiments the pharmaceutical formulation comprises: 60 mg to 120 mg of a testosterone, or an ester thereof, 2 mg to 6 mg of an aromatase inhibitor, more preferably 4 mg to 6 mg of an aromatase inhibitor, and stearic acid; the pharmaceutical formulation is compressed into a pellet that has a diameter of between 4.25 mm to 4.75 mm and a length of between 4 mm to 7 mm; the pellet upon subcutaneous administration to a subject provides a sustained release multi-phasic concentration pattern in the blood of the subject over time as measured by serum concentration for the testosterone or an ester thereof, and plasma concentration for the aromatase inhibitor; and the sustained release multi-phasic concentration pattern comprises:

a first time period in which the testosterone or an ester thereof, has a first peak in concentration (Tmax) in the serum and the aromatase inhibitor is increasing in concentration in the plasma but is below its Tmax concentration in the plasma;

a second time period in which the testosterone or an ester thereof, has initially a decreasing serum level concentration and then an increasing serum level concentration and the aromatase inhibitor has its Tmax concentration in the plasma;

a third time period in which the testosterone or an ester thereof, has a second peak concentration in the serum that is less than the Tmax and the aromatase inhibitor is gradually decreasing in concentration in the plasma and in the third time period falls below the concentration of the testosterone or an ester thereof; and a fourth time period in which the testosterone or an ester thereof, has a gradually decreasing serum level concentration and the aromatase inhibitor has a gradually decreasing concentration in the plasma and both decreasing levels approximately parallel each other.

In certain exemplary embodiments, in the pharmaceutical formulation during the first time period the aromatase inhibitor does not exhibit zero-order release.

In certain exemplary embodiments, in the pharmaceutical formulation during the first time period the aromatase inhibitor exhibits first order release.

In certain exemplary embodiments, in the pharmaceutical formulation during the second time period the aromatase inhibitor does not exhibit zero order release.

In certain exemplary embodiments, in the pharmaceutical formulation during the second time period the androgenic agent (e.g., testosterone or an ester thereof), does not exhibit zero order release.

In certain exemplary embodiments, in the pharmaceutical during the third time period the aromatase inhibitor does not exhibit zero order release.

In certain exemplary embodiments, in the pharmaceutical formulation during the third time period the androgenic agent, does not exhibit zero order release.

In certain exemplary embodiments, in the pharmaceutical formulation during the third time period the aromatase inhibitor exhibits first order release.

In certain exemplary embodiments, in the pharmaceutical formulation during the third time period the androgenic agent, exhibits first order release.

In certain exemplary embodiments, in the pharmaceutical formulation during the fourth time period the aromatase inhibitor does not exhibit zero order release.

In certain exemplary embodiments, in the pharmaceutical formulation during the fourth time period the androgenic agent, does not exhibit zero order release.

In certain exemplary embodiments, in the pharmaceutical formulation during the fourth time period the aromatase inhibitor exhibits first order release.

In certain exemplary embodiments, in the pharmaceutical formulation during the fourth time period the androgenic agent, exhibits first order release.

In certain exemplary embodiments of the pharmaceutical formulation the first time period ends right after the androgen has a first peak in concentration (Tmax) in the serum. In certain exemplary embodiments of the pharmaceutical formulation the first time period ends between 5 hours to 14 hours. In certain exemplary embodiments of the pharmaceutical formulation the first time period ends between 5.5 hours to 13 hours.

In certain exemplary embodiments of the pharmaceutical formulation the second time period ends right after the aromatase inhibitor has its Tmax. In certain exemplary embodiments of the pharmaceutical formulation the second time period ends between 23 hours to 80 hours.

Moreover, certain embodiments are directed to a pharmaceutical formulation comprising: approximately 80 mg of a testosterone or an ester thereof, approximately 4 mg anastrozole and approximately 2 mg of a stearic acid; the pharmaceutical formulation is compressed into a pellet that has a diameter of between 4.4 mm to 4.6 mm and a length of between 4 mm to 7 mm; the pellet upon subcutaneously administration to a subject provides a sustained release multi-phasic concentration pattern in the blood of the subject over time as measured by serum concentration for the testosterone or an ester thereof, and plasma concentration for the anastrozole; the sustained release multi-phasic concentration pattern comprising: a first time period of in which the testosterone or an ester thereof, has a first peak in concentration (Tmax) in the serum and the anastrozole is increasing in concentration in the plasma but is below its Tmax concentration in the plasma; a second time period in which the testosterone or an ester thereof, has initially a decreasing serum level concentration and then an increasing serum level concentration and the anastrozole has its Tmax concentration in the plasma; a third time period in which the testosterone or an ester thereof, has a second peak concentration in the serum that is less than the Tmax and the anastrozole is gradually decreasing in concentration in the plasma and in the third time period falls below the concentration of the testosterone or an ester thereof; and a fourth time period in which the testosterone or an ester thereof, has a gradually decreasing serum level concentration and the anastrozole has a gradually decreasing concentration in the plasma and both decreasing levels approximately parallel each other. Methods of using the pharmaceutical formulation are also disclosed.

Further embodiments are directed to a pharmaceutical formulation comprising: an effective amount of an androgenic agent an effective amount of an aromatase inhibitor and a binding agent; the pharmaceutical formulation is compressed into a pellet; the pellet upon subcutaneously administration to a subject provides a sustained release multi-phasic concentration pattern in the blood of the subject over time as measured by serum concentration for the androgenic agent and plasma concentration for the aromatase inhibitor; and the sustained release multi-phasic concentration pattern in the serum or plasma of the subject comprising: a first time period in which the androgenic agent has a first peak in concentration (Tmax) in the serum and the aromatase inhibitor does not have its Tmax concentration in the plasma; a second time period in which the androgenic agent has a decreasing serum level concentration and then an increasing serum level concentration and the aromatase inhibitor has its Tmax concentration in the plasma; a third time period in which the androgenic agent has a second peak concentration in the serum that is less than its Tmax and the aromatase inhibitor is gradually decreasing in concentration in the plasma and in the third time period falls below the concentration of the androgenic agent and a fourth time period in which the androgenic agent has a decreasing serum level concentration and the aromatase inhibitor has a decreasing concentration in the plasma.

Further embodiments are directed to methods of reducing mammographic breast density, as measured by AVBD and/or VBD %, in a patient in need thereof, comprising administering to the patient a subcutaneous pellet comprising: i) an effective amount of androgenic agent; and ii) an effective amount of an aromatase inhibitor.

Further embodiments are directed to a use of a pharmaceutical formulation in methods of reducing VBD % in a patient in need thereof, comprising administering to the patient a subcutaneous pellet comprising: i) an effective amount of androgenic agent; and ii) an effective amount of an aromatase inhibitor.

Further embodiments are directed to use of a pharmaceutical formulation in methods of reducing AVBD in a patient in need thereof, comprising administering to the patient a subcutaneous pellet comprising: i) an effective amount of androgenic agent; and ii) an effective amount of an aromatase inhibitor.

Further embodiments are directed to use of a pharmaceutical formulation in methods of reducing AVBD and VBD % in a patient in need thereof, comprising administering to the patient a subcutaneous pellet comprising: i) an effective amount of androgenic agent; and ii) an effective amount of an aromatase inhibitor.

Further embodiments are directed to use of a pharmaceutical formulation in methods of treating mammographic breast density, as measured by AABD and/or ABD %, in a patient in need thereof, comprising administering to the patient a subcutaneous pellet comprising: i) an effective amount of androgenic agent; and ii) an effective amount of an aromatase inhibitor.

Further embodiments are directed to use of a pharmaceutical formulation in methods of reducing ABD % in a patient in need thereof, comprising administering to the patient a subcutaneous pellet comprising: i) an effective amount of androgenic agent; and ii) an effective amount of an aromatase inhibitor.

Further embodiments are directed to use of a pharmaceutical formulation in methods of reducing AABD in a patient in need thereof, comprising administering to the patient subcutaneous pellet comprising: i) an effective amount of androgenic agent; and ii) an effective amount of an aromatase inhibitor.

Further embodiments are directed to use of a pharmaceutical formulation in methods of reducing AABD and ABD % in a patient in need thereof, comprising administering to the patient a subcutaneous pellet comprising: i) an effective amount of androgenic agent; and ii) an effective amount of an aromatase inhibitor.

Further embodiments are directed to use of a pharmaceutical formulation in methods of reducing mammographic breast density in a patient having a breast with a mammographic breast density of 7.5% or greater, comprising administering to the patient a subcutaneous pellet comprising: i) an effective amount of androgenic agent; and ii) an effective amount of an aromatase inhibitor.

Further embodiments are directed to use of a pharmaceutical formulation in methods of reducing VBD % in a patient having a breast with a VBD % of 7.5% or greater, comprising administering to the patient a subcutaneous pellet comprising: i) an effective amount of androgenic agent; and ii) an effective amount of an aromatase inhibitor.

Further embodiments are directed to use of a pharmaceutical formulation in methods of reducing ABD % in a patient having a breast with an ABD % of 7.5% or greater, comprising administering to the patient a subcutaneous pellet comprising: i) an effective amount of androgenic agent; and ii) an effective amount of an aromatase inhibitor.

Further embodiments are directed to use of a pharmaceutical formulation in methods of treating mammographic breast density in a patient having a breast with a BI-RADS® score of 3 or 4 (or c or d), comprising administering to the patient a subcutaneous pellet comprising: i) an effective amount of androgenic agent; and ii) an effective amount of an aromatase inhibitor.

Further embodiments are directed to use of a pharmaceutical formulation in methods of reducing mammographic breast density in a patient having a breast with a BI-RADS® score of 3 or 4 (or c or d), comprising administering to the patient a subcutaneous pellet comprising: i) an effective amount of androgenic agent; and ii) an effective amount of an aromatase inhibitor.

Further embodiments are directed to use of a pharmaceutical formulation in methods of inducing breast involution in a patient in need thereof, comprising administering to the patient a subcutaneous pellet comprising: i) an effective amount of androgenic agent; and ii) an effective amount of an aromatase inhibitor.

Further embodiments are directed to use of a pharmaceutical formulation in methods of inducing net cell death over proliferation in a breast of a patient in need thereof, comprising administering to the patient a subcutaneous pellet comprising: i) an effective amount of androgenic agent; and ii) an effective amount of an aromatase inhibitor.

Further embodiments are directed to use of a pharmaceutical formulation in methods of inducing net extracellular matrix degradation over development of extracellular matrix in a breast of a patient in need thereof, comprising administering to the patient a subcutaneous pellet comprising: i) an effective amount of androgenic agent; and ii) an effective amount of an aromatase inhibitor.

Further embodiments are directed to use of a pharmaceutical formulation in methods of reversing cell number and mammographic breast density in a breast of a peri-menopausal patient, comprising administering to the patient a subcutaneous pellet comprising: i) an effective amount of androgenic agent; and ii) an effective amount of an aromatase inhibitor.

Further embodiments are directed to use of a pharmaceutical formulation in methods of reducing mammographic breast density and peri-menopausal symptoms in a patient in need thereof, comprising administering to the patient a subcutaneous pellet comprising: i) an effective amount of androgenic agent; and ii) an effective amount of an aromatase inhibitor.

Further embodiments are directed to use of a pharmaceutical formulation in methods that may be used in pre-menopausal and/or peri-menopausal women for reducing the risk of breast cancer and at substantially the same time not causing perturbations in the hypothalamic-pituitary axis and/or other endocrine axis, for example, adrenal gland and/or ovary gland.

Further embodiments are directed to use of a pharmaceutical formulation in methods of reducing breast stiffness in a patient in need thereof, comprising administering to the patient a subcutaneous pellet comprising: i) an effective amount of an androgenic agent; and ii) an effective amount of an aromatase inhibitor.

Further embodiments are directed to use of a pharmaceutical formulation in methods of reducing breast pain in a patient in need thereof, comprising administering to the patient a subcutaneous pellet comprising: i) an effective amount of an androgenic agent; and ii) an effective amount of an aromatase inhibitor.

Further embodiments are directed to use of a pharmaceutical formulation in methods of decreasing breast elasticity in a patient in need thereof, comprising administering to the patient a subcutaneous pellet comprising: i) an effective amount of an androgenic agent; and ii) an effective amount of an aromatase inhibitor.

Further embodiments are directed to use of a pharmaceutical formulation in methods of decreasing mechano-transduction on the genome of a cell in order to reduce the risk of malignant transformation in a patient in need thereof, comprising administering to the patient a subcutaneous pellet comprising: i) an effective amount of an androgenic agent; and ii) an effective amount of an aromatase inhibitor.

Further embodiments are directed to use of a pharmaceutical formulation in methods of increasing the ratio of fibro-glandular and adipose tissue in a patient in need thereof, comprising administering to the patient a subcutaneous pellet comprising: i) an effective amount of an androgenic agent; and ii) an effective amount of an aromatase inhibitor.

Further embodiments are directed to use of a pharmaceutical formulation in methods of increasing CD36 in a patient in need thereof, comprising administering to the patient a subcutaneous pellet comprising: i) an effective amount of an androgenic agent; and ii) an effective amount of an aromatase inhibitor.

Further embodiments are directed to use of a pharmaceutical formulation in methods of stabilizing and/or an increase in levels of androgen receptor expression in breast tissue of a patient in need thereof, comprising administering to the patient a subcutaneous pellet comprising: i) an effective amount of an androgenic agent; and ii) an effective amount of an aromatase inhibitor.

Further embodiments are directed to use of a pharmaceutical formulation in methods of reducing and/or treating macromastia in a patient in need thereof, comprising administering to the patient a subcutaneous pellet comprising: i) an effective amount of an androgenic agent; and ii) an effective amount of an aromatase inhibitor.

Further embodiments are directed to use of a pharmaceutical formulation in methods of increasing GCDFP15 in a patient in need thereof, comprising administering to the patient a subcutaneous pellet comprising: i) an effective amount of an androgenic agent; and ii) an effective amount of an aromatase inhibitor.

Further embodiments are directed to use of a pharmaceutical formulation in methods of reducing breast pain associated with having a mammography image taken in a patient in need thereof, comprising administering to the patient a subcutaneous pellet comprising: i) an effective amount of an androgenic agent; and ii) an effective amount of an aromatase inhibitor.

Further embodiments are directed to use of a pharmaceutical formulation in methods of increasing mammographic sensitivity in a patient, comprising administering to the patient a subcutaneous pellet comprising: i) an effective amount of an androgenic agent; and ii) an effective amount of an aromatase inhibitor.

Further embodiments are directed to use of a pharmaceutical formulation in methods of reducing ABD % and/or AABD in a patient in need thereof, comprising administering to the patient a subcutaneous pellet comprising: i) an effective amount of an androgenic agent; and ii) an effective amount of an aromatase inhibitor.

Further embodiments are directed to use of a pharmaceutical formulation in methods of reducing BPE in an MRI image of a patient, comprising administering to the patient a subcutaneous pellet comprising: i) an effective amount of an androgenic agent; and ii) an effective amount of an aromatase inhibitor.

Further embodiments are directed to use of a pharmaceutical formulation in methods of reducing the size and/or quantity of cysts in a patient in need thereof, comprising administering to the patient a subcutaneous pellet comprising: i) an effective amount of an androgenic agent; and ii) an effective amount of an aromatase inhibitor.

Additionally, further embodiments are directed to the prophylaxis or treatment of autoimmune inflammatory mastitis in a patient in need thereof.

In particular, in another aspect of the invention there is provided a method for the prophylaxis or treatment of autoimmune inflammatory mastitis in a patient in need thereof, comprising administering to the patient 1) an effective amount of an androgenic agent and 2) an effective amount of an aromatase inhibitor.

In this embodiment, the androgenic agent and the aromatase inhibitor may be administered to the patient in the same pharmaceutical formulation or in separate formulations to one another. Accordingly, the present disclosure extends to all combination treatments of the patient for autoimmune inflammatory mastitis. By combination treatment is meant the androgenic agent and the aromatase inhibitor may be administered together at the same time or sequentially one after the other by the same or different routes whereby the androgenic agent and the aromatase inhibitor exert their respective therapeutic effect in overlapping therapeutic windows, as may be determined by a medical physician or attendant.

Typically, in at least some embodiments as described herein for the treatment of autoimmune inflammatory mastitis, the androgenic agent and the aromatase inhibitor are administered in the same or in different sustained-release pharmaceutical formulations.

In particularly preferred embodiments, the sustained release pharmaceutical formulation(s) are for subcutaneous delivery of the androgenic agent and the aromatase inhibitor to the patient, e.g., in solid-dosage form(s) such as in the form of pellet(s).

Most typically, the androgenic agent and the aromatase inhibitor are provided in the same sustained-release pharmaceutical formulation. The sustained-release formulation can, for example, be a pharmaceutical formulation as described herein for providing a sustained release multi-phasic concentration pattern in the blood of the subject over time as measured by serum concentration for the androgen and plasma concentration for the aromatase inhibitor.

Hence, further embodiments are directed the use of a pharmaceutical formulation in methods of treating autoimmune inflammatory mastitis to a patient in need thereof, comprising administering the pharmaceutical formulation to the patient in the form of a subcutaneous pellet comprising: i) an effective amount of an androgenic agent; and ii) an effective amount of an aromatase inhibitor.

The autoimmune inflammatory mastitis for which the patient is treated in accordance with the present disclosure may, for example, be selected from the group consisting of idiopathic inflammatory macromastia, plasma cell mastitis, granulomatous mastitis, and combinations of the foregoing.

Further embodiments of the present disclosure are therefore directed to the use of a pharmaceutical formulation in methods of treating idiopathic inflammatory macromastia associated with autoimmune disease in a patient in need thereof, comprising administering the pharmaceutical formulation to the patient in the form of a subcutaneous pellet comprising: i) an effective amount of an androgenic agent; and ii) an effective amount of an aromatase inhibitor.

Further embodiments of the present disclosure are directed to the use of a pharmaceutical formulation in methods of treating plasma cell mastitis in a patient in need thereof, comprising administering the pharmaceutical formulation to the patient in the form of a subcutaneous pellet comprising: i) an effective amount of an androgenic agent; and ii) an effective amount of an aromatase inhibitor.

Further embodiments of the present disclosure are directed to the use of a pharmaceutical formulation in methods of treating granulomatous mastitis in a patient in need thereof, comprising administering the pharmaceutical pellet to the patient in a the form of a subcutaneous pellet comprising: i) an effective amount of an androgenic agent; and ii) an effective amount of an aromatase inhibitor.

The present invention further extends to the use of an androgenic agent in the manufacture of a medicament for the prophylaxis or treatment of autoimmune inflammatory mastitis in a patient in need thereof in combination with an effective amount of an aromatase inhibitor.

In yet another embodiment, there is provided the use of an aromatase inhibitor in the manufacture of a medicament for the prophylaxis or treatment of autoimmune inflammatory mastitis in a patient in need thereof in combination with an effective amount of an androgenic agent.

Typically, the androgenic agent administered or included in a pharmaceutical formulation for use in the treatment of autoimmune inflammatory mastitis (AIM) or an AIM condition as described herein is a testosterone, or a pharmaceutically acceptable salt or an ester thereof. The aromatase inhibitor may also be utilised in the form of a pharmaceutically acceptable salt or an ester thereof.

From the above, it will be apparent the instant disclosure expressly extends to methods for the administration of an effective amount of a pharmaceutical formulation as described herein to a subject for purposes and/or treatments as described. Further, in certain embodiments there is provided the use of an androgen and an aromatase inhibitor in the manufacture of a medicament as described herein. The summary provided above is not intended to be limiting as to the embodiments disclosed herein and other embodiments are disclosed in this specification. In addition, limitations of one embodiment may be combined with limitations of other embodiments to form additional embodiments.

Definitions

Terms are used herein are as generally used in the art unless otherwise defined in the following:

The term "absolute area of breast density" (AABD) means the measurement of the surface area of fibro-glandular tissue in a subject's mammogram in square centimeters. For example, this may be measured using CUMULUS software algorithms or visual inspection of a mammogram. Several other tests may be used to measure AABD, including but not limited to, VOLPARA, QUANTRA, and methods taking into account the surface area of fibro-glandular tissue in a mammogram.

The term "androgenic agent" means an agent that increases androgenic activity and/or synthesis. For example, an androgenic agent may be a steroid hormone that binds with high affinity (in the pM or nM range) and specificity to its intracellular mediator, the androgen receptor resulting in receptor conformational change allowing cofactor inclusion, nuclear transportation and/or stimulation of transactivation activity. Thus, regulating the expression of target genes. The androgenic agent may, for example, be an androgen such as an androgen selected from the group consisting of: testosterone, methyltestosterone, and dehydroepiandrosterone. Combinations of these androgenic agents may also be contemplated. In addition to the pharmaceutically acceptable esters of testosterone, esters may include but are not limited to, the enanthate, propionate, cypionate, phenylacetate, acetate, isobutyrate, buciclate, heptanoate, decanoate, undecanoate, caprate and/or isocaprate esters.

The term "area breast density percentage" (ABD %) means the proportion or percentage of fibro-glandular (dense) tissue relative to the total surface area of the breast on a mammogram. For example, this may be measured using CUMULUS software algorithms or visual inspection of a mammogram. Several other tests that may be used to measure ABD %, including but not limited to, VOLPARA, QUANTRA, and methods taking into account the surface area of fibro-glandular tissue in a mammogram.

The term "aromatase inhibitor" means a chemical compound, hormone or polypeptide that blocks and/or inhibits the activity of aromatase, which is an enzyme that converts androgens to estrogens. The aromatase inhibitor may, for example, be selected from the group consisting of: anastrozole, exemestane, and letrozole.

The term "autoimmune inflammatory mastitis (AIM)" means a condition in which non-infective, non-lactational inflammation of breast tissue occurs as the result of autoimmune reaction to elements within the breast tissue.

The term "breast cancer" means a malignant proliferation of epithelial cells lining the ducts or lobules of the breast.

The term "breast elasticity" means a measurement of the pressure required to achieve a given fractional deformation of the breast or a part of the breast. For example, Elasticity=Pressure/Fractional change in radius of the breast, where pressure is measured in, for example, kilo-pascals and fractional change in radius of the breast=(R1−R2)/R1, where R1 is the un-compressed radius and R2 is the compressed radius. Another example may be to directly measure the elasticity of breast tissue by applying shear waves through the breast tissue, for example, using the SuperSonic Imagine Aixplorer™ that uses SuperSonic Imagine's ShearWave™ Elastography.

The term "breast stiffness" means, in its broadest sense, as the measurement of the resistance of a breast to deformation. Factors that may influence the degree of breast stiffness include but is not limited to, physical forces generated by interactions between cells and between cells and the extracellular matrix, the number of cells and the extent of collagen present in the breast, the degree of fluid retention within the breast, the degree of proteoglycan expression and/or combinations thereof. One example of measuring breast stiffness includes the use of the formula force/deformation (dN/cm), where dN denotes deca-Newtons and cm centimetres, wherein the deformation may be determined as the difference between the radius of the mammographic area semicircle and the radius of the volumetric hemisphere, and the compression force is recorded from the mammogram, such as a digital mammogram. For example, under Boyd, et al., the deformation may be determined as the difference R1−R2, where R1 is the un-compressed radius, and R2 is the compressed radius. (Boyd, et al., "Evidence that Breast Tissue Stiffness is Associated with Risk of Breast Cancer" PloS One 2014 Jul. 10; 9(7):e100937)

The term "breast tissue" means the collection of epithelial cells, stromal cells, extracellular matrix, and/or migratory cells, located within and/or in the vicinity of the breast.

The term "effective amount" or "pharmaceutically effective amount" of an agent or compound means a sufficient amount of the agent or compound to provide the desired therapeutic effect and is nontoxic, has an acceptable nontoxic profile and/or an acceptable side effects profile. The amount required may vary from patient to patient, depending, for example, on age, the general condition of the patient, the severity of the condition being treated, the particular agent or compound administered, and/or one or more combinations of these factors. An appropriate "effective amount" typically in an individual case may be determined by one of ordinary skill in the art by reference to the pertinent texts and literature and/or using routine experimentation.

The term "mammographic breast density" or "MBD" means a qualitative estimate of the proportion or percentage of radiopaque, or fibro-glandular ("dense") elements and/or tissue in the breast relative to total breast area (via 2-D determination) or volume (via 3-D determination). Mammographic Breast Density (MBD) may be the qualitative or quantitative estimate of the amount of the fibro-glandular tissue (FGT) within the breast. It may be either the absolute amount of FGT or the relative amount of FGT to the amount of non-FGT (mainly adipose or fat). The absolute amount of FGT may be either estimated as a function of surface area ($cm^2$) (i.e., AABD) or volume ($cm^3$) (i.e. AVBD). The relative amount of FGT may be an estimate of the surface area of FGT relative to non-FGT (as a percentage (i.e. ABD %)) or an estimate of the volume of the FGT to the volume of the breast (i.e., VBD %). Another way may be to determine absolute volumetric breast density (i.e., AVBD) which may be the measured volume of fibro-glandular tissue in a subject's breast in cubic centimeters. Mammographic breast density may be determined by various methods, including but not limited to, mammography, digital mammography, magnetic resonance imaging (MRI), ultrasound, digital breast tomosynthesis (DBT), virtual touch tissue imaging quantification (VTIQ), and combinations thereof. MBD may be qualitatively assessed, via 2-D determinations and/or using the BI-RADS® density categories, with 1 (or a) being least dense and 4 (or d) being the densest. MBD may also be qualitatively and/or quantitatively assessed via 3-D determinations and/or using volumetric measurements of the breast, such as determining the volumetric breast density, which is the proportion of fibro-glandular (dense) tissue relative to the total volume of tissue in the breast (e.g., fibro-glandular (dense) tissue and fat in the breast). Another way is to determine absolute volumetric breast density (AVBD), which is the measured volume of fibro-glandular tissue in a subject's breast in cubic centimeters. Assessments of MBD via 3-D determinations may also account for the heterogeneity of dense tissue within the breast. Several tests that may be used to measure MBD, including but not limited to, VOLPARA, QUANTRA, CUMULUS, and methods taking into account the volume of fibro-glandular tissue ($cm^3$).

The term "patient" or "subject" means an animal, including the human species that is treatable with the compositions, methods, and kits of the present disclosure. The term "patient" or "patients" is intended to refer to both the male and female gender unless one gender is specifically indicated or clear from the context. The term "patient" may also refer to a female to male transgender.

The term "peri-menopause" or "menopausal transition" means the period of time around menopause during which a woman's body makes its natural transition toward permanent infertility (menopause). Women may start peri-menopause at different ages, and may notice signs of progression toward menopause, such as menstrual irregularity, during their 40's, or even as early as their mid-30's. During peri-menopause, estrogen levels may rise and fall unevenly, menstrual cycles may lengthen or shorten, and menstrual cycles may begin in which the ovaries do not release an egg (ovulate). During peri-menopause, other menopause-like symptoms may be experienced, including, but not limited to, hot flashes, sleep problems, and/or vaginal dryness.

The term "peri-menopausal symptoms" is understood to include but is not limited to, menstrual irregularity; hot flashes and sleep problems; mood changes; mood swings; irritability; depression; vaginal dryness; urinary or vaginal infections; urinary incontinence; decreasing fertility; changes in sexual arousal or desire; bone loss; fragile bones; osteoporosis; or changing cholesterol levels, such as an increase in low-density lipoprotein (LDL) cholesterol, or a decrease in high-density lipoprotein (HDL) cholesterol and combinations thereof.

The term "pharmaceutically acceptable" means those compounds, agents, materials, compositions, excipients, and/or dosage forms that are, within the scope of sound medical judgment, suitable for contact with the tissues of human beings and/or animals without excessive toxicity, irritation, allergic response, or other problems or complications commensurate with a reasonable benefit and/or risk ratio.

The term "pellet" means a solid formulation implant comprising an effective amount of an androgen and an effective amount of an aromatase inhibitor. The pellet or implant may have different suitable shapes and sizes, for example, spherical, cylindrical, rectangular, square or combinations thereof. It may have angular edges or round edges. In certain embodiments, the pellet or implant may be compressed.

The term "pharmaceutical formulation" means a formulation comprising an effective amount of an androgen and an effective amount of an aromatase inhibitor when the formulation is administered to a warm-blood subject the formulation provides a sustained release multi-phasic concentration pattern in the blood of the subject over time as measured by serum concentration for the androgen and plasma concentration for the aromatase inhibitor. There may be at least 2, 3 or 4 different time periods. These time periods vary depending on one or more of the following: formulation, delivery system, drug concentrations, and individual physiological variabilities during the time to complete, or substantially complete, formulation absorption. Typically, the formulation's absorption is not less than 3 months and not more than 5 months. In certain embodiments, the formulation may be delivered via a transdermal patch. In certain embodiments, the formulation may be delivered via a solid form such as a subcutaneous pellet. In certain embodiments, the formulation may be delivered via a solid form such as a compressed subcutaneous pellet.

The term "post-menopausal woman" is understood to include not only a woman of advanced age who has passed through menopause but also a woman who has had her ovaries removed or destroyed by other means or for some other reason has suppressed estrogen production, such as one who has undergone long-term administration of corticosteroids, suffer from Cushing's syndrome or has gonadal dysgenesis.

The term "subject" is an animal including the human species that is treatable with the compositions, methods, and kits of the present disclosure. The term "subject" or "subjects" is intended to refer to both the male and female gender unless one gender is specifically indicated or clear from the context. The term "subject" may also refer to a female to male transgender.

The term "treatment" or "therapy" as used herein includes preventative (e.g., prophylactic) treatment and/or palliative treatment and "treating" as used herein refers to the act of providing preventative and/or palliative treatment.

The term "volumetric breast density percentage (VBD %)" means the proportion or percentage of fibro-glandular (dense) tissue in volume relative to the total volume of tissue in the breast. For example, this may be measured using the Volpara Solution™ software algorithms. In the Volpara Solution™ software algorithms, VBD % is referred to as volumetric breast density percentage. There are several other tests that may be used to measure VBD %, including but not limited to, QUANTRA, CUMULUS, and methods taking into account the volume of fibro-glandular tissue.

BRIEF DESCRIPTION OF THE DRAWINGS

For a better understanding of the disclosure, and to show more clearly how it may be carried into effect according to one or more embodiments thereof, reference will now be made, by way of example, to the accompanying figures.

provides a sustained release concentration pattern in the blood of the subject over time as measured by serum concentration for the testosterone or an ester thereof, and plasma concentration for the aromatase inhibitor.

FIGS. 7A-B illustrate the anastrozole absorption rates, according to certain embodiments.

FIG. 19A are mammographic images before (left) and after (right) treatment in accordance with the present disclosure showing a substantial reduction in breast size and density.

FIG. 19B are Volpara Solution™ breast volume and density measurements (left) and after (right) treatment for the patient of FIG. 19A showing a breast volume reduction (58%) back to pre-morbid size and fibro-glandular tissue reduction (71%).

FIG. 19C are magnetic resonance images (MRI) of the breast of the patient of FIG. 19 before treatment (left) and after treatment for three subsequent years showing a reversal of the extreme background parenchymal enhancement on MRI for the subsequent 3 year period following treatment cessation.

FIG. 20A are mammographic images for another patient before (left) and after (right) treatment in accordance with the present disclosure showing a substantial reduction in breast size and density.

FIG. 20B are Volpara Solution™ breast volume and density measurements before (left) and after (right) treatment for the patient of FIG. 20A showing a breast volume reduction (10%) back to pre-morbid size and a reduction in fibro-glandular volume (41%).

FIG. 21A shows mammographic images for another patient before (left) and after (right) treatment in accordance with the present disclosure showing a substantial reduction in breast size and density.

FIG. 21B are Volpara Solution™ breast volume and density measurements before (left) and after (right) treatment for the patient of FIG. 21A showing a breast volume reduction (32%) back to pre-morbid size and a reduction in fibro-glandular volume (52%).

FIG. 22A are magnetic resonance images (MRI) of the breast of further patient before treatment (left) and after treatment (right) in accordance with the present disclosure showing a complete reversal of MRI extreme background parenchymal enhancement.

FIG. 22B are mammographic images before (left) and after (right) of the breast of the patient of FIG. 22B showing a reduction in breast size and density.

FIG. 22C are Volpara Solution™ breast volume and density measurements before (left) and after (right) treatment for the patient of FIG. 22B showing a breast volume reduction (23%) back to pre-morbid size and a reduction in fibro-glandular volume (36%).

Figure 1:
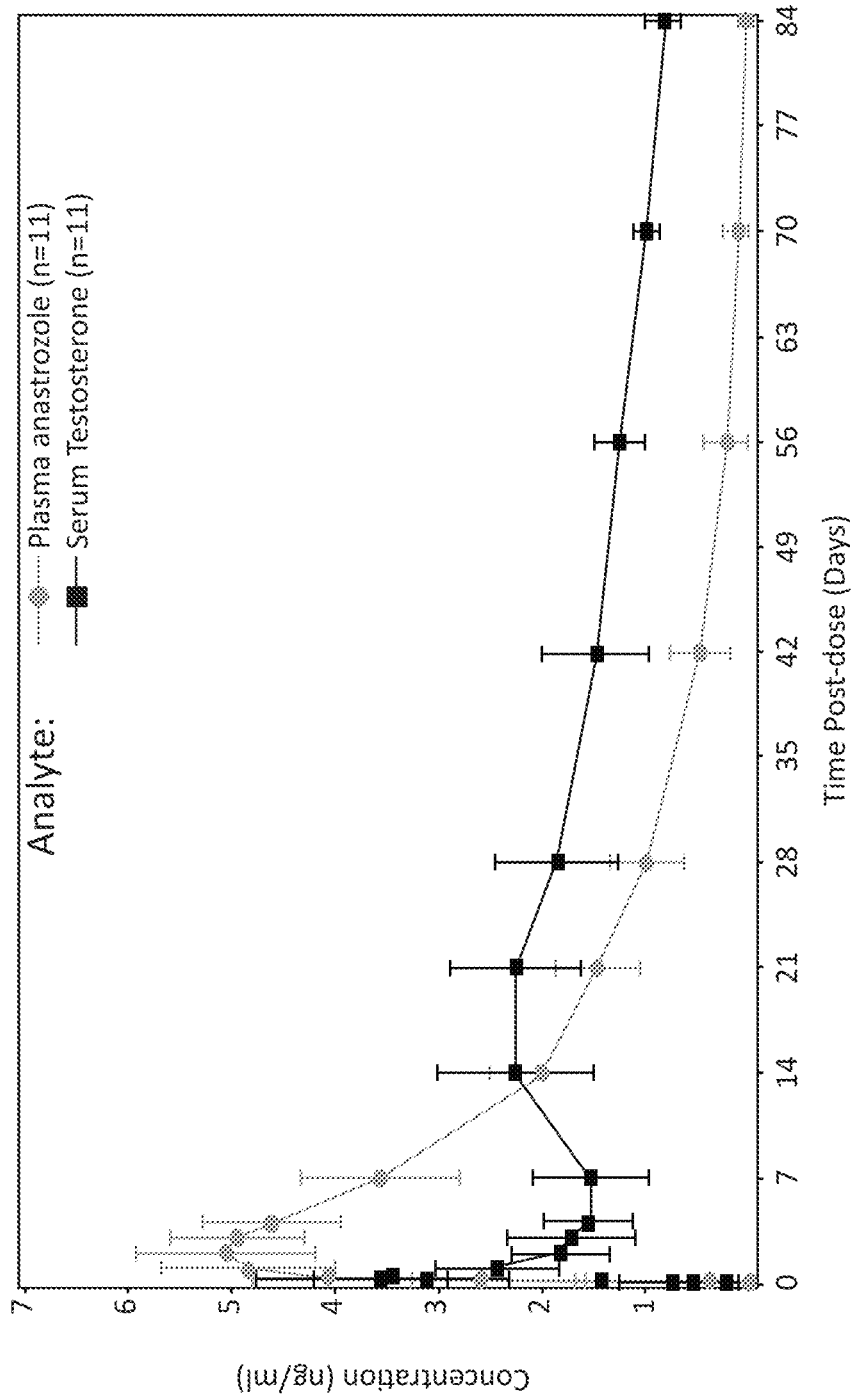
FIG. 1 shows the data of the serum concentration for the androgen and plasma concentration for the aromatase inhibitor over 84 days, according to certain exemplary embodiments.

It will be apparent to one skilled in the art, in view of the following detailed description and the claims appended hereto, that various substitutions and/or modifications may be made to the present disclosure without departing from the scope of the inventions as claimed.

DETAILED DESCRIPTION OF EXEMPLARY EMBODIMENTS

The following description is provided in relation to several embodiments that may share common characteristics and features. It is to be understood that one or more features of one embodiment may be combined with one or more features of other embodiments. In addition, a single feature or combination of features in certain of the embodiments may constitute additional embodiments. Specific structural and functional details disclosed herein are not to be interpreted as limiting, but merely as a representative basis for teaching one skilled in the art to variously employ the disclosed embodiments and variations of those embodiments.

The subject headings used in the detailed description are included only for the ease of reference of the reader and should not be used to limit the subject matter found throughout the disclosure or the claims. The subject headings should not be used in construing the scope of the claims or the claim limitations.

The present disclosure is directed, at least in part, to providing drug delivery systems with a multi-phasic sustained release pattern comprising an androgenic agent and an aromatase inhibitor in a compressed pellet that unexpectedly overcomes the problem of obtaining high intra-tissue DHT to oestradiol ratio when subcutaneously delivered to a subject. The desired effect is to have an early peak of serum testosterone which is rapidly blocked by a high level of aromatase inhibitor allowing the induction of 5 alpha reductase conversion of testosterone to DHT. Then it is desirable to have a rapid reduction of the aromatase inhibitor to ensure that there is not a blockade, or substantially blockage, globally of oestradiol production and symptomatic lowering of oestradiol level in the serum. The alteration of the axis towards a high DHT to oestradiol level in tissues where there is overexpression of aromatase may be achieved with the utilisation of certain exemplary embodiments that exhibit this multi-phasic sustain release pattern.

There are several examples of overexpression of aromatase resulting in disease processes where woman and men may benefit from this testosterone and an aromatase inhibitor combination. Therefore, within these tissues, when there may be overexpression of the aromatase enzyme and the coexpression of the 5 alpha reductase enzyme this enzymatic combination may be pharmacologically manipulated to bring about an orderly transition towards alteration in DHT/oestradiol ratio. These disease conditions include but not exclusively, high mammographic breast density, breast pain, endometriosis, male gynaecomastia, perimenopausal and premenstrual tissue aberrations, autoimmune inflammatory mastitis (which includes conditions such as idiopathic inflammatory macromastia, plasma cell mastitis, and granulomatous mastitis).

Figure 2:
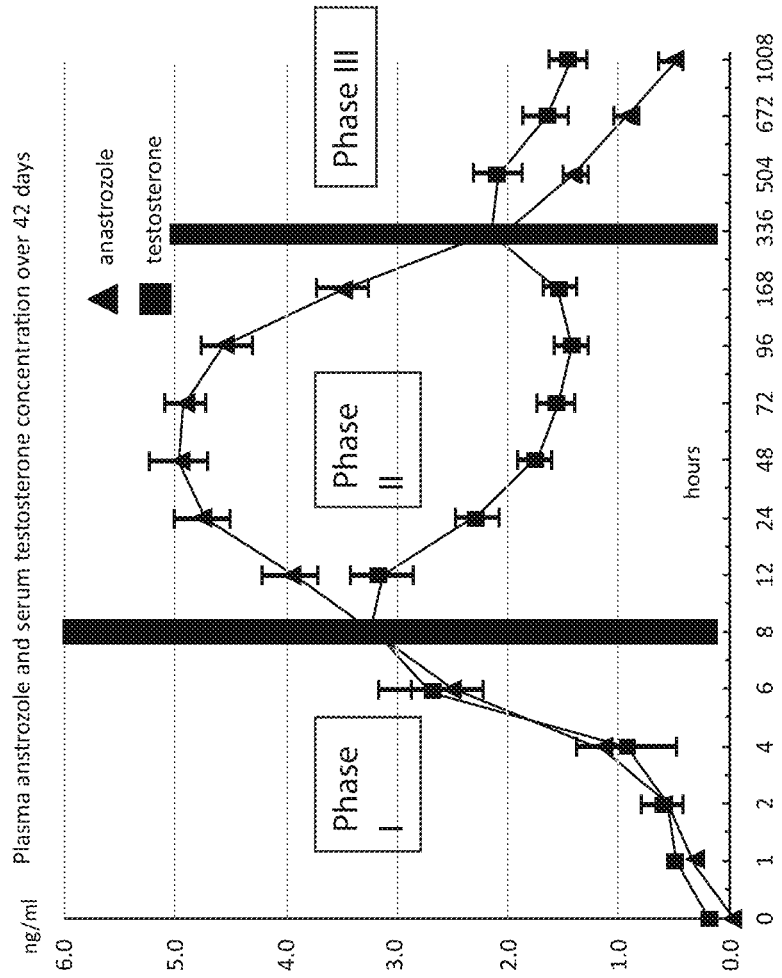
FIG. 2 shows the data of FIG. 1 but expanded to further illustrate the first 42 days.
Figure 3:
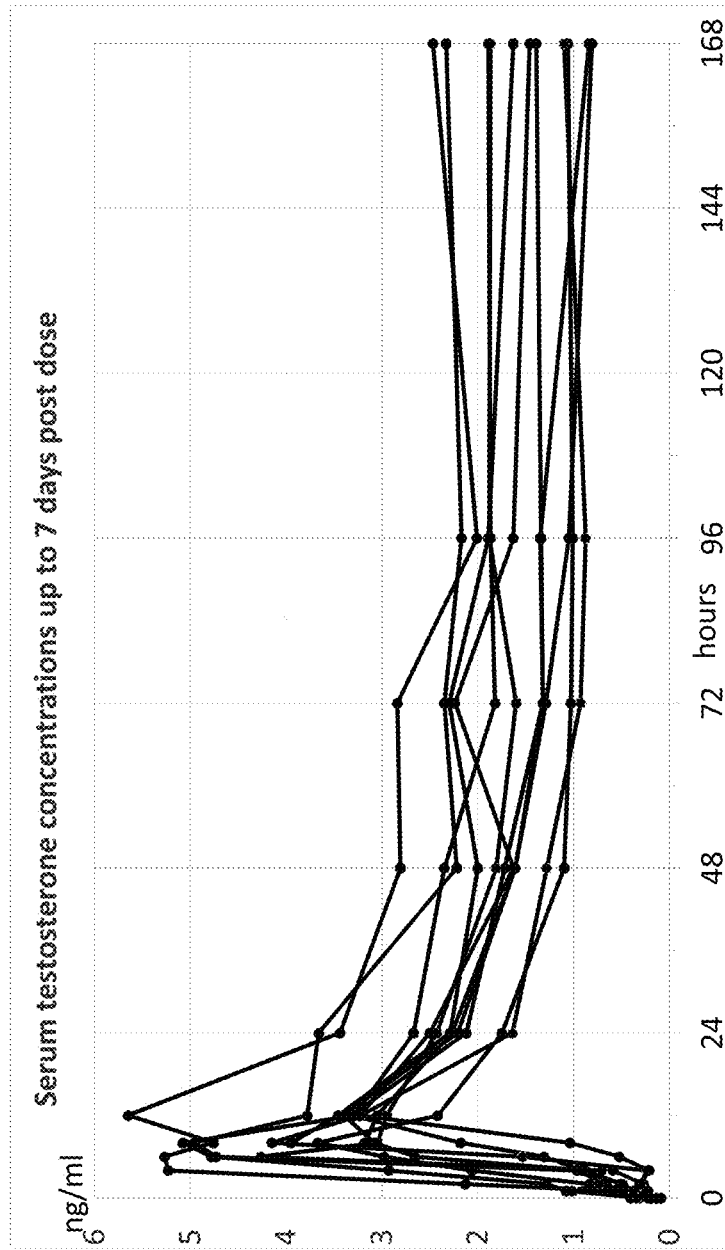
FIG. 3 shows the serum concentration of testosterone in 11 subjects up to 7 days post dose, according to certain exemplary embodiments.
Figure 4:
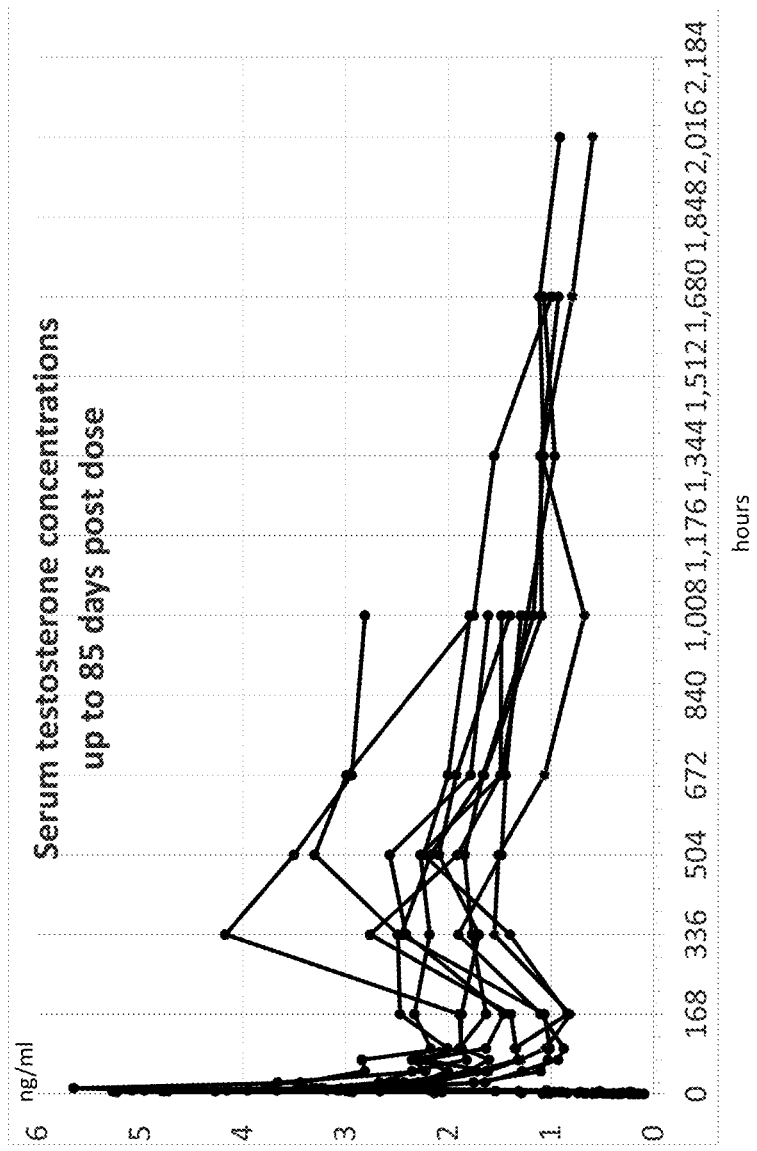
FIG. 4 shows the serum concentration of testosterone in 11 subjects up to 85 days post dose, according to certain exemplary embodiments.
Figure 5:
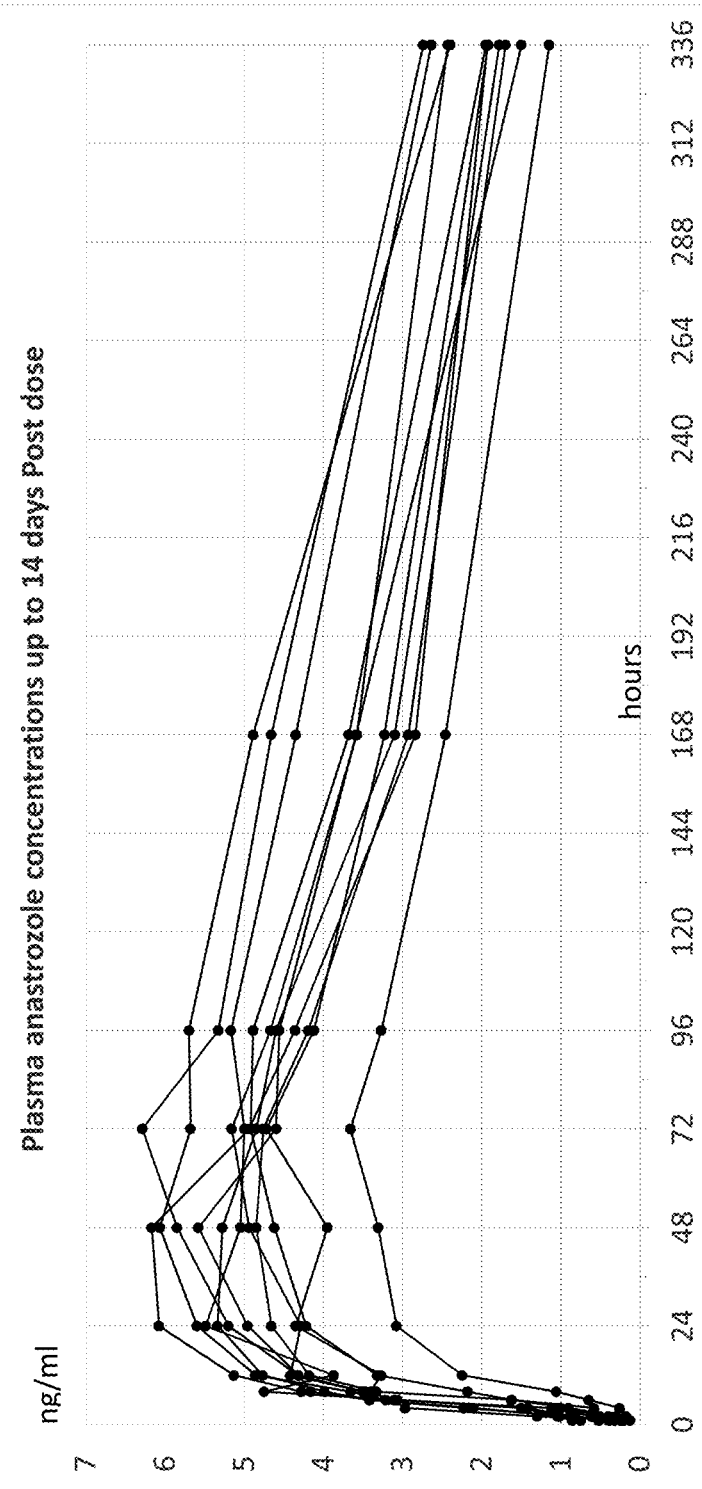
FIG. 5 shows the plasma concentration of anastrozole in 11 subjects over 336 hours post dose, according to certain exemplary embodiments.
Figure 6:
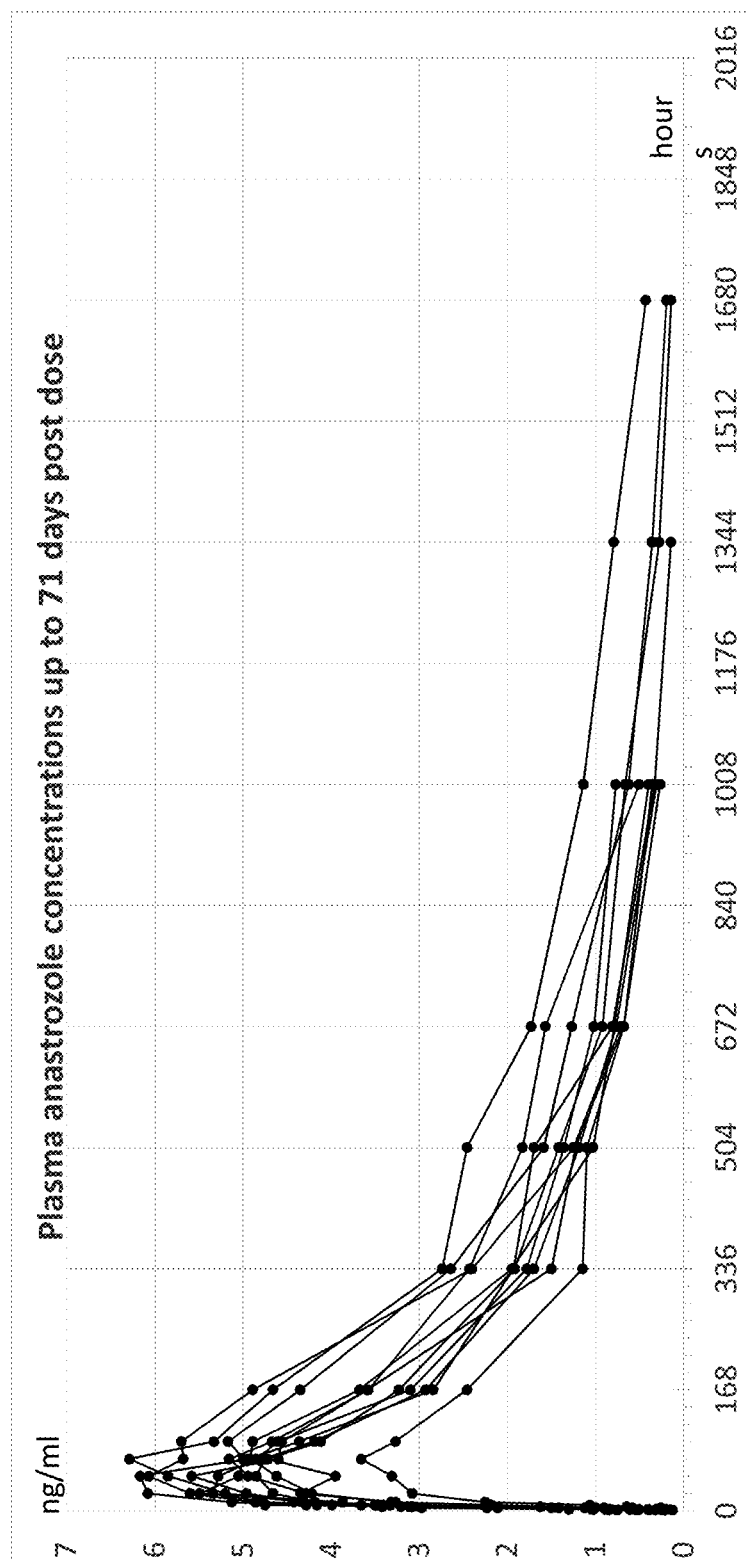
FIG. 6 shows the plasma concentration of anastrozole in 11 subjects over 1680 hours post dose, according to certain exemplary embodiments.

FIG. 2 illustrates an exemplary of a combination of testosterone and aromatase inhibitor and the impact this pattern has on several subjects (N=11) that have been administered a subcutaneous pellet regime.

In this exemplary, phase I shows a rapid increase in both serum testosterone and plasma anastrozole in the subjects. This increase results in a rapid tissue induction of five alpha reductase and the profound inhibition of aromatase. The high tissue level of testosterone is rapidly converted to DHT with conversion to oestradiol being completely blocked, or substantially blocked. In this example, this first phase lasts for approximately 8 days as illustrated by the vertical bar separating phase 1 from phase 2. The time period for phase 1 may vary depending on a number of factors, including, but not limited to, the biology of a particular subject, the formulation of the pellet and/or the manufacturing parameters used for making the pellet.

In the exemplary, the phase II time period lasts for approximately 14 days. In phase 2 it is desirable to recondition the enzymatic system to cause a sustained high intra-tissue level of anastrozole that continues to allow the induction of 5 alpha reductase to work unopposed, or substantially unopposed, to aromatase conversion of testosterone and oestradiol. This reconditioning leads to a fall in serum testosterone avoiding excessive androgenic side-effects and persistent adduction of five alpha reductase. In this example, this second phase lasts for approximately 14 days as illustrated by the vertical bar separating phase 2 from phase 3. The time period for phase 2 may vary depending on a number of factors, including, but not limited to, the biology of a particular subject, the formulation of the pellet and/or the manufacturing parameters used for making the pellet.

In this exemplary, phase III the anastrozole level falls rapidly allowing some conversion of testosterone to oestradiol and avoiding significant usage and depletion symptoms which may result from sustained high levels of anastrozole which would be observed, for example, in a zero-order release pattern. During this time the induced 5 alpha reductase continues to convert the elevated testosterone to DHT within the target tissue until the implant runs out of the substrate and is replaced. In this example, this third phase lasts at least until the pellet is depleted. As shown in FIG. 1 in this example the subjects were tracks for another 70 days. The time period for phase 3 may vary depending on a number of factors, including, but not limited to, the biology of a particular subject, the formulation of the pellet and/or the manufacturing parameters used for making the pellet.

Certain embodiments may be used for treating extreme mammographic breast density. Serum reproductive hormone levels poorly correlate with intra-tissue levels due to significant metabolism to either inactive or active metabolites of prohormones such as testosterone. In certain disease states such as extreme mammographic breast density, there is overexpression of enzymes known to convert testosterone to either estrogen or dihydrotestosterone-10 times more potent as an androgen than testosterone. By altering the androgen to estrogen ratio in high mammographic breast density that there is the potential for reduction of that density and therefore reduce the incidence of breast cancer. The reduction in density is also applicable to situations such as gynecomastia in men where there is an excessive estrogen to androgen within the tissue. To facilitate the alteration in androgen to estrogen ratio, a subcutaneous pellet has been designed to facilitate a multi-phasic sustained release pattern. When anastrozole and testosterone are combined in a specific fashion and compression into a pellet that has undergone specific compression the resultant pharmacokinetics of facilitates this multi-phasic sustained release of both active ingredients. Again, as discussed elsewhere, it is desirable that there is an early increased of anastrozole to obtain the minimal concentration required to facilitate the blockade, or substantial blockage, of aromatase within the tissue expressing high levels of aromatase at approximately the time as peak testosterone levels are delivered to that tissue. The early increased of anastrozole facilitates the conversion of testosterone through five alpha reduction to dihydrotestosterone and facilitates an androgenic excess over estrogenic environment. Once this initial high levels of anastrozole are obtained a significantly low level is maintained so as to not cause alterations in either hypothalamic-pituitary function or induction of total body aromatase inhibition as is seen in higher concentrations of aromatase inhibitors such as when they are taken orally. This then allows slow of testosterone into the tissues in which there has been an induction of the five-alpha reductase in the somatic system to continue the perturbation of the antigenic environment. This unique multi-phasic sustained release pattern is useful to establish alteration in tissue hormone levels without causing significant physiological alterations in other serum reproductive hormone levels and the resultant potential for adverse side-effects.

Certain embodiments may be used for treating one or more of the following: high breast density and breast stiffness. High breast density and/or breast stiffness is not normal, rather it is pathological; and it is something which may be addressed by effective amounts of an androgenic agent and/or an effective amount of an aromatase inhibitor rather than being treated as a lifestyle modification (e.g., diet and exercise) which has not proven to be successful in pre-menopausal, peri-menopausal and/or post-menopausal women.

Certain embodiments are directed to pharmaceutical formulations that may be used in methods for providing an individualized reduction of one or more of the following: mammographic breast density and breast stiffness in a patient in need thereof, comprising (i) determining the patient's MBD and/or breast stiffness; (ii) optionally, measuring the patient's free androgenic index and/or alterations in the patient's free androgenic index over a period of time of at least one month; (iii) determining adjusted doses of an androgenic agent and aromatase inhibitor taking into account the patient's body weight, total body fat, MBD, age, and free androgenic index; and (iv) administering the adjusted dose to said patient. In certain embodiments, the measuring the patient's free androgenic index and/or alterations in the patient's free androgenic index over a period of time of at least one month may include taking a blood sample and measuring the amount of free androgenic agent (or testosterone) in the patient's serum.

Certain embodiments are directed to pharmaceutical formulations may be used in methods for providing an individualized reduction of one or more of the following: VBD %, AVBD and breast stiffness in a patient in need thereof, comprising (i) determining the patient's VBD % and/or AVBD and/or breast stiffness; (ii) optionally, measuring the patient's free androgenic index and/or alterations in the patient's free androgenic index over a period of time of at least one month; (iii) determining adjusted doses of an androgenic agent and/or aromatase inhibitor taking into account the patient's body weight, total body fat, VBD % and/or AVBD, age, and free androgenic index; and (iv) administering the adjusted dose to said patient. In certain embodiments, the measuring the patient's free androgenic index and/or alterations in the patient's free androgenic index over a period of time of at least one month may include taking a blood sample and measuring the amount of free androgenic agent (or testosterone) in the patient's serum.

Certain embodiments are directed to pharmaceutical formulations may be used in methods for providing an individualized reduction of one or more of the following: ABD %, AABD, and breast stiffness in a patient in need thereof, comprising (i) determining the patient's VBD % and/or AVBD and/or breast stiffness; (ii) optionally, measuring the patient's free androgenic index and/or alterations in the patient's free androgenic index over a period of time of at least one month; (iii) determining adjusted doses of an androgenic agent and/or aromatase inhibitor taking into account the patient's body weight, total body fat, ABD % and/or AABD, age, and free androgenic index; and (iv) administering the adjusted dose to said patient. In certain embodiments, the measuring the patient's free androgenic index and/or alterations in the patient's free androgenic index over a period of time of at least one month may include taking a blood sample and measuring the amount of free androgenic agent (or testosterone) in the patient's serum.

Certain embodiments are directed to pharmaceutical formulations may be used for reducing one or more of the following: mammographic breast density and breast stiffness in a patient in need thereof, wherein the pharmaceutical formulation increases sensitivity of breast imaging detections by mammography, digital mammography, magnetic resonance imaging (MRI), ultrasound, digital breast tomosynthesis (DBT), virtual touch tissue imaging quantification (VTIQ), or combinations thereof.

Certain embodiments are directed to pharmaceutical formulations may be used for reducing one or more of the following: mammographic breast density and breast stiffness in a patient in need thereof, wherein the pharmaceutical formulation increases detection of breast cancer developing in the patient.

Certain embodiments are directed to pharmaceutical formulations may be used for reducing one or more of the following: VBD %, AVBD, and breast stiffness in a patient in need thereof, wherein the pharmaceutical formulation increases detection of breast cancer developing in the patient.

Certain embodiments are directed to pharmaceutical formulations may be used for reducing one or more of the following: ABD %, AABD, and breast stiffness in a patient in need thereof, wherein the pharmaceutical formulation increases detection of breast cancer developing in the patient.

Pharmaceutical formulations as disclosed herein may be used to affect one or more of the following in a patient: reducing mammographic breast density; treating mammographic breast density; reducing breast stiffness; treating breast stiffness; reducing mammographic breast density in a patient having a breast with a mammographic breast density of 7.5% or greater; reducing mammographic breast density in a patient having a breast with a BI-RADS® score of 3 or 4 (or c or d); inducing breast involution in a patient; inducing net cell death over proliferation in a breast of a patient; inducing net extracellular matrix degradation over development of extracellular matrix in a breast of a patient; methods of reversing cell number and mammographic breast density in a breast of a peri-menopausal patient; reducing mammographic breast density and peri-menopausal symptoms in a patient, and prophylaxis or treatment of autoimmune inflammatory mastitis (e.g., idiopathic inflammatory macromastia, plasma cell mastitis, granulomatous mastitis, and combinations of the foregoing).

These pharmaceutical formulations and combination treatments of an androgenic agent and an aromatase inhibitor (Ai) as described herein may be useful in pre-menopausal, peri-menopausal woman, and/or post-menopausal woman.

For example, high breast density in peri-menopause woman is known as a risk for developing breast cancer. The dense tissue in peri-menopausal women is not considered normal and has pathological implications. This increase in breast density may be due to lifelong exposure to high levels of estrogen and progesterone in the presence of a low testosterone environment. The present inventors have discovered, among other things, that pre-menopausal, peri-menopausal and/or post-menopausal woman who receive via a multi-phasic pattern formulation an effective amount of an androgenic agent such as testosterone and an effective amount of an aromatase inhibitor (such as anastrozole) may show a reduction in breast density and/or breast stiffness. The present inventors have also discovered that pre-menopausal, peri-menopausal and/or post-menopausal woman who receive via a multi-phasic pattern formulation an effective amount of testosterone and an effective amount of an aromatase inhibitor (such as anastrozole) may show induction of breast involution and/or net cell death over proliferation. The present inventors have also discovered that an effective amount of an aromatase inhibitor delivered to a subject via a multi-phasic pattern formulation to the subject's breast tissue may be used to stop the conversion of testosterone to estrogen and thus allow testosterone to invoke an involution of the breast cells.

Certain further embodiments are directed to the prophylaxis or treatment of autoimmune inflammatory mastitis (AIM), which includes the conditions of idiopathic inflammatory macromastia, plasma cell mastitis and granulomatous mastitis as described above.

Breast tissue may be a target tissue in autoimmune diseases, this process being favoured by the hormonal milieu (Touraine, 2005). Autoimmune breast tissue, compared to normal breast tissue, has been demonstrated to have elevated aromatase (that converts androgens to estradiol) and other factors associated with inflammation, such as IGF2, EGFR, TGF-β, PDGFR-α and β (Das, 2019).

The breast is unique in that it requires an immunoprivilaged environment for lactation and a rapid remodelling of tissue following lactation (called lactational involution) that requires immunosuppression to avoid autoimmunity (Dawson, 2020). Central to this is the formation of regulatory T (Treg) cells that are able to inhibit proliferation and cytokine production in effector T cells and play a major role in immune responses and prevention of autoimmune disease. During T cell development, T cell receptor (TCR) gene segments are rearranged to generate a diverse TCR repertoire necessary for immunity to invading pathogens. An unintended consequence of this diversity is the recognition of self-antigen, which can result in autoimmunity. For T cells, two fundamental processes promote tolerance to self in the thymus (referred to as central tolerance) prior to their release into the periphery: (1) negative selection, whereby autoreactive T cells are eliminated; and (2) generation of $CD4^+$ forkhead box P3 $(Foxp3)^+$ regulatory T (Treg) cells. Central to the process is that CD36 facilitates transfer of cell-surface antigens to promote tolerance to host antigens during homeostatis. A master regulator of Treg cell development and function is transcription factor Foxp3. Testosterone treatment induces a strong increase in the Treg cell population both in vivo and in vitro (Walecki, 2015). High levels of Treg cells in breast tumours have reduced the capacity of immunotherapies due to Treg cell immunosuppressive capacity. Targeting Treg cells has resulted in unacceptable autoimmunity side-effects that limits the use of this pathway. The impact of testosterone and an aromatase inhibitor on breast tissue immunoreactivity is diagrammatically illustrated in FIG. 17

The manifestation of AIM is associated with dense stromal replacement of breast adipose tissue clearly demonstrated by MRI of the breasts in those affected by this disease (Touraine, 2005). One of the main factors in this inflammatory cascade is a member of the Class B scavenger receptor family of cell surface proteins, CD36. CD36 is found on platelets, erythrocytes, monocytes, differentiated adipocytes, skeletal muscle, mammary epithelial cells, spleen cells and some skin microdermal endothelial cells. It has been demonstrated that a) CD36 is downregulated by estradiol control in hormonally sensitive breast cancer cell lines (Uray, 2004); b) overexpression of CD36 in fibroblasts inhibits the formation of solid tumors in subtypes of breast cancer models (Cheng, 2020); and c) CD36 is profoundly suppressed in non-malignant tissue of women at higher risk of developing breast cancer due to high mammographic density (HMD) (i.e., low fat containing breast tissue) (De-Filippis, 2014).

Thea Tlsty's group (DeFilipis, 2014) has suggest the following cascade: i) elevated basal DNA damage in HMD epithelial cells results in increased activin A secretion; ii) activin A binds to its receptor on adjacent fibroblasts and activates the MAPK pathway; iii) MAPK pathway activation results in PPARγ phosphorylation and inhibition; iv) PPARγ inhibition leads to decreased CD36 transcription and subsequently, the induction of the desmoplastic-like phenotypes observed in HMD tissues.

As described herein, induction of CD36 expression in breast tissue may be obtained by treating the tissue with an effective amount of an androgenic agent in combination with an effective amount of an aromatase inhibitor, and the present disclosure expressly extends to such methods and use in a patient e.g., a peri-menopausal, menopausal or post-menopausal woman.

Figure 17:
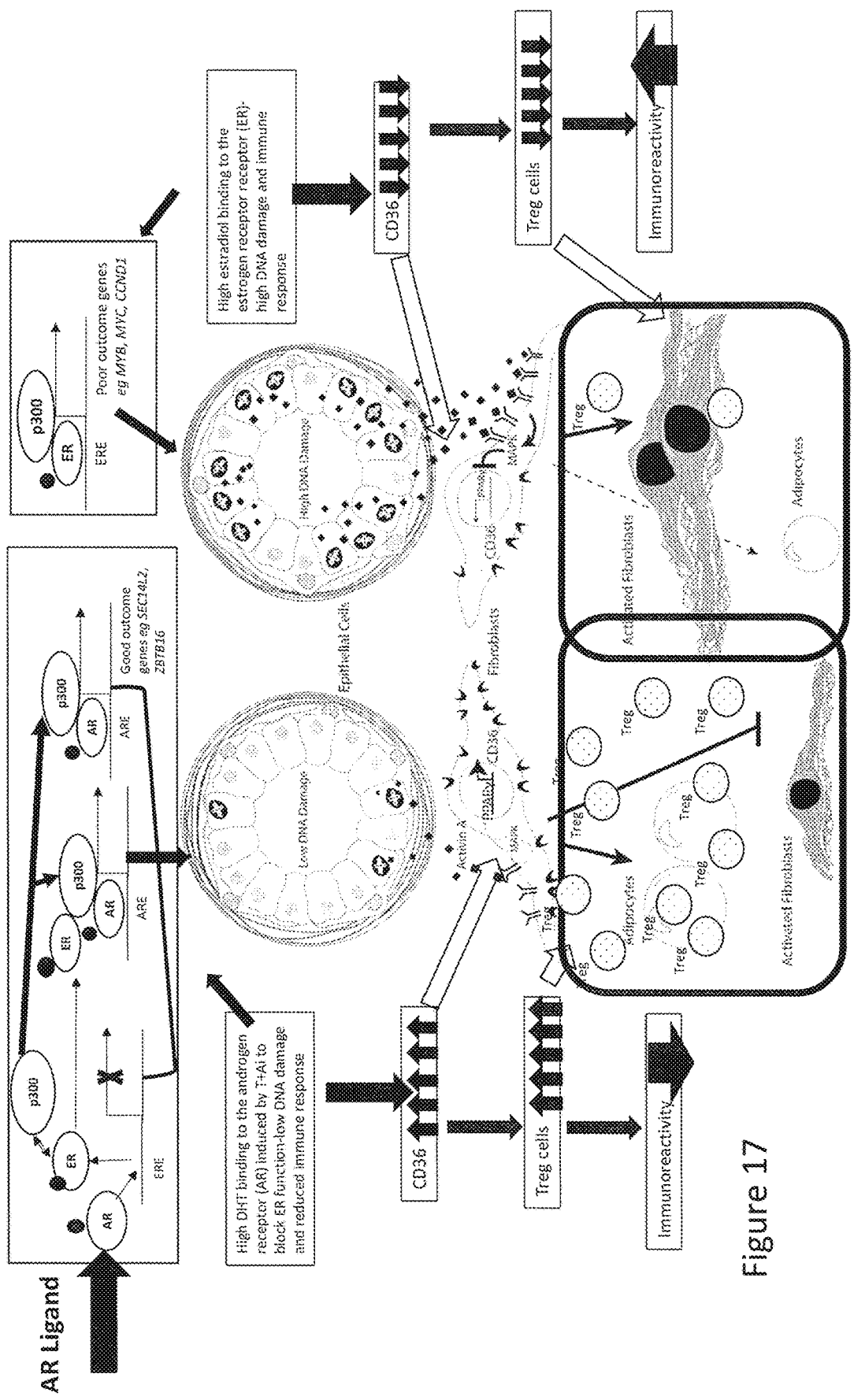
FIG. 17 diagrammatically illustrates the effect of the androgenic agent testosterone and the aromatase inhibitor (T+Ai) on breast tissue immunoreactivity.
Figure 18:
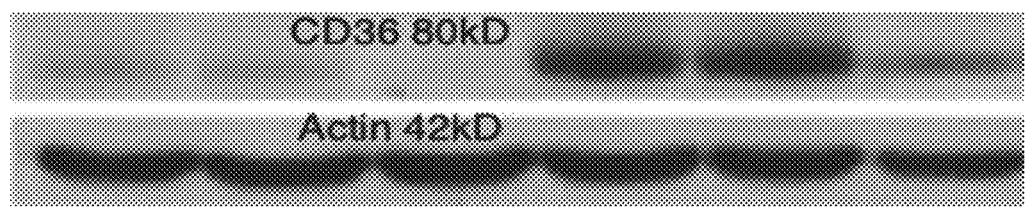
FIG. 18 shows the results of western blot analysis of CD36 protein in three explant samples of normal breast tissue obtained from three peri-menopausal women at baseline and after 24 hours cultivation.

A subcutaneous pellet is described herein for facilitating a multi-phasic sustained release pattern for alteration in androgen to estrogen ratio in the prophylaxis or treatment of autoimmune diseases or conditions. Anastrozole and testosterone can be combined and compressed into a pellet as described herein to provide pharmacokinetics facilitating this multi-phasic sustained release of both active ingredients. This release pattern ensures that early high levels of testosterone are associated with very high levels of aromatase inhibitor, so only DHT is presented to the inflamed breast tissue and that the testosterone is not converted to estradiol (which is pro-inflammatory). In the second phase, after the peak of the testosterone level is reached, the induction of 5 alpha reductase from the first phase continues to ensure maintenance of high levels of DHT to exert an anti-inflammatory effect, whilst there is a more rapid decline in anastrozole. Continued high levels of anastrozole could lead to adverse events due to an excessive drop in estradiol systemically, however this risk is reduced by the rapid reduction in anastrozole delivery. The third delivery phase then allows slow release of testosterone into the tissues in which there has been an induction of the five-alpha reductase in the somatic system to continue the perturbation of the antigenic environment. This unique multi-phasic sustained release pattern may establish alteration in tissue hormone levels substantially without causing significant physiological alterations in other serum reproductive hormone levels and the resultant potential for adverse side-effects. The impact of the androgen testosterone and the aromatase inhibitor is anastrozole as described herein on breast tissue immunoreactivity is illustrated in FIG. 17.

One of the advantages found in one or more of the disclosed compositions, delivery systems and/or methods of use is the rapid early induction of conversion of testosterone to dihydrotestosterone in the tissue where an early response may reset the homeostatic mechanism in a beneficial way and reduce the estradiol to androgen ratio in the tissue. This may result in one or more of the following advantages:

A. Enhanced mammographic detection due to reduced breast density enabling the mammogram to visualize malignancy at an earlier and/or less aggressive stage.
B. Reduced risk of interval breast cancer, such as those that may occur between mammographic screening rounds. These cancers are common in breasts with high MBD.
C. Reduction in breast stiffness.
D. Reduced pain during mammographic breast compression.
E. Ability to achieve better mammographic compression due at least in part to reduced pain.
F. Because better mammographic compression is achieved and that the breast tissue is less dense the amount of energy required to expose the image on the mammogram is therefore reduced thus reducing the radiation of the breast tissue. Reducing the risk of radiation induced breast cancer.
G. Ability to achieve better patient compliance in having regular mammographic check-ups.
H. Ability to treat patient and at the same time not causing perturbations in the hypothalamic-pituitary axis and/or other endocrine axis.
I. Reduced breast pain in a patient.
J. Reduced breast elasticity in a patient.
K. Decreased mechano-transduction on the genome of a cell in order to reduce the risk of malignant transformation in a patient.
L. Increased the ratio of fibro-glandular and adipose tissue in a patient.
M. Increased CD36 in a patient.
N. Stabilization and/or an increase in levels of androgen receptor expression in the breast tissue of a patient.
O. Treatment of macromastia in a patient.
P. Increased GCDFP15 in a patient.
Q. Reduced BPE in an MRI image of a patient.
R. Reduction in the size and/or quantity of cysts in a patient.
S. Reduce the risk of breast cancer.
T. Treatment of autoimmune inflammatory mastitis (AIM) (which includes e.g., the conditions of idiopathic inflammatory macromastia, plasma cell mastitis and granulomatous mastitis).

There are a number of categories used by diagnosticians and physicians to characterize the type and/or degree of mammographic breast density of a breast of a patient.

A diagnosing or treating physician may use one or more exams/tests to evaluate, characterize, and/or diagnose, a breast density, including but not limited to, mammography, digital mammography, magnetic resonance imagery (MRI), ultrasound, digital breast tomosynthesis (DBT), virtual touch tissue imaging quantification (VTIQ), or combinations thereof. The physician may also use other indicia, such as medical history or family history (to account for a genetic predisposition to breast density), and/or qualitative assessments of MBD, such as BI-RADS® (e.g., $5^{th}$ edition, using Breast Composition categories of "a" (the breasts are almost entirely fatty), "b" (there are scattered areas of fibro-glandular density), "c" (the breasts are heterogeneously dense, which may obscure small masses), and "d" (the breasts are extremely dense, which lowers the sensitivity of mammography) (D'Orsi C J, Sickles E A, Mendelson E B, Morris E A et al. (2013). *ACR BI-RADS® Atlas, Breast Imaging Reporting and Data System*. Reston, VA: American College of Radiology).

Breast pain is a significant problem in female health. Breast pain is also associated with increases in VBD % and/or AVBD, breast stiffness, the risk of breast cancer or combinations thereof. Certain embodiments are directed to the use of an androgen agent and an aromatase inhibitor to reduce the breast pain in a patient.

Certain embodiments are directed to the use of a subcutaneous pellet comprising: an effective amount of anastrozole and an effective amount of testosterone. In exemplary embodiments, a subject is provided between 0.5-10 mg anastrozole (2,2'-[5-(1H-1,2,4-triazol-1-ylmethyl)-1,3-phenylene]bis(2-methylpropanenitrile)) and between 60-120 mg testosterone in a pharmaceutical formulation that has been compressed into a pellet. In exemplary embodiments, a subject is provided between 4-6 mg anastrozole and between 60-120 mg testosterone in a pharmaceutical formulation that has been compressed into a pellet. In exemplary embodiments, a subject is provided approximately 4 mg anastrozole and approximately 80 mg testosterone in a pharmaceutical formulation that has been compressed into a pellet. Other androgenic agents may also be used. The duration of treatment for administration of the subcutaneous pellet comprising: anastrozole and testosterone may vary between 2 weeks to 4 weeks, 3 months to 3 years, 6 months to 2 years, 3 months to 5 years, 1 year to 5 years, or 1 year to 3 years. In certain embodiments, the duration of treatment may be approximately 2 weeks, 3 months, 6 months, 9 months, 1 year, 1.5 years, 2 years, 2.5 years or 3 years. In certain embodiments, the duration of treatment may be at least 2 weeks, 3 months, 6 months, 9 months, 1 year, 1.5 years, 2 years, 3 year or 4 years. In certain embodiments, the duration of treatment may be approximately 3 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; and a stabilization and/or an increase in levels of androgen receptor expression.

Certain embodiments are directed to the use of a subcutaneous pellet comprising: an effective amount of letrozole and an effective amount of testosterone. In exemplary embodiments, a patient is provided a subcutaneous pellet comprising an 0.5-20 mg letrozole (4,4'-((1H-1,2,4-triazol-1 yl)methylene)dibenzonitrile) and between 40-130 mg testosterone for subcutaneous administration. In exemplary embodiments, a patient is provided a subcutaneous pellet comprising approximately 10 mg letrozole (4,4'-((1H-1,2,4-triazol-1yl)methylene)dibenzonitrile) and between 40-130 testosterone for subcutaneously administration. Other androgenic agents may also be used. The duration of treatment for administration of the subcutaneous pellet comprising letrozole and testosterone may vary between 2 weeks to 4 weeks, 3 months to 3 years, 6 months to 2 years, 3 months to 5 years, 1 year and 5 years or 1 year to 3 years. In certain embodiments, the duration of treatment may be approximately 2 weeks, 3 months, 6 months, 9 months, 1 year, 1.5 years, 2 years, 2.5 years, or 3 years. In certain embodiments, the duration of treatment may be at least 2 weeks, 3 months, 6 months, 9 months, 1 year, 1.5 years, 2 years, 3 year or 4 years. In certain embodiments, the duration of treatment may be approximately 3 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; and a stabilization and/or an increase in levels of androgen receptor expression.

Certain embodiments are directed to the use of a subcutaneous pellet comprising: an effective amount of exemestane and an effective amount of testosterone. In exemplary embodiments, a patient is provided a subcutaneous pellet comprising exemestane 10-75 mg 6-Methylideneandrosta-1,4-diene-3,17-dione and between 40-130 mg testosterone for subcutaneously administration. Other androgenic agents may also be used. The duration of treatment for administration of the exemestane and the testosterone may vary between 2 weeks to 4 weeks, 3 months to 3 years, 6 months to 2 years, 3 months to 5 years, 1 year and 5 years, or 1 year to 3 years. In certain embodiments, the duration of treatment may be approximately 2 weeks, 3 months, 6 months, 9 months, 1 year, 1.5 years, 2 years, 2.5 years or 3 years. In certain embodiments, the duration of treatment may be at least 2 weeks, 3 months, 6 months, 9 months, 1 year, 1.5 years, 2 years, 3 year or 4 years. In certain embodiments, the duration of treatment may be approximately 3 years. The treatment may be applied to one or more of the following: a reduction in ABD %, a reduction in AABD, a reduction in VBD %; a reduction in AVBD; a reduction in breast pain; a reduction in breast stiffness; a reduction in breast elasticity; a reduction in macromastia; a reduction in breast cysts; an improvement in mammographic diagnostic sensitivity and a reduction in false positives; an increase in the ratio between fibro-glandular and adipose tissue; and a stabilization and/or an increase in levels of androgen receptor expression.

Preparation of esters, as noted herein, involves functionalization of hydroxyl and/or carboxyl groups that may be present, as will be appreciated by those skilled in the arts of pharmaceutical chemistry and drug delivery. For example, to prepare testosterone esters, the 17-hydroxyl group of the testosterone molecule is generally caused to react with a suitable organic acid under esterifying conditions, such conditions typically involving the use of a strong acid such as sulfuric acid, hydrochloric acid, or the like, and a temperature sufficient to allow the reaction to proceed at reflux. Esters may be reconverted to the free acids, if desired, by using conventional hydrogenolysis or hydrolysis procedures.

An effective amount of an androgenic agent may vary among androgenic agents. In addition, the effective amount per day of testosterone may also vary. In certain aspects, an effective amount of testosterone may be delivered in the form of a subcutaneous implant. In certain embodiments, an effective amount of testosterone may be between 40 and 200 mg. For example, in certain embodiments, the effective amount of testosterone may be between 40 to 120 mg, for example, 20 mg, 40 mg, 60 mg 80 mg, 100 mg or 120 mg.

In certain embodiments, an effective amount of testosterone may be delivered in the form of a subcutaneous implant, such as a subcutaneous pellet, containing between 40 to 200 mg testosterone, such as between 40 to 150 mg, 40 to 100 mg, 100 to 200 mg, 50 to 150 mg, 50 to 100 mg, 40 to 100 mg, 30 to 80 mg, 40 to 90 mg, 40 to 90 mg, 40 to 80 mg, 40 to 70 mg, 40 to 60 mg, 40 to 50 mg, 40 to 100 mg, 60 to 100 mg, 45 to 75 mg or 40 to 45 mg testosterone.

An effective amount per day of methyltestosterone may vary. In exemplary embodiments, the effective amount of methyltestosterone may be between 0.1 mg to 10 mg, such as between 0.5 mg to 9 mg, 2 mg to 8 mg, 3 mg to 7 mg, or 4 mg to 5 mg. For example, the effective amount of methyltestosterone may be 0.5 mg, 1.25 mg or 2.5 mg.

The effective amount of androgenic agent used in conjunction with an aromatase inhibitor may be relatively lower than a standard dose because of low levels of sex hormone binding globulin in the patient's serum which may be caused by the aromatase inhibitor.

Sex hormone binding globulin binds an androgenic agent (e.g., testosterone) and transports it around the body. Its production is regulated by several mechanisms, but one of the effectors of its level is the amount of estrogen in the serum: the higher the estrogen, the higher the sex hormone binding globulin and the lower the free androgenic agent. Conversely, the lower the estrogen, the lower the sex hormone binding globulin, and the higher the free androgenic agent, which means the androgenic agent has higher bioavailability. Thus, after menopause, as the estrogen level falls, the sex hormone binding globulin level falls and the free androgenic agent such as testosterone rises. This free androgenic agent has multiple functions, as the androgen receptor is expressed in all cells of the body.

In certain embodiments, the dosage levels below the lower limit of the aforesaid range of the androgenic agent may be more than adequate, while in other cases still larger doses above the upper limit of the aforesaid range may be employed without causing any harmful side effects.

In certain embodiments, the aromatase inhibitor may be, for example, a steroidal aromatase inhibitor, a nonsteroidal aromatase inhibitor, and/or isomers thereof. Steroidal aromatase inhibitors developed to date build upon the basic androstenedione nucleus and incorporate chemical substituents at varying positions on the steroid. Examples of steroidal aromatase inhibitors include but are not limited to, exemestane (Aromasin®) and formestane. Additional examples include mechanism-based steroidal aromatase inhibitors that mimic the substrate, are converted by the enzyme to a reactive intermediate, and result in the inactivation of aromatase. In certain embodiments, the aromatase inhibitor is exemestane. Nonsteroidal aromatase inhibitors may be divided into three classes: aminoglutethimide-like molecules, imidazole/triazole derivatives, and flavonoid analogs. Examples of non-steroidal aromatase inhibitors include anastrozole, exemestane, or letrozole. In certain embodiments, the aromatase inhibitor is either anastrozole or letrozole. In certain embodiments, the aromatase inhibitor is anastrozole.

Aromatase inhibitors often include third-generation aromatase inhibitors, such as anastrozole (Arimidex®), exemestane (Aromasin®), and letrozole (Femara®). These third-generation aromatase inhibitors have brought a change in the therapeutic approach to patients with hormone-sensitive breast cancer. Such aromatase inhibitors are specific in their action in that they virtually ablate estrogen in the serum and thus lower sex hormone binding globulin, which enables the achievement of a synergistic effect.

In certain embodiments, the aromatase inhibitor may be selected from the group consisting of anastrozole, exemestane, or letrozole. In certain embodiments, the aromatase inhibitor is either anastrozole or letrozole. In certain embodiments, the aromatase inhibitor is anastrozole.

In certain embodiments, a method is provided for determining if the patient has a breast with a BI-RADS® score of 3 or 4 (or c or d); a breast with a mammographic breast density of 7.5% or greater; a mammographically dense breast; a breast with the same or more breast tissue than fat; a breast with more breast tissue than fat; breast cancer or combinations thereof.

In certain embodiments, the patient has or is diagnosed with having, a breast with a BI-RADS® score (1-4 scale) in the range of between 2 and 4, for example, between 2 and 3, or between 3 and 4. In certain embodiments, the patient has or is diagnosed with having, a breast with a BI-RADS® score of 2 or more, for example, a BI-RADS® score of 3 or 4, or a BI-RADS® score of 4.

In certain embodiments, the patient has or is diagnosed with having, a breast with a BI-RADS® score (a-d scale) in the range of between b and d, for example, between b and c, or between c and d. In certain embodiments, the patient has or is diagnosed with having, a breast with a BI-RADS® score of b or more, for example, a BI-RADS® score of c or d, or a BI-RADS® score of d.

In certain embodiments, the patient has or is diagnosed with having, a breast with a mammographic breast density of 7.5% or greater, for example, a mammographic breast density of 10% or greater, 15% or greater, 20% or greater, 30% or greater, 50% or greater, 70% or greater, or 95% or greater.

In certain embodiments, the patient has or is diagnosed with having, a breast with a VBD % of 7.5% or greater, for example, a VBD % of 10% or greater, 15% or greater, 20% or greater, 30% or greater, 50% or greater, 70% or greater, or 95% or greater.

In certain embodiments, the patient has or is diagnosed with having, a breast with an ABD % of 7.5% or greater, for example, an ABD % of 10% or greater, 15% or greater, 20% or greater, 30% or greater, 50% or greater, 70% or greater, or 95% or greater.

In certain embodiments, the patient has or is diagnosed with having, a breast with a BI-RADS® score of 3 (or c) and a mammographic breast density of 7.5% or greater, for example, a mammographic breast density of 10% or greater, 15% or greater, 20% or greater, 30% or greater, 50% or greater, 70% or greater, or 95% or greater. In certain embodiments, the patient has or is diagnosed with having, a breast with a BI-RADS® score of 4 (or d) and a mammographic breast density of 7.5% or greater, for example, a mammographic breast density of 10% or greater, 15% or greater, 20% or greater, 30% or greater, 50% or greater, or greater, or 95% or greater.

In certain embodiments, the patient has or is diagnosed with having, a breast with a VBD % in the range of between 1% to 100%, for example, a VBD % of between 1% and 24%, 5% to 100%, 5% to 95%, 5% to 90%, 5% to 80%, 5% to 70%, 5% to 60%, 5% to 50%, 5% to 40%, 5% to 30%, 5% to 25%, 5% to 20%, 10% to 100%, 10% to 95%, 10% to 90%, 10% to 80%, 10% to 70%, 10% to 60%, 10% to 50%, 10% to 40%, 10% to 30%, 10% to 25%, 10% to 20%, 25% to 100%, 25% to 75%, 25% to 50%, 25% to 49%, 30% to 100%, 30% to 95%, 30% to 90%, 30% to 80%, 30% to 70%, 30% to 60%, 30% to 50%, 30% to 40%, 40% to 100%, 40% to 95%, 40% to 90%, 40% to 80%, 40% to 70%, 40% to 60%, 40% to 50%, 50% to 100%, 50% to 95%, 50% to 90%, 50% to 80%, 50% to 75%, 50% to 74%, 50% to 70%, 50% to 60%, 75% to 100%, 75% to 95%, or a VBD % of 75% to 90%. In certain embodiments, the patient has or is diagnosed with having, a breast with a VBD % in the range of between 10% to 40%.

In certain embodiments, the patient has or is diagnosed with having, a breast with a ABD % in the range of between 1% to 100%, for example, a ABD % of between 1% and 24%, 5% to 100%, 5% to 95%, 5% to 90%, 5% to 80%, 5% to 70%, 5% to 60%, 5% to 50%, 5% to 40%, 5% to 30%, 5% to 25%, 5% to 20%, 10% to 100%, 10% to 95%, 10% to 90%, 10% to 80%, 10% to 70%, 10% to 60%, 10% to 50%, 10% to 40%, 10% to 30%, 10% to 25%, 10% to 20%, 25% to 100%, 25% to 75%, 25% to 50%, 25% to 49%, 30% to 100%, 30% to 95%, 30% to 90%, 30% to 80%, 30% to 70%, 30% to 60%, 30% to 50%, 30% to 40%, 40% to 100%, 40% to 95%, 40% to 90%, 40% to 80%, 40% to 70%, 40% to 60%, 40% to 50%, 50% to 100%, 50% to 95%, 50% to 90%, 50% to 80%, 50% to 75%, 50% to 74%, 50% to 70%, 50% to 60%, 75% to 100%, 75% to 95%, or a ABD % of 75% to 90%. In certain embodiments, the patient has, or is diagnosed with having, a breast with a ABD % in the range of between 50% to 100%. In certain embodiments, the patient has or is diagnosed with having, a mammographically dense breast, for example, a breast having about the same or more breast tissue than fat.

In certain embodiments, the patient is a peri-menopausal woman or a post-menopausal woman. In certain embodiments, the patient is a perimenopausal woman.

In certain embodiments, the pharmaceutical formulation may be used to reduce or decrease the patient's BI-RADS® score one or more annual intervening mammographic detections. For example, the pharmaceutical formulation may be used to reduce or decrease the patient's BI-RADS® score by 1 or more points one or more annual intervening mammographic detections, such as, by 2 or more, 3 or 4, or 4 points one or more annual intervening mammographic detections. In certain embodiments, the pharmaceutical formulation may be used to reduce or decrease the patient's BI-RADS® score by 1 point one or more annual intervening mammographic detections, for example, by 2, 3, or 4 points one or more annual intervening mammographic detections. In certain embodiments, the pharmaceutical formulation maintains or stabilizes the patient's BI-RADS® score one or more annual intervening mammographic detections.

The time period the one or more annual intervening mammographic detections may be 1 to 20 years, for example, 1 year, 1.5 years, 2 years, 3 years, 4 years, 5 years, 6 years, 10 years, 15 years, or 20 years. The time period the one or more annual intervening mammographic detections may be 1 year, 2 years, 4 years, 5 years, 7 years, 10 years, 15 years, or 20 years.

In certain embodiments, the pharmaceutical formulation may be used to reduce or decrease the mammographic breast density of the patient's breast one or more annual intervening mammographic detections. In certain embodiments, the pharmaceutical formulation may be used to reduce or decrease the VBD % and/or AVBD of the patient's breast one or more annual intervening mammographic detections. In certain embodiments, the pharmaceutical formulation may be used to reduce or decrease the ABD % and/or AABD of the patient's breast between one or more annual intervening mammographic detections. For example, the pharmaceutical formulation may be used to reduce or decrease the mammographic breast density of the patient's breast in the range of between 1% to 99% between one or more annual intervening mammographic detections, such as, in the range of between 1% to 80%, 1% to 50%, 1% to 30%, 1% to 20%, 1% to 10%, 3% to 40%, 3% to 20%, 5% to 60%, 5% to 25%, 5% to 15%, 5% to 10%, 10% to 60%, 10% to 40%, 10% to 30%, 10% to 20%, 10% to 15%, 20% to 60%, 20% to 40%, 20% to 30%, 30% to 60%, 30% to 50%, or 30% to 40% between one or more annual intervening mammographic detections. For example, the pharmaceutical formulation may be used to reduce or decrease the VBD % and/or AVBD of the patient's breast in the range of between 1% to 99% between one or more annual intervening mammographic detections, such as, in the range of between 1% to 80%, 1% to 50%, 1% to 30%, 1% to 20%, 1% to 10%, 3% to 40%, 3% to 20%, 5% to 60%, 5% to 25%, 5% to 15%, 5% to 10%, 10% to 60%, 10% to 40%, 10% to 30%, 10% to 20%, 10% to 15%, 20% to 60%, 20% to 40%, 20% to 30%, 30% to 60%, 30% to 50%, or 30% to 40% between one or more annual intervening mammographic detections. For example, the pharmaceutical formulation may be used to reduce or decrease the ABD % and/or AABD of the patient's breast in the range of between 1% to 99% between one or more annual intervening mammographic detections, such as, in the range of between 1% to 80%, 1% to 50%, 1% to 30%, 1% to 20%, 1% to 10%, 3% to 40%, 3% to 20%, 5% to 60%, 5% to 25%, 5% to 15%, 5% to 10%, 10% to 60%, 10% to 40%, 10% to 30%, 10% to 20%, 10% to 15%, 20% to 60%, 20% to 40%, 20% to 30%, 30% to 60%, 30% to 50%, or 30% to 40% between one or more annual intervening mammographic detections. For example, the pharmaceutical formulation may be used to reduce or decrease the mammographic breast density of the patient's breast by at least 2% between one or more annual intervening mammographic detections, such as, by at least 5%, 10%, 20%, 30%, 40%, 50%, 75%, 85%, 95%, or 99% between one or more annual intervening mammographic detections. For example, the pharmaceutical formulation may be used to reduce or decrease the VBD % and/or AVBD of the patient's breast by at least 2% between one or more annual intervening mammographic detections, such as, by at least 5%, 10%, 20%, 30%, 40%, 50%, 75%, 85%, 95%, or 99% between one or more annual intervening mammographic detections. For example, the pharmaceutical formulation may be used to reduce or decrease the ABD % and/or AABD of the patient's breast by at least 2% between one or more annual intervening mammographic detections, such as, by at least 5%, 10%, 20%, 30%, 40%, 50%, 75%, 85%, 95%, or 99% between one or more annual intervening mammographic detections. In certain embodiments, the pharmaceutical formulation may be used to maintain or stabilize the mammographic breast density of the patient's breast between one or more annual intervening mammographic detections.

In certain embodiments, the pharmaceutical formulation may be used to reduce or decrease the mammographic breast density of the patient's breast by at least 2%, such as 5%, 10%, 20%, or 30%, over a 4 hour period, such as over an 8 hour, 24 hour, 1 day, 3 days, 1 week, 2 weeks, 1 month, 2 month, 3 months, 6 months, 9 months, or 1 year period.

In certain embodiments, the pharmaceutical formulation may be used to reduce or decrease the mammographic breast density VBD % and/or AVBD of the patient's breast by at least 2%, such as 5%, 10%, 20%, or 30%, over a 4 hour period, such as over an 8 hour, 24 hour, 1 day, 3 days, 1 week, 2 weeks, 1 month, 2 month, 3 months, 6 months, 9 months, or 1 year period.

In certain embodiments, the pharmaceutical formulation may be used to reduce or decrease the mammographic breast density ABD % and/or AABD of the patient's breast by at least 2%, such as 5%, 10%, 20%, or 30%, over a 4 hour period, such as over an 8 hour, 24 hour, 1 day, 3 days, 1 week, 2 weeks, 1 month, 2 month, 3 months, 6 months, 9 months, or 1 year period.

In certain embodiments, the pharmaceutical formulation may be used to mitigate or reduce the patient's risk of developing breast cancer. For example, in certain embodiments, the pharmaceutical formulation may be used to mitigate or reduce the patient's risk of developing breast cancer between one or more annual intervening mammographic detections. In certain embodiments, the pharmaceutical formulation may be used to mitigate or reduce the patient's risk of developing breast cancer and avoids, mitigates, reduces or reverses one or more peri-menopausal symptoms between one or more annual intervening mammographic detections. For example, the one or more peri-menopausal symptoms that may be mitigated, reduced, or avoided may include but is not limited to, menstrual irregularity; hot flashes and sleep problems; mood changes; mood swings; irritability; depression; vaginal dryness; urinary or vaginal infections; urinary incontinence; decreasing fertility; changes in sexual arousal or desire; bone loss; fragile bones; osteoporosis; or changing cholesterol levels, such as an increase in low-density lipoprotein (LDL) cholesterol, a decrease in high-density lipoprotein (HDL) cholesterol; or combinations thereof.

In certain embodiments, the pharmaceutical formulations may be used to increase or improve the patient's fat to breast tissue ratio between one or more annual intervening mammographic detections. For example, the pharmaceutical formulation increases or improves the patient's fat to breast tissue ratio from 1:19 to 19:1 between one or more annual intervening mammographic detections, such as increases or improves the treated patient's fat to breast tissue ratio from 1:15 to 19:1, from 1:10 to 19:1, from 1:5 to 19:1, from 1:2 to 19:1, from 2:3 to 19:1, from 2:1 to 19:1, from 4:1 to 19:1, from 6:1 to 19:1, from 8:1 to 19:1, from 10:1 to 19:1, from 1:19 to 10:1, from 1:10 to 10:1, from 1:4 to 10:1, from 1:2 to 10:1, from 3:2 to 10:1, from 3:1 to 10:1, from 5:1 to 10:1, from 7:1 to 10:1, from 9:1 to 10:1, from 15:1 to 10:1, from 1:15 to 5:1, from 1:5 to 5:1, from 1:3 to 5:1, from 3:2 to 5:1, from 3:1 to 5:1, from 6:1 to 5:1, 8:1 to 5:1, from 10:1 to 5:1, from 1:19 to 3:1, from 1:10 to 3:1, from 1:4 to 3:1, from 1:2 to 3:1, from 2:1 to 3:1, from 4:1 to 3:1, from 6:1 to 3:1, from 8:1 to 3:1, from 10:1 to 3:1, or from 15:1 to 3:1 between one or more annual intervening mammographic detections.

In certain embodiments, the pharmaceutical formulation may be used to increase or improve the patient's fat to breast tissue ratio from 1:19 to 19:1, such as from 1:10 to 19:1, from 1:5 to 19:1, from 1:2 to 19:1, from 2:3 to 19:1, from 2:1 to 19:1, over a 4 hour period, over an 8 hour period, over a 24 hour period, over a 3 day period, over a 1 week period, over a 2 week period, over a 1 month period, over a 2 month period, over a 3 month period, over a 6 month period, over a 9 month period, over a 1 year period, or over a 5 year period.

In certain embodiments, the pharmaceutical formulations may be used to increase the percentage of fat in the treated patient's breast between one or more annual intervening mammographic detections. For example, the pharmaceutical formulation increases the percentage of fat in the treated patient's breast in the range of between 1% to 99% between one or more annual intervening mammographic detections, such as, in the range of between 1% to 90%, 1% to 70%, 1% to 50%, 1% to 30%, 1% to 20%, 1% to 15%, 1% to 10%, 3% to 60%, 3% to 20%, 5% to 70%, 5% to 50%, 5% to 30%, 5% to 20%, 5% to 15%, 5% to 10%, 10% to 60%, 10% to 40%, 10% to 30%, 10% to 20%, 10% to 15%, 20% to 50%, 20% to 30%, 30% to 60%, 30% to 50%, or 30% to 40% between one or more annual intervening mammographic detections.

In certain embodiments, the pharmaceutical formulation increases the percentage of fat in the treated patient's breast by at least 2%, such as by at least 5%, by at least 10%, by at least 25%, by at least 40%, by at least 75%, by at least 95%, or by at least 99%, over a 4 hour period, such as over an 8 hour period, over a 24 hour period, over a 3 day period, over a 1 week period, over a 2 week period, over a 1 month period, over a 2 month period, over a 3 month period, over a 6 month period, over a 9 month period, over a 1 year period, or over a 5 year period.

In certain embodiments, the pharmaceutical formulation enhances, increases, or improves, breast compression during mammographic visualization or detection of the breast between one or more annual intervening mammographic detections. For example, the pharmaceutical formulation enhances, increases, or improves, breast compression during mammographic visualization or detection of the breast in the range of between 5% to 70%, 5% to 50%, 5% to 30%, 5% to 20%, 5% to 15%, 5% to 10%, 10% to 50%, 10% to 30%, 10% to 20%, 10% to 15%, 20% to 60%, 20% to 40%, 20% to 30%, 30% to 70%, 30% to 50%, or between 30% to 40% between one or more annual intervening mammographic detections. In certain embodiments, as a result of the enhanced, increased, or improved, breast compression during mammographic visualization or detection of the breast, the pharmaceutical formulation further mitigates or reduces the patient's pain during the breast compression. For example, the pharmaceutical formulation further mitigates, reduces or minimizes, the patient's pain during the breast compression in the range of between 5% to 80%, 5% to 50%, 5% to 30%, 5% to 20%, 5% to 15%, 5% to 10%, 10% to 80%, 10% to 60%, 10% to 40%, 10% to 20%, 10% to 15%, 20% to 70%, 20% to 50%, 20% to 30%, 30% to 70%, 30% to 50%, or between 30% to 40% less pain as a result of the enhanced, increased, or improved, breast compression during mammographic visualization or detection of the breast.

In certain embodiments, the pharmaceutical formulation mitigates or reduces the patient's pain during the breast compression. For example, the pharmaceutical formulation mitigates or reduces the patient's pain during the breast compression in the range of between 5% to 80%, 5% to 60%, 5% to 30%, 5% to 20%, 5% to 15%, 5% to 10%, 10% to 80%, 10% to 60%, 10% to 40%, 10% to 30%, 10% to 20%, 10% to 15%, 20% to 70%, 20% to 50%, 20% to 30%, 30% to 90%, 30% to 50%, or between 30% to 40% between one or more annual intervening mammographic detections. In certain embodiments, as a result of the patient's mitigated, reduced or minimized pain during the breast compression, the pharmaceutical formulation further enhances, increases, or improves, breast compression during mammographic visualization or detection of the breast between one or more annual intervening mammographic detections. For example, the pharmaceutical formulation further enhances, increases, or improves, breast compression during mammographic visualization or detection of the breast between one or more annual intervening mammographic detections in the range of between 5% to 80%, 5% to 60%, 5% to 40%, 5% to 30%, 5% to 20%, 5% to 15%, 5% to 10%, 10% to 80%, 10% to 60%, 10% to 40%, 10% to 20%, 10% to 15%, 20% to 80%, 20% to 60%, 20% to 30%, 30% to 80%, 30% to 50%, or between 30% to 40% between one or more annual intervening mammographic detections.

In certain embodiments, the pharmaceutical formulation mitigates or reduces the patient's pain according to the visual analog scale (VAS) during the breast compression. For example, the pharmaceutical formulation mitigates or reduces the patient's pain according to the VAS during the breast compression such that the patient does not suffer from significant pain between 50-100 mm, 50-80 mm, 50-70 mm, 60-100 mm, 70-100 mm, 80-100 mm or between 90-100 mm during one or more mammographic detections or during one or more annual intervening mammographic detections.

In certain embodiments, the pharmaceutical formulation enhances increases or improves the patient's compliance of having regular mammographic visualizations or detections, for example, compliance with mammographic visualizations or detections at every 6 months, annually, every 2 years, every 3 years, or every 5 years.

In certain embodiments, the pharmaceutical formulation mitigates or reduces the amount of radiation exposure required to visualize or detect the patient's breast during one or more subsequent mammographies, such as during one or more subsequent annual mammographies. For example, the pharmaceutical formulation mitigates or reduces the amount of radiation exposure required to visualize or detect the patient's breast in the range of between 5% to 99%, 5% to 80%, 5% to 70%, 5% to 50%, 5% to 30%, 5% to 20%, 5% to 15%, 5% to 10%, 10% to 80%, 10% to 60%, 10% to 40%, 10% to 20%, 10% to 15%, 20% to 80%, 20% to 60%, 20% to 40%, 20% to 30%, 30% to 80%, 30% to 60%, 30% to 50% or between 30% to 40% during one or more subsequent mammographies, such as during one or more subsequent annual mammographies.

In certain embodiments, the pharmaceutical formulation induces breast involution in the breast of the patient, for example, in the breast of a peri-menopausal patient.

In certain embodiments, the pharmaceutical formulation induces involution of breast cells in the breast of the patient, for example, in the breast of a peri-menopausal patient.

In certain embodiments, the pharmaceutical formulation induces net cell death over proliferation in the breast of the patient, for example, in the breast of a peri-menopausal patient.

In certain embodiments, the pharmaceutical formulation reverses cell number and mammographic breast density in the breast of the patient, for example, in the breast of a peri-menopausal patient.

In certain embodiments, the pharmaceutical formulation mitigates or reduces breast stiffness in the breast of the patient, for example, in the breast of a peri-menopausal patient. For example, the pharmaceutical formulation mitigates or reduces breast stiffness in the breast of the patient in the range of between 5% to 80%, 5% to 60%, 5% to 40%, 5% to 20%, 5% to 15%, 5% to 10%, 10% to 80%, 10% to 60%, 10% to 40%, 10% to 30%, 10% to 20%, 10% to 15%, 20% to 80%, 20% to 60%, 20% to 40%, 20% to 30%, 30% to 80%, 30% to 60%, or between 30% to 40%, between one or more annual intervening mammographic detections. For example, the pharmaceutical formulation mitigates or reduces breast stiffness in the breast of the patient by at least 5%, such as at least 8%, at least 10%, at least 15%, at least 20%, or at least 30%, per annum. In certain embodiments, the pharmaceutical formulation mitigates or reduces breast stiffness in the breast of the patient by at least 5%, such as at least 8%, at least 10%, at least 15%, at least 20%, or at least 30%, over a 4 hour period, such as over an 8 hour period, a 24 hour period, a 3 day period, a 1 week period, a 2 week period, a 1 month period, a 2 month period, a 3 month period, a 6 month period, a 9 month period, a 1 year period, or a 5 year period.

In certain embodiments, the pharmaceutical formulation enhances, increases, or improves mammographic visualization or detection of the breast of the patient, for example, the breast of a peri-menopausal patient. For example, the pharmaceutical formulation enhances, increases, or improves mammographic visualization or detection of the breast of the patient in the range of between 5% to 80%, 5% to 50%, 5% to 30%, 5% to 20%, 5% to 15%, 5% to 10%, 10% to 80%, 10% to 60%, 10% to 30%, 10% to 20%, 10% to 15%, 20% to 80%, 20% to 60%, 20% to 30%, 30% to 80%, 30% to 60%, or between 30% to 40%, between one or more annual intervening mammographic detections. In certain embodiments, the pharmaceutical formulation enhances, increases, or improves mammographic visualization or detection of the breast of the patient by at least 5%, such as at least 10%, at least 15%, at least 25%, at least 40%, at least 50%, or at least 75%, over a 4 hour period, or over other time periods, such 8 hours, 24 hours, 3 days, 1 week, 2 weeks, 1 month, 2 month, 3 months, 6 months, 9 months, 1 year, or 5 years.

In certain embodiments, the pharmaceutical formulation reduces mammographic breast density and avoids inducing masculinizing androgenic side-effects or inducing a hyper-androgenic state. For example, masculinizing androgenic side-effects may include male-type baldness, hirsutism, or increased hair in areas unwanted by the patient, voice deepening, acne, or combinations thereof. In certain embodiments, the pharmaceutical formulation reduces mammographic breast density and is exclusive of inducing masculinizing androgenic side-effects or inducing a hyper-androgenic state. In certain embodiments, the pharmaceutical formulation reduces mammographic breast density and minimizes induction of masculinizing androgenic side-effects or induction of a hyper-androgenic state.

In certain embodiments, the pharmaceutical formulation substantially improves or improves the patient's physical functioning, such as physical functioning related to the patient's central nervous system, libido, musculoskeletal system, cardiovascular system, risk of contracting autoimmune diseases, the severity of symptoms associated with autoimmune disease, or combinations thereof. For example, as related to the patient's central nervous system, the pharmaceutical formulation may reduce depression, anxiety, general cognitive dysfunction including memory, or reduce the risk of dementia and Parkinsonism. For example, as related to the patient's libido, the pharmaceutical formulation may provide a significant improvement in global libido, including speed to sexual arousal and the ability to achieve orgasm. For example, as related to the patient's musculoskeletal system, the pharmaceutical formulation may provide for a reduction in inflammatory and degenerative arthritis, an improvement in bone mineral density, or an improvement in muscle strength. For example, as related to the patient's cardiovascular system, the pharmaceutical formulation may provide a reduction in foamy macrophage deposition in the arterial wall, a reduction in atherosclerosis, an increase in high density lipoprotein's leading to an improvement in cholesterol, or a high-density lipoprotein ratio. For example, as related to the patient's risk of contracting autoimmune diseases, the pharmaceutical formulation may substantially reduce or reduces the treated patient's risk of contracting autoimmune diseases, such as Sjogren's syndrome, lupus, and rheumatoid arthritis. For example, as related to the severity of symptoms associated with the patient's autoimmune disease, the pharmaceutical formulation may substantially reduce or reduces the severity of symptoms associated with a treated patient's autoimmune disease, such as Sjogren's syndrome, lupus, and rheumatoid arthritis. In certain embodiments, the pharmaceutical formulation substantially improves or improves the patient's physical functioning, such as cognitive function; reduction of a degenerative CNS disease, comprising dementia or parkinsonism; muscle strength; libido; energy; reduction of monoamine oxidase induced anxiety and depression; or combinations thereof.

In certain embodiments, the pharmaceutical formulation further provides one or more of the following: i) reduces mammographic breast density; ii) increases involutionary effects on the patient's breast without conversion of testosterone to estrogen; iii) substantially reduces, reduces, or reverses peri-menopausal symptoms; or iv) substantially improves or improves the patient's physical functioning, comprising cognitive function; reduction of symptoms associated with a degenerative CNS disease, comprising dementia or parkinsonism; muscle strength; libido; energy; reduction of monoamine oxidase induced anxiety and depression; or combinations thereof. In certain embodiments, the pharmaceutical formulation further provides one or more of the following: i) reduces mammographic breast density; ii) increases involutionary effects on hormonally affected end organs, comprising breast, without conversion of testosterone to estrogen; iii) substantially reduces, reduces, or reverses peri-menopausal symptoms related to fluctuating estrogen levels; or iv) substantially improves or improves the patient's physical functioning, comprising cognitive function; reduction of symptoms associated with a degenerative CNS disease, comprising dementia or parkinsonism; muscle strength; libido; energy; reduction of monoamine oxidase induced anxiety and depression; or combinations thereof.

In certain embodiments, the patient has a high free androgenic index level, for example, 30% or greater, within their breast within four hours of the administration of the androgenic agent and the aromatase inhibitor. In certain embodiments, the patient has a supra-physiological free androgenic index level within their breast within four hours of the administration of the androgenic agent and the aromatase inhibitor.

In certain embodiments, the treatment with a pharmaceutical formulation or combination treatment of the androgenic agent and the aromatase inhibitor as described herein further comprises: a) measuring free androgenic index levels and/or aromatase inhibitor levels in serum isolated from a blood sample taken from the patient after at least 1 month of treatment; b) determining a subsequent dose, comprising a subsequent effective amount of androgenic agent and a subsequent effective amount of an aromatase inhibitor; and c) administering to the patient the subsequent dose.

In certain embodiments, the treatment with a pharmaceutical formulation or combination treatment of the androgenic agent and the aromatase inhibitor as described herein further comprises: a) measuring free androgenic index levels and/or aromatase inhibitor levels in serum isolated from a blood sample taken from the patient after at least 1 month of treatment, comprising centrifuging the patient's blood sample to isolate the serum; b) determining a subsequent dose, comprising a subsequent effective amount of androgenic agent and a subsequent effective amount of an aromatase inhibitor; and c) administering to the patient the subsequent dose.

In certain embodiments, the measured free androgenic index serum levels of a treated patient after 1 month may be between 10-25%, such as between 10-20%, 10-15%, 15-25%, 15-20%, 12-18%, 8-15%, or between 11-14%.

In certain embodiments, the measured free androgenic index serum levels of a treated patient after 3 months may be between 2-10%, such as between 2-8%, 2-6%, 2-5%, 2-4%, 4-10%, 5-8%, 3-7%, 4-6%, 3-6%, 4-7%, 5-10% or between 2-5%.

In certain embodiments, the administration of the aromatase inhibitor reduces aromatization of testosterone to estrogen in the subcutaneous fat of the treated patient, for example, reduces aromatization by 80-95% or 100%. For example, the administered aromatase inhibitor may reduce aromatization of testosterone to estrogen in the subcutaneous fat of the patient's breast, the subcutaneous fat of the patient's pelvis, the subcutaneous fat of the patient's buttocks, the subcutaneous fat of the patient's abdomen or combinations thereof, for example, reduces aromatization by 80-95% or 100%.

In certain embodiments, the administration of the aromatase inhibitor reduces aromatization of adrenal androgens, for example, androstenedione, to estrogen in the subcutaneous fat of the treated patient, for example, reduces aromatization by 80-95% or 100%. For example, the administered aromatase inhibitor may reduce aromatization of testosterone to estrogen in the subcutaneous fat of the patient's breast, the subcutaneous fat of the patient's pelvis, the subcutaneous fat of the patient's buttocks, the subcutaneous fat of the patient's abdomen or combinations thereof, for example, reduces aromatization by 80-95% or 100%.

Annual mammographic screening of density may be undertaken to determine the reduction in breast density utilizing an appropriate mammographic algorithm that measures the volume of fibro-glandular tissue as a percentage of total breast volume (MBD). The objective is to achieve MBD of less than 10% when this is a function of the average of both breast densities. The rate of breast density reduction should be at least 2% per annum. An annual uplift factor (V1(N) in the above) may be introduced into TD and AD of 10% of dosing if 2% is not achieved in the first year. This annual uplift factor typically will only be introduced, on an annual basis, if there is less than 10% increase in androgenicity index (AI).

Annual mammographic screening of density may be undertaken to determine a reduction in breast density utilizing an appropriate mammographic algorithm that measures the volume of fibro-glandular tissue as a percentage of total breast volume (VBD %). The objective is to achieve VBD % of less than 10% when this is a function of the average of both breast densities. The rate of breast density reduction (VBD %) should be at least 2% per annum. An annual uplift factor (V1(N) in the above) may be introduced into TD and AD of 10% of dosing if 2% is not achieved in the first year. This annual uplift factor typically will only be introduced, on an annual basis, if there is less than 10% increase in androgenicity index (AI).

In certain embodiments, the administration of aromatase inhibitor in combination with testosterone results in an improvement in the bioavailability of dihydrotestosterone between 25% to 75%, 35% to 65% or 45% to 55%. In certain embodiments, the amount of increase in bioavailability of dihydrotestosterone is greater than 25%, greater than 35%, greater than 45% or greater than 55%.

The androgenic agent used in a pharmaceutical formulation or combination treatment as described herein, for example, may be selected from the group consisting of testosterone, methyltestosterone, and/or dehydroepiandrosterone. In certain embodiments, the androgenic agent may be testosterone undecanoate, such as about 40 mg of testosterone undecanoate. The aromatase inhibitor, for example, may be selected from the group consisting of anastrozole, exemestane, or letrozole. In certain aspects, the aromatase inhibitor may be anastrozole, such as about 1 mg of anastrozole.

In certain embodiments, the pharmaceutical formulation may include administering a pharmaceutical formulation comprising an androgenic agent linked to an aromatase inhibitor, e.g., via an ester linkage, or an androgenic agent/aromatase inhibitor complex, wherein the complex is created by methods in the art.

In preferred embodiments, both the androgenic agent (e.g., testosterone, methyltestosterone, and/or dehydroepiandrosterone), and the aromatase inhibitor (e.g., anastrozole, exemestane, or letrozole) are administered subcutaneously, e.g., as an implant such as a pellet.

In certain embodiments, the androgenic agent (e.g., testosterone, methyltestosterone, and/or dehydroepiandrosterone), and the aromatase inhibitor (e.g., anastrozole, exemestane, or letrozole) are administered subcutaneously, e.g., as a pellet. For example, testosterone and anastrozole may be administered subcutaneously.

The appropriate dosing regimen utilizing the androgenic agent, the aromatase inhibitor, or pharmaceutical formulations comprising the androgenic agent and the aromatase inhibitor, the amount of each dose administered, and the intervals between doses of the compounds may depend on various factors such as the particular aromatase inhibitor and androgenic agent being used in combination, the type of pharmaceutical formulation being used, the type of physiological condition being treated, the characteristics of the subject being treated (e.g., species, age, weight, sex, medical condition, fed/fasted), the route of administration, and the severity of the disorder being treated or combinations thereof. A physician or diagnostician of ordinary skill may readily determine and prescribe the effective amount of the androgenic agent, the aromatase inhibitor, or pharmaceutical formulation to prevent or to treat the specific physiological condition.

The pharmaceutical formulation or formulation to be administered may contain a quantity of the compounds or pharmaceutically acceptable salts or esters thereof in an amount effective to treat the condition of the subject being treated. Because two different compounds may be used together in a combination therapy, the potency of each of the compounds and the interactive effects achieved by combining them together typically will also be taken into account. A consideration of these factors is well within the purview of the ordinarily skilled clinician for the purpose of determining the therapeutically effective or prophylactically effective dosage amounts needed to improve side effects.

Administration of the androgenic agent and the aromatase inhibitor, or the pharmaceutical formulation comprising a combination of the same, to the subject includes both self-administration and administration to the subject by another person (e.g., physician, nurse, health care worker, friend, etc.).

In certain embodiments, the pharmaceutical formulation may be formulated in a manner compatible with a desired outcome. The pharmaceutical formulations may be administered in a convenient formulation. The following formulation examples only are illustrative and are not intended to limit the scope of the present disclosure.

In certain embodiments, the pharmaceutical formulation can be an implant or pellet formulated by direct compression. For example, the pellet formulations may incorporate diluents, binders, lubricants and, disintegrators as well as the active ingredients. Typical diluents include, for example, various types of starch, lactose, mannitol, kaolin, calcium phosphate or sulfate, inorganic salts such as sodium chloride and powdered sugar. Powdered cellulose derivatives are also useful. Natural and synthetic gums are also convenient, including acacia, alginates, methylcellulose, and/or polyvinylpyrrolidine. Polyethylene glycol, ethyl cellulose and waxes may also serve as binders. A lubricant may be necessary for a pellet formulation to prevent the pellet and punches from sticking in the die. The lubricant may be chosen from such slippery solids as talc, magnesium and calcium stearate, stearic acid and/or hydrogenated vegetable oils. Typically, the implant or pellet will have an implant or pellet hardness in a range of from about 6 Kg/N to about 10 Kg/N, preferably from about 7 Kg/N to about 9 Kg/N, most preferable about 8 Kg/N and all such dosage forms within this range are expressly provided for herein.

By compressing the formulation into a solid dosage form such as an implant in the form of pellet for subcutaneous administration, a sustained release multi-phasic concentration pattern as described herein may be obtained. Knowing that such a release pattern of an androgenic agent and aromatase inhibitor may be obtained, a person of ordinary skill in the art will be able to utilise different ingredients in the formulation in view of the disclosures provided herein and provide such pharmaceutical formulations in accordance with the present disclosure.

In certain embodiments, the implant or pellet may be inserted into the subcutaneous fat of the subject's pelvis, the subcutaneous fat of the subject's breast, the subcutaneous fat of the subject's buttocks, the subcutaneous fat of the subject's abdomen or combinations thereof. In certain embodiments, the implant or pellet may be inserted into the subcutaneous fat of the subject's lower abdominal wall. In certain embodiments, the implant or pellet may be inserted into the subcutaneous fat of the subject's upper gluteal region.

As will be understood, the androgenic agent and aromatase inhibitor may be provided in pharmaceutical formulations other than for subcutaneous administration either together in the same formulation or in separate formulations for use in combination treatments as described herein, such formulations comprising one or more of suitable filler(s), lubricants, binders, disintergrants and/or pharmaceutically acceptable carriers or excipients as described above or used in the provision of pharmaceutical formulations for the desired route of administration and/or for obtaining the desired release pattern (e.g., a sustained release multi-phasic release pattern) of the active(s).

In certain embodiments, the androgenic agent, the aromatase inhibitor, or pharmaceutical formulation comprising a combination of the same, may be provided in the form of an article of manufacture, such as a kit, which includes the active ingredients therein, or the active ingredients in suitable pharmaceutical formulations, packaged for distribution. Kits may additionally include instructions for using the kit components in one or more of the disclosed methods. Instructions may include instructions for practicing one or more of the disclosed methods. Thus, for example, a kit may include an androgenic agent or an aromatase inhibitor in a pharmaceutical formulation in a container, pack, or dispenser together with instructions for administration to a human subject. Instructions may additionally include indications of a satisfactory clinical endpoint or any adverse symptoms that may occur or any additional information required by the Food and Drug Administration for use in humans.

The instructions may be on "printed matter," e.g., on paper or cardboard within the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, and hybrids of these such as magnetic/optical storage media.

While the present disclosure has been described in terms of certain exemplary embodiments in order to facilitate a better understanding of the present disclosure, it should be appreciated that various modifications may be made without departing from the principles of the disclosed herein. Therefore, the inventions should be understood to include such modifications within its scope.

EXAMPLES

Example 1: A Single Dose Trial to Evaluate the Pharmacokinetics of Testosterone and Anastrozole from a Subcutaneous Testosterone and Anastrozole Implant, 80 mg/4 mg (T+Ai) in Women Pharmacokinetic analysis was undertaken on a subcutaneous testosterone 80 g and anastrozole 4 mg implant in 11 healthy volunteers with high mammographic breast density. This study evaluated the patterns for both anastrozole and testosterone and permitted modeling of the pharmacokinetics of this exemplary implant in order to demonstrate a pattern and end organ pharmacodynamic response where it is known that there is an excess of aromatase activity, i.e., in the tissue of women with high mammographic breast density. This is evaluated by direct measurement of breast tissue elasticity which is related to mammographic breast density.

Ultrasound evaluation of pellet dissolution was undertaken to demonstrate how input dissolution comprehensive analysis of reproductive hormones were undertaken to evaluate the potential impact on hypothalamic-pituitary function.

Primary Objectives:

To evaluate the pharmacokinetic characteristics of testosterone following a single dose of T+Ai by subcutaneous implantation.

To evaluate the pharmacokinetic characteristics of anastrozole following a single dose of T+Ai by subcutaneous implantation.

Secondary Objective

To explore the potential effect on breast tissue elasticity as assessed by shear wave ultrasound.

Implant Preparation: Testosterone-Anastrozole Pellets

Pellets for subcutaneous insertion were prepared by compressing sterile non-micronized testosterone, anastrozole and stearic acid in an 80:4:2 ratio into a 5 mm diameter cylindrical die. The pellets are transferred to a sterile 5 ml amber vial covered with sterile cotton wool and sealed with a rubber stopper and aluminium rip seal which is crimped. The vials are sterilized by gamma irradiation at 25 KGy. Testosterone non-micronized and anastrozole, USP grade, were obtained from Azelis (Brookvale, NSW). The stearic acid, NF quality, was obtained from Medisca (Mascot, NSW). The steps for producing these pellets are outlined below:

1. Blend titration of testosterone (non-micronized), anastrozole, and stearic acid by mechanical means for 2 hours.
2. Mix titration thoroughly.
3. Compress pellets with a press that produces pellet hardness of 8 Kg/N
4. The pellet is stored in amber glass 5 ml vial, pellet cushioned with sterile cotton wool.
5. The stored pellet is gamma sterilize at 25 KyG.
6. Properly label pellets.
7. Store in a cool, dry place (room temperature; 20-25° C., 66-78° F.).

Methodology

Pre-menopausal women with high Mammographic Breast Density (MBD) was selected for the study. Following the successful screening, participants came to the Wellend Clinic South Australia for dosing. The participants were to be dosed while in the luteal phase of their menstrual cycle to avoid the highly changing hormonal environment of the follicular phase. Following insertion of the implant, PK blood sampling was carried out for a duration of three months. Briefly, samples were taken repeatedly on the day of dosing, daily during the first week, weekly for the next four weeks and every second week during the last eight weeks, for a total sampling period of three months. After assessments had been completed on the last day of assessments, Day 85, the trial concluded.

To determine whether the selected pharmacokinetic (PK) sampling schedule provided an adequate description of the serum/plasma concentration time profile of T+Ai, after the Day 29 blood samples had been collected from the first two participants, the samples were analysed for testosterone, dihydrotestosterone, and anastrozole. The sampling schedule was revised with the addition of one blood sample (at 6 hours post-dose), and no adjustment of the timing of existing time points. The duration of sampling was not extended.

In summary, following dosing on Day 1, blood samples were taken pre-dose (within one hour of dosing) and at 1, 2, 4, 6, 8 and 12 hours. Participants returned for a blood sample to be taken at 9 am in the morning on Days 2, 3, 4, 5, 8, 15, 22, 29, 43, 57, 71 and 85.

A total of 11 subjects were dosed and included in the safety analysis set. Eleven subjects were included in the PK analysis set. Women were aged between 35 and 55 years of age, Body Mass Index (BMI) range of 20-30 kg/m². The demographics of the participants are shown in Table 1.

TABLE 1

Summary of Participant Demographic Data (Safety Analysis Set)

| Demographic Parameter (Units) | Number of Participants | Average | Standard Deviation | Median | Minimum | Maximum |
| --- | --- | --- | --- | --- | --- | --- |
| Gender (Female) | 11 | | | | | |
| Age (years) | 11 | 41.5 | 3.7 | 40 | 37 | 49 |
| Weight (kg) | 11 | 67.87 | 10.27 | 64.9 | 50 | 83.4 |
| Height (m) | 11 | 1.673 | 0.066 | 1.67 | 1.54 | 1.79 |
| BMI (kg/m^2) | 11 | 24.14 | 2.26 | 23.4 | 20.8 | 27.4 |
| Race (White) | 10 | | | | | |
| Race (White/Asian) | 1 | | | | | |
| Ethnicity (Not Hispanic or Latino) | 11 | | | | | |

PK Results

A summary of the PK parameters for plasma anastrozole and serum testosterone is presented in Table 2 and illustrated in FIGS. 1 to 6.

TABLE 2

Summary of Plasma Anastrozole and Serum Testosterone PK Parameters

| Analyte | Median (Range) | | Arithmetic Mean (CV %) | | | | |
|---|---|---|---|---|---|---|---|
| | $T_{max}$ (hr) | $C_{max}$ (ng/mL) | $AUC_{last}$ (hr * ng/mL) | $t_{1/2}$ (days) | $AUC_{0-inf}$ (hr * ng/mL) | CL/F (L/hr) | $AUC_{84d}$ (hr * ng/mL) |
| Plasma Anastrozole (n = 11) | 48.6 (23.6-72.5) | 5.30 (14%) | 88.0 (25%) | 13.6 (31%) | 93.2 (25%) | 1.88 (22%) | — |
| Serum Testosterone (n = 11) | 8.0 (5.9-12.0) | 4.08 (21%) | | 42.8 (34%) | — | — | 127.2 (23%) |

With regard to pharmacokinetics, median $T_{max}$ for plasma anastrozole was 2 days post-dose (range 1-3 days), with average $C_{max}$=5.30 ng/mL, and an average terminal half-life of 14 days. Concentrations were below the limit of quantitation (0.1 ng/mL) in most participants after 12 weeks. The half-life of 14 days observed from T+Ai is considerably longer than the 2 days half-life stated for oral anastrozole, confirming that the T+Ai product acted as a sustained-release formulation. As the objective of this therapy is to reduce aromatisation of T at the insertion site (i.e., subcutaneous adipose where the aromatase level is average and in tissues where the aromatase is high) the minimal effective dose is given compared to when treating breast cancer where total body aromatase inhibition is sought to maximise anti-neoplastic effect. The IC50 for anastrozole in tissue over-expressing aromatase (such MCF7 breast cancer cell line and JEG3 human choriocarcinoma cell line) is 3.62 and 5.66 nM respectively. The $C_{max}$=5.3 ng/mL (18.07 nM) would, therefore, cover the initial higher $C_{max}$=4.1 ng/mL of T with a sustained lower level of anastrozole with the decline in T level. Accordingly, the use of 4 mg of anastrozole in the pellet achieved a concentration required for an IC50 of aromatase sufficient to inhibit the aromatase enzyme in the target tissue. In contrast, a dose of 2 mg would not have been sufficient.

For serum testosterone, the median $T_{max}$ was 8 hours post-dose (range 6-12 hours), with average $C_{max}$=4.1 ng/mL, compared with average at baseline of 0.2 ng/mL. There was a second lower peak at 2-3 weeks. Increase in testosterone compared with baseline was sustained in participants at 12 weeks, with an average concentration of 0.8 ng/mL. Serum dihydrotestosterone was not measurable in most samples, with $T_{max}$ at 2-3 days post-dose in participants with measurable maximal values. This example shows that the pellets after subcutaneous insertion exhibited a pattern.

Example 2: Testosterone and Anastrozole Combination Therapy for MBD Reduction in Woman This example provides an analysis of the used testosterone and anastrozole combination therapy for mammographic breast density (MBD) reduction in woman. The study was conducted at the Wellend Clinic (Burnside War Memorial Hospital, Adelaide, South Australia). The major indication for therapeutic intervention was one or more of the following: perimenopausal hormone dysfunction, high MBD, which is considered a factor in reducing breast cancer (BC) risk.

All 652 patients were female, with an average age at the time of first T+Ai implant of 52 years (ranging from 23 to 79 years).

Reduction of MBD/BC risk was the primary indication for treatment in 89 patients (14%), assistance with hormonal dysfunction in 334 patients (51%) and both indications in 177 patients (27%). The primary indication was not provided for 52 patients.

A history of BC was noted in 90 patients (14% of patients with non-missing responses for BC history). The type of BC was noted for 20 patients—14 had in-situ type BC, and six had invasive type BC.

Estrogen based concomitant medication use was noted for 222 patients (34%), of which the majority was in the form of topical medications (n=192).

At the time of the data cut in July 2017, 365 patients (56%) were continuing to receive T+Ai therapy. One patient did not have disposition information recorded, while the remaining 286 patients had stopped T+Ai therapy. The most frequent reason for stopping T+Ai therapy was lost-to-follow-up (n=123), followed by subject decision to cease therapy (n=46), cost of therapy (n=30), subject feeling T+Ai therapy was not working (n=28) and primary care physician advising the patient that T+Ai therapy was complete (n=25).

Measurement of Efficacy

Summary statistics for continuous variable measurements (including % VBD and AVBD measures of MBD) obtained from mammograms. As mammograms were not scheduled for specific time-points, a visit windowing system was applied to the data in order to provide a specific data value to a specific time-point. The windows chosen were as follows:

Six months (180 days after first T+Ai implant+/−60 days)
One year (365 days after first T+AI implant+/−180 days)
Two years (730 days after first T+AI implant+/−180 days)
Three years (1095 days after first T+AI implant+/−180 days)
Four years (1460 days after first T+AI implant+/−180 days)

Drug Dose and Relationship to % VBD Response

To examine the impact of T+Ai intervention on MBD as measured by % VBD, a subset of patients who had mammograms both before and subsequent to the commencement of treatment was considered. For this subset of patients (n=142), the change from baseline MBD was used as the outcome measure in a mixed model analysis using SAS® PROC MIXED. This procedure allows for the potential of individual patients to contribute more than one mammogram following commencement of T+Ai treatment (repeated measures analysis), as well as examining different covariance patterns amongst the data.

From the data set provided for analysis, the following independent (explanatory) variables were used to examine their impact on the change in MBD:

i. Days since first implant
ii. Baseline % VBD MBD measurement (the value closest to, but not later iii. than, the first T+Ai implant)
iii. Cumulative testosterone dose (mg) across the entire study (stratified into <500 mg, 500 mg to <700 mg, and 700 mg+).
iv. Cumulative anastrozole dose (mg) across the entire study (as a continuous covariate)
v. Age (in years) at first implant
vi. Machine type (GE or Hologic machine)
vii. Radiation dose at the mammogram
viii. Compression pressure at the mammogram
ix. History of breast cancer (yes or no)
x. Use of concomitant estrogen medications (yes or no)
xi. Interaction term between days since first implant and cumulative dose of testosterone strata.

The last interaction term listed above allows for the fitting of different slopes to each of the testosterone dose strata to see if potential differences exist across the strata.

The following syntax was used in SAS to fit the model:
proc mixed data=mmg3;
class TESTO_GP SUBJIDC MMG_MACH_N BCA_HIST_N E2_USED_N;
model CHANGE_MMG_RESULT=MMG_DAY BASE_MMG_RESULT TESTO_GP MMG_MACH_N BCA_HIST_N E2_USED_N SUM_ANAST MMG_RAD_DOSE_N MMG_COMP_PRES_N MMG_DAY*TESTO_GP/ddfm=kr cl s;
random INT MMG_DAY/subject=SUBJIDC type=un;
lsmeans TESTO_GP/at MMG_DAY=365 cl;
lsmeans TESTO_GP/at MMG_DAY=730 cl;
lsmeans TESTO_GP/at MMG_DAY=1095 cl;
lsmestimate TESTO_GP 'Across all dose levels at 1 yr' 1 1 1/divisor=3 at MMG_DAY=365 cl;
lsmestimate TESTO_GP 'Across all dose levels at 2 yr' 1 1 1/divisor=3 at MMG_DAY=730 cl;
lsmestimate TESTO_GP 'Across all dose levels at 3 yr' 1 1 1/divisor=3 at MMG_DAY=1095 cl;
format TESTO_GP testo. BCA_HIST_N E2_USED_N yesno. MMG_MACH_N machine;
run.

Each of the terms in the model statement represents an item from the previous bullet list. The random statement is used to account for repeated measurements taken over time within each patient. An unstructured covariance structure was used as it provided a slightly better fit when compared to compound symmetry (CS) and autoregressive (AR1) options in SAS®. LSMEANS and LSMESTIMATE statements were used to estimate the change from baseline in MBD by testosterone dose strata, at 1-year, 2-years, and 3-years. Table 3 presents parameter estimates obtained from the model.

Statistically significant findings were noted for days since first T+Ai implant, and the interaction between days since first T+Ai implant and cumulative testosterone strata. Specifically, larger decreases in MBD were noted over time for patients with accumulated testosterone dosing of over 500 mg compared with patients with <500 mg. Cumulative anastrozole dosing also approached significance levels of 0.05 (p=0.06), with estimates also indicating a larger reduction in MBD for higher accumulated anastrozole doses. Baseline % VBD was also statistically significant, with higher baseline scores having larger observed changes (reduction in % VBD).

TABLE 3

SAS PROC MIXED model estimates for change from baseline in MBD

| Explanatory variable | Category comparison | Estimate | p-value | Lower 95% CI | Upper 95% CI |
| --- | --- | --- | --- | --- | --- |
| Intercept | N/A | 2.4813 | 0.1799 | −1.1552 | 6.1178 |
| Days since first T + Ai implant | N/A | 0.001084 | 0.3692 | −0.00131 | 0.00348 |
| Baseline % VBD MBD measurement | N/A | −0.1527 | <.0001 | −0.2248 | −0.08049 |
| Cumulative testosterone strata | 500 to <700 mg versus <500 mg | 1.446 | 0.2331 | −0.9479 | 3.8399 |
| Cumulative testosterone strata | 700+ mg versus <500 mg | 0.6022 | 0.683 | −2.3086 | 3.513 |
| Mammogram machine type (broad category) | GE versus Hologic | 0.07725 | 0.8821 | −0.9491 | 1.1036 |
| BC history | No versus Yes | 0.1302 | 0.8717 | −1.4632 | 1.7236 |
| Concomitant estrogen medication use | No versus Yes | −0.2762 | 0.6333 | −1.4196 | 0.8673 |
| Cumulative anastrozole dose (mg) | N/A | −0.07478 | 0.3034 | −0.218 | 0.06846 |
| Mammogram radiation dose | N/A | −0.2979 | 0.3998 | −0.9944 | 0.3985 |
| Mammogram compression pressure | N/A | −0.02976 | 0.6683 | −0.1666 | 0.1071 |
| Interaction: Days since first T + Ai implant by Cumulative testosterone strata | 500 to <700 mg versus <500 mg | −0.00264 | 0.1515 | −0.00628 | 0.001006 |
| Interaction: Days since first T + Ai implant by Cumulative testosterone strata | 700+ mg versus <500 mg | −0.00236 | 0.1764 | −0.00585 | 0.00112 |

Least squares mean of the change from baseline in % VBD measure of MBD, by cumulative testosterone strata, were estimated at 1 year, 2 years, and 3 years. Table 4 below presents the results from the model. Rows highlighted show estimated changes from baseline that are statistically significantly different from zero (p<0.05). An analysis of change from baseline in % VBD least squares mean estimates at one, two and three years.

TABLE 4

Least squares estimated change from baseline in MBD, by cumulative testosterone dose and time since first implant

| Cumulative testosterone dose group | Time since first implant | Least squares mean estimate | Lower 95% CI | Upper 95% CI | p-value |
|---|---|---|---|---|---|
| <500 mg | 1 year | −1.6085 | −2.8628 | −0.3542 | 0.0123 |
| <500 mg | 2 years | −1.213 | −2.6838 | 0.2579 | 0.1053 |
| <500 mg | 3 years | −0.8174 | −2.8829 | 1.248 | 0.4349 |
| 500 to <700 mg | 1 year | −1.1249 | −2.4165 | 0.1668 | 0.0872 |
| 500 to <700 mg | 2 years | −1.6916 | −3.0057 | −0.3775 | 0.0121 |
| 500 to <700 mg | 3 years | −2.2584 | −4.2275 | −0.2893 | 0.0251 |
| 700+ mg | 1 year | −1.8688 | −3.6155 | −0.1222 | 0.0362 |
| 700+ mg | 2 years | −2.3358 | −3.8817 | −0.7899 | 0.0034 |
| 700+ mg | 3 years | −2.8028 | −4.6566 | −0.949 | 0.0035 |

Efficacy of T+Ai in Reduction of MBD as Measured by AVBD

In addition to the analysis conducted using % VBD MBD measurement, a complementary analysis was undertaken using the same model discussed above in this example, with a change from baseline Absolute Volumetric Breast Density (AVBD) as the dependent variable. The only other change to the list of dependent variables used was to replace baseline % VBD with baseline AVBD. Least squares mean estimates from the AVBD model are displayed in Table 5 below. Again, statistically significant values are shown in the highlighted rows. The only values of significance were those in the 700 mg+ cumulative testosterone group, at two and three years post-first T+Ai implant. The change from baseline AVBD estimates was −22 cm$^3$ and −60 cm$^3$, at two years and three years respectively.

TABLE 5

Least squares estimated change from baseline in AVBD, by cumulative 15 testosterone dose and time since first implant

| Cumulative testosterone dose group | Time since first implant | Least squares mean estimate | Lower 95% CI | Upper 95% CI | p-value |
|---|---|---|---|---|---|
| <500 mg | 1 year | −12.6001 | −25.7233 | 0.523 | 0.0597 |
| <500 mg | 2 years | −11.2073 | −28.3175 | 5.9029 | 0.1975 |
| <500 mg | 3 years | −9.8144 | −35.6603 | 16.0314 | 0.4537 |
| 500 to <700 mg | 1 year | 0.2747 | −12.2756 | 12.8251 | 0.9652 |
| 500 to <700 mg | 2 years | −4.1993 | −19.8209 | 11.4223 | 0.595 |
| 500 to <700 mg | 3 years | −8.6734 | −34.0633 | 16.7166 | 0.4985 |
| 700+ mg | 1 year | −7.7803 | −26.2516 | 10.691 | 0.4052 |
| 700+ mg | 2 years | −21.9964 | −39.4828 | −4.5101 | 0.0142 |
| 700+ mg | 3 years | −36.2126 | −59.7196 | −12.7056 | 0.0029 |

Efficacy Conclusions

Using mammogram information obtained from 142 patients with mammograms taken both pre- and post-commencement of T+Ai therapy, there were statistically significant changes from baseline MBD measurement of both % VBD and AVBD following intervention with T+Ai therapy.

When MBD was measured by % VBD, patients with cumulative testosterone dosing of 700 mg+, the 1-year post-commencement of therapy estimated change was −1.87, the 2-year post-commencement of therapy estimated change was −2.34, and the 3-year post-commencement of therapy estimated change was −2.82. For patients with cumulative testosterone dosing of 500-<700 mg, the 1-year post-therapy commencement estimated change was −1.12 (p=0.09), the 2-year post-therapy commencement estimated change was −1.69, and the 3-year post-therapy commencement estimated change was −2.26.

When MBD was measured by AVBD, the values of significance were those in the 700 mg+ cumulative testosterone group, at 2 and 3 years post-first T+Ai implant. The change from baseline AVBD estimates was −22 cm$^3$ and −60 cm$^3$, at 2 years and 3 years respectively.

The majority of women in example 2 received a dose of anastrozole of 2 mg per implant. This dose was chosen in order to attempt to maintain as low a dose as possible in order to avoid side-effects. Although efficacy at this dosing was effective, Example 2 shows that cumulative anastrozole dosing is a variable of interest when assessing change in MBD (p=0.06). Larger values of cumulative anastrozole dose were associated with larger changes from baseline (decreases from baseline) in MBD. Surprisingly and unexpectedly the PK and PD of anastrozole shown in Example 1 shows that a larger dose of anastrozole (4 mg per implant) may be used that achieves efficacy and also avoids, or minimizes, side effects associated with the aromatase inhibitors disclosed herein.

Example 3: Pharmacokinetics Profile of Anastrozole Using a Modelling Approach

Figure 8A:
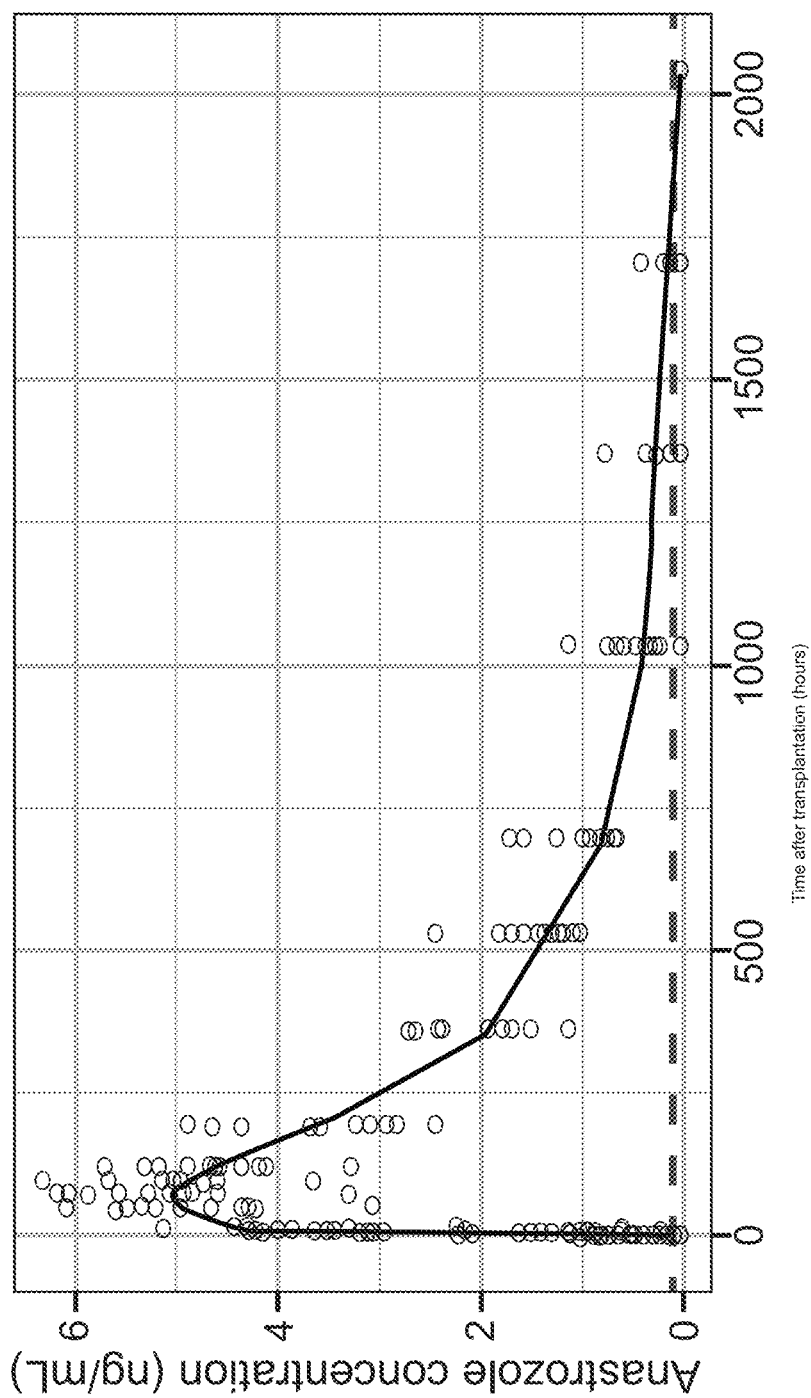
FIGS. 8A-B illustrate the plasma anastrozole concentration post implantation, according to certain embodiments.
Figure 8B:
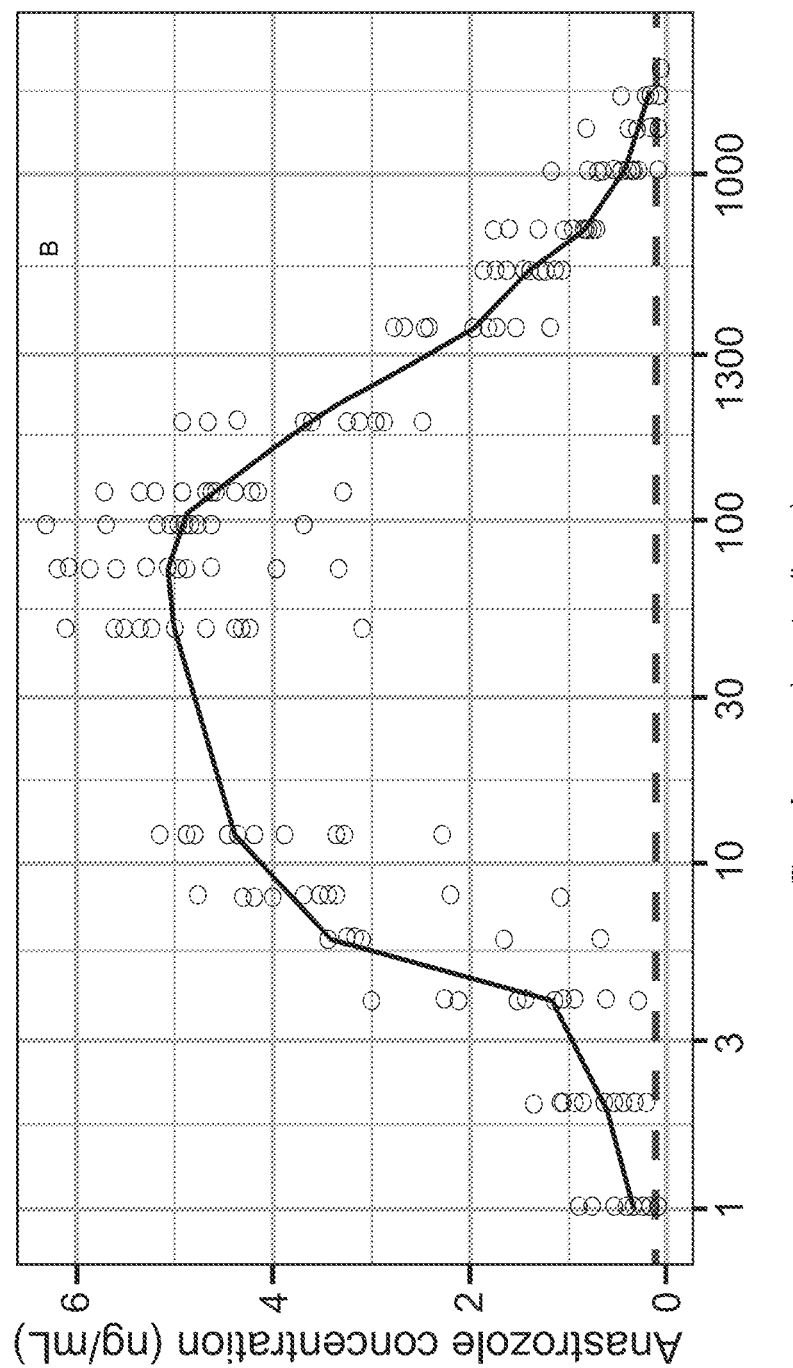
Figure 9:
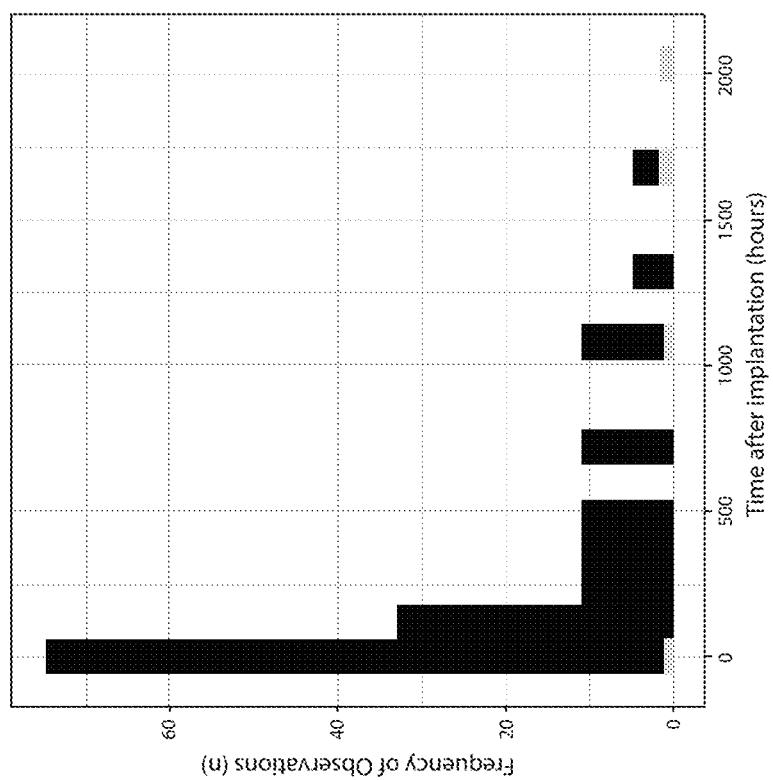
FIG. 9 shows the frequency of observation post implantation in Example 3.

This example provides an analysis of a pharmacokinetic profile of anastrozole using a modelling approach in order to evaluate an optimal input function to describe absorption of the trial set forth in Example 1. Table 6 sets forth the sampling schedule for anastrozole and testosterone. Blood samples of at least 8 mL were collected for serum testosterone/DHT and plasma anastrozole by venipuncture at each time point specified in table 6. FIGS. 7A-B illustrate the anastrozole absorption rates. Data in these figures are presented as mean+/−standard deviation. FIG. 7A shows the Y axis on the log scale. FIG. 7B shows the Y axis on a linear scale. The figures were produced using the pellet absorption data summarized in Table 2 of Example 1. The percentage change from baseline was calculated for the average volume and plotted against time in months. FIGS. 8A-B plot the plasma anastrozole concentration post implantation. In FIG. 8A, the data on the X axis is plotted in time (hours) after transplantation. In FIG. 8B the X axis is on a log scale. In FIGS. 8A-B, the open circles equal observed data, the black line equals median PK profile, and the dashed dark grey line equals lower limit of quantification (0.1 ng/mL). FIG. 9 shows the frequency of observation post implantation. Approximately fifteen percent of the data was below the lower limit of quantification (BLQ). The BLQ concentrations were observed either pre-dose or after 1000 hours post implantation.

TABLE 6

| Day 1 | Other Days |
|---|---|
| 1, 2, 4, 6, 8 and 12 hours post implantation | Days 2, 3, 4, 5, 8, 15, 22, 29, 43, 57, 71 and 85 post implantation |

Figure 10:
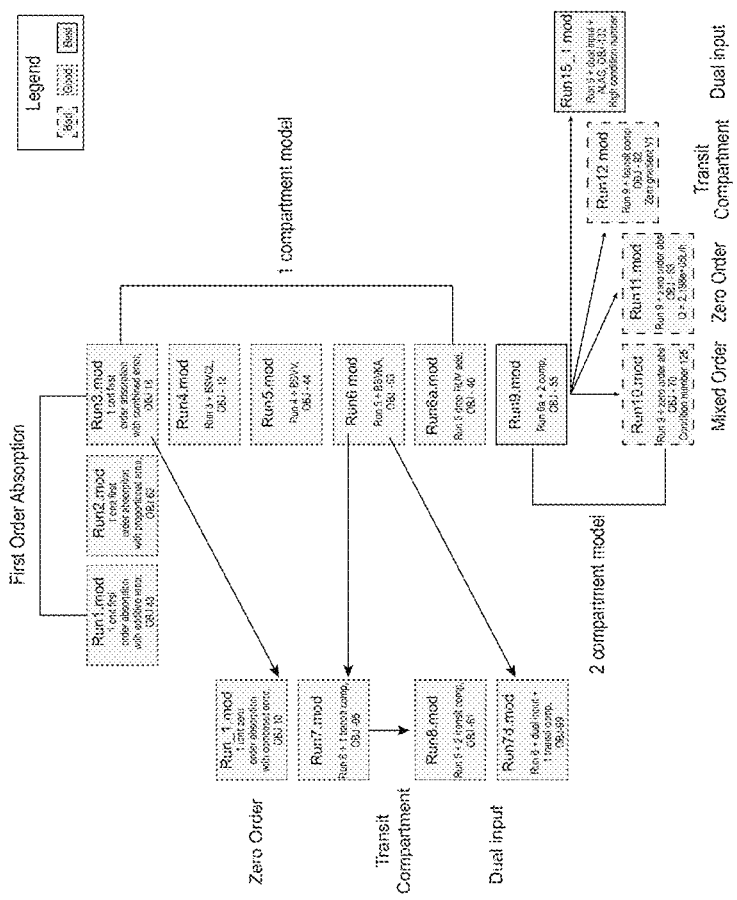
FIG. 10 illustrates an example of a flow chart of models tested in Example 3.
Figure 11:
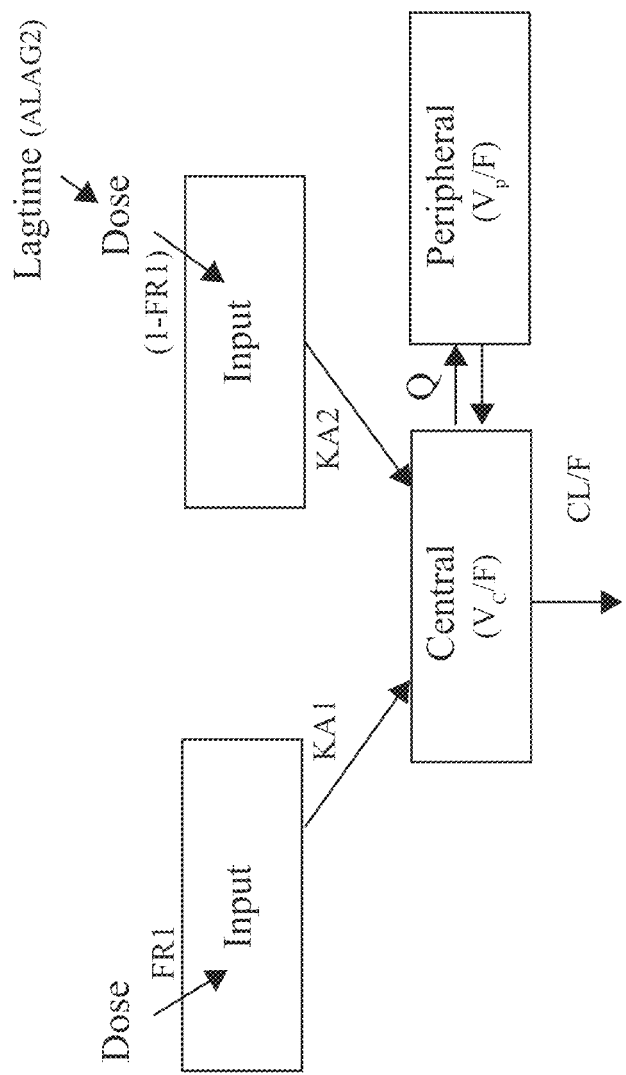
FIG. 11 shows the final structure model used in Example 3.

In this example, a population modelling approach was used to characterise the PK of anastrozole. One and two compartment models were fitted to the data. Several absorption models were tested such as first and zero order, mixed order, as well as transit compartments. Model selection was performed on the basis of statistical criteria (objective function) as well as visual inspection of diagnostic plots. FIG. 10 shows a flow chart of the models tested. FIG. 11 shows the final structure model used in this example. This example illustrates that the best model fitting the data was a two-compartment disposition model with absorption described by a dual input. Between-subject variability (BSV) was included on apparent clearance (CL/F), apparent volume of distribution for the central compartment ($V_c/F$) and the first-order absorption rate constant (KA). A proportional error model was used to describe residual unexplained variability (RUV).

Below Table 7 provides the parameter estimates of Anastrozole. Parameters were estimated with good precision (RSE<30%) with the exception of the between subject variability term on Vc/F, and apparent inter-compartmental clearance (Q/F), however, was considered acceptable given the data available. The model estimated value of CL/F was 1.77 L/h, which is comparable to the estimate from the NCA of 1.88 L/h demonstrated in Table 2 of Example 1.

TABLE 7

| Parameter Name | Estimated Value (% RSE) | BSV CV % (% RSE) |
|---|---|---|
| Apparent clearance (CL/F, L/hr) | 1.77 (6.9) | 21.9 (23.3) |
| Apparent central volume of distribution ($V_c$/F, L) | 672 (3.0) | 17.7 (30.9) |
| Inter-compartmental clearance (Q/F, L/hr) | 0.97 (57.5) | — |
| Apparent peripheral volume of distribution ($V_p$/F, L) | 106 (29.8) | — |
| Absorption rate constant (ka, /hr) first input | 0.119 (20.6) | 66.5 (12.9) |
| Absorption rate constant (ka, /hr) second input | 0.148 (20.5) | — |
| Fraction absorbed via second input | 0.5 FIX | — |
| Lagged time for second input (h) | 3.77 (9.7) | — |
| Residual unexplained variability (Proportional) | 16.8 (8.3) | — |

Figure 12A:
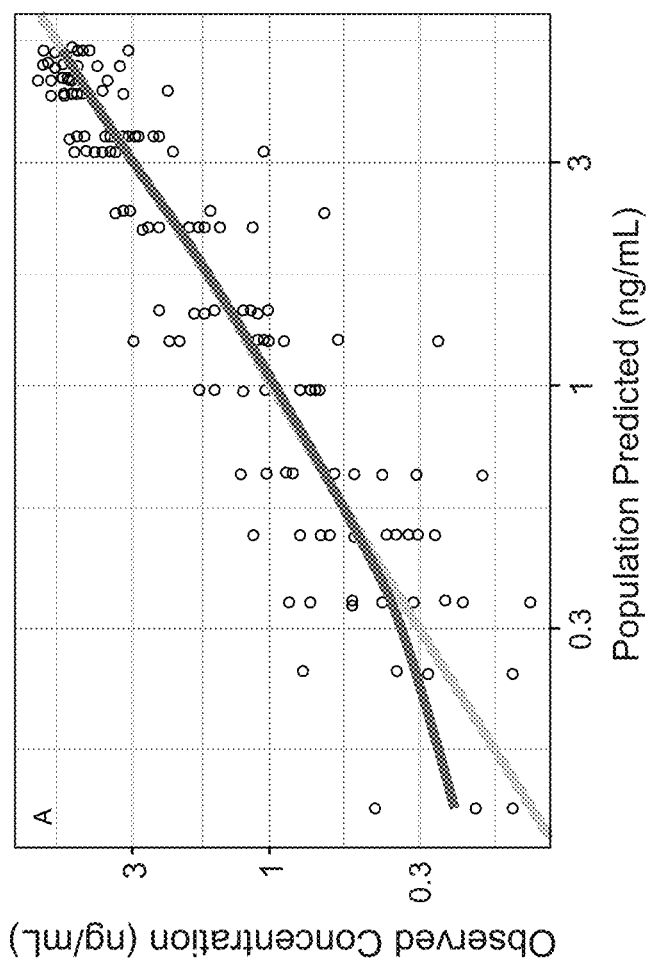
FIGS. 12A-B shows the population and individual predictions used in Example 3.
Figure 12B:
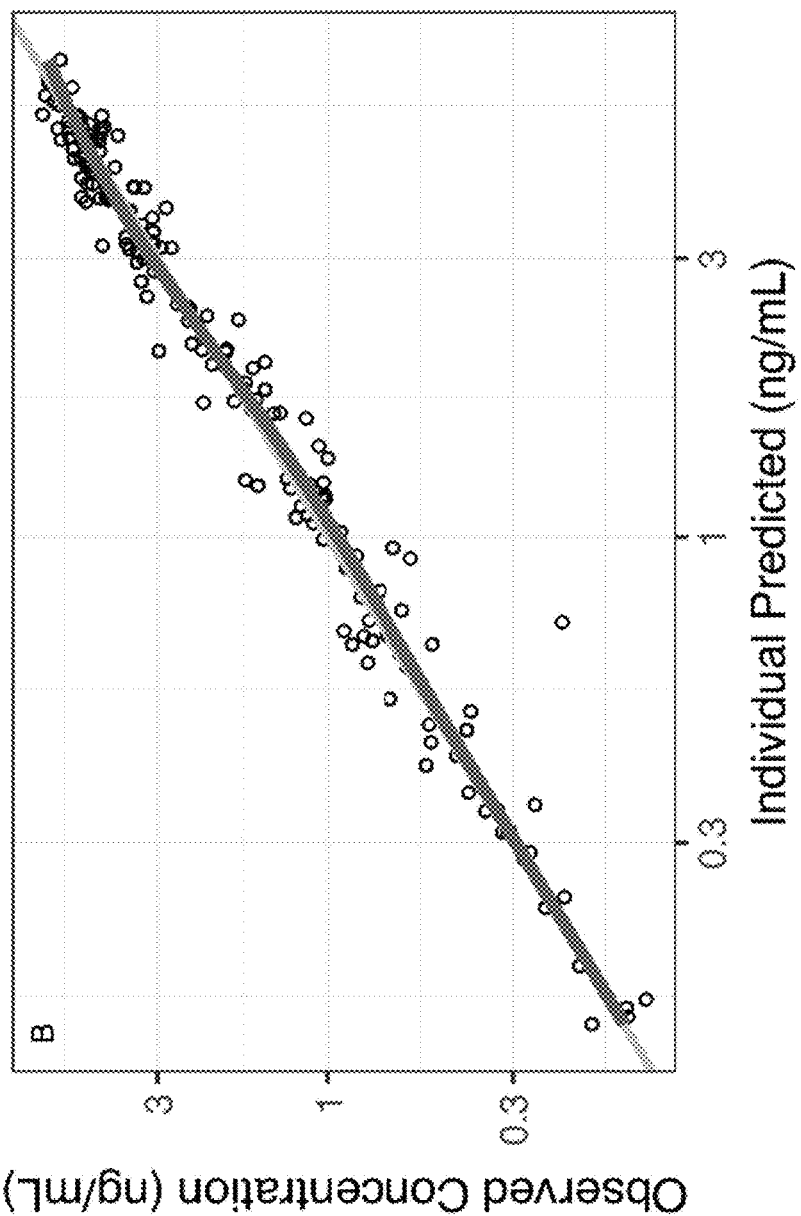
Figure 13A:
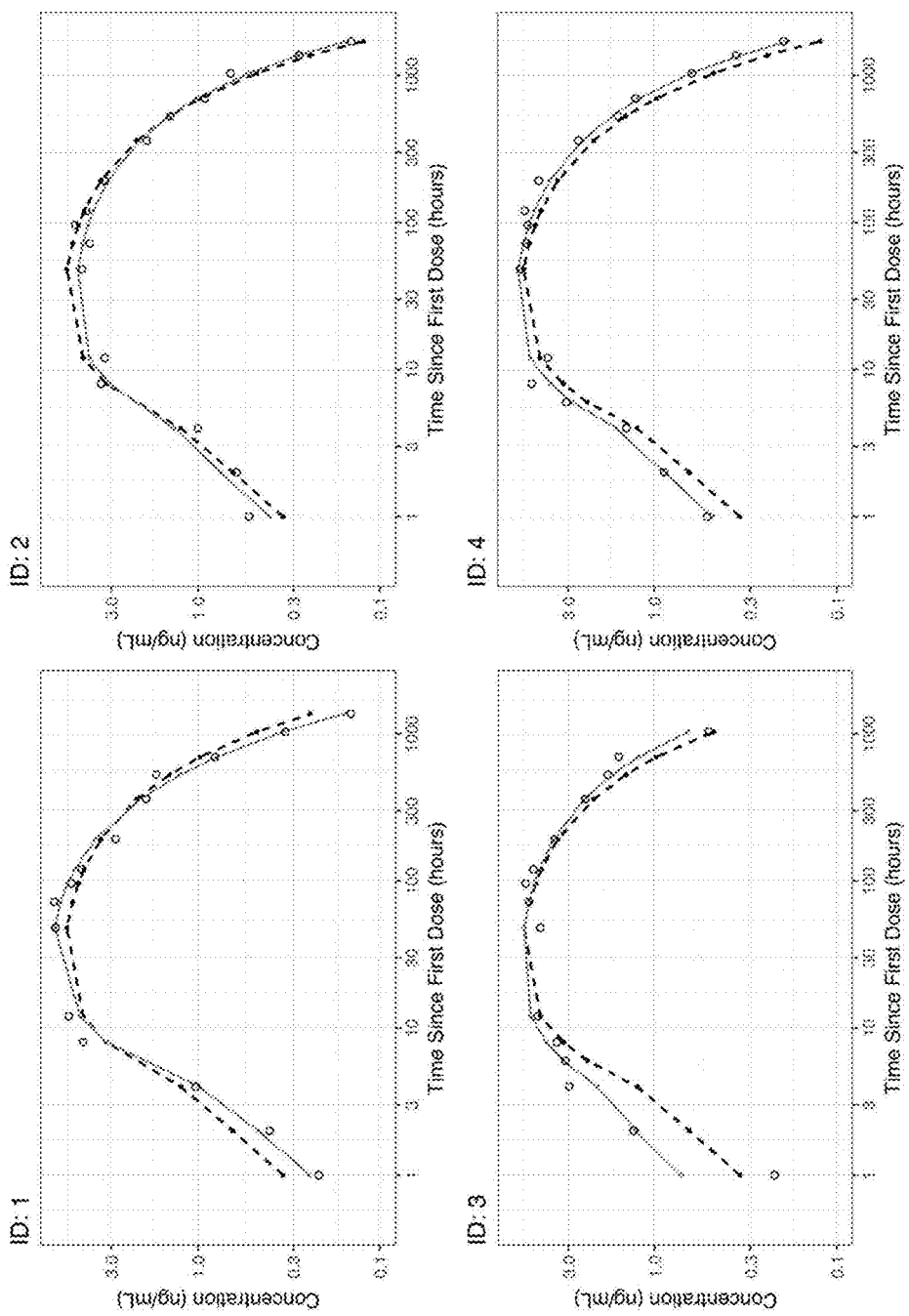
FIG. 13A-C illustrates 11 individual plots of observed and predicted plasma concentrations of anastrozole, according to certain embodiments.
Figure 13B:
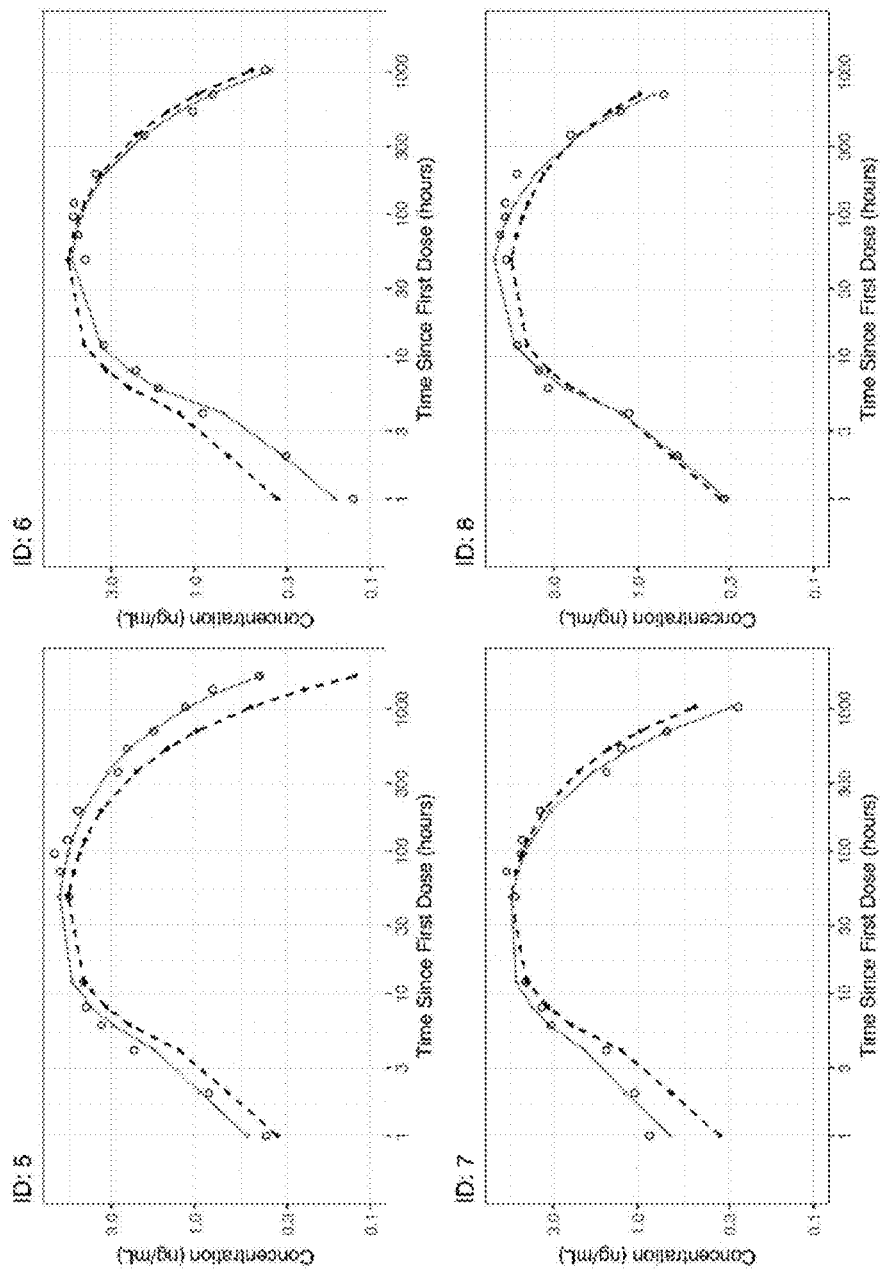
Figure 13C:
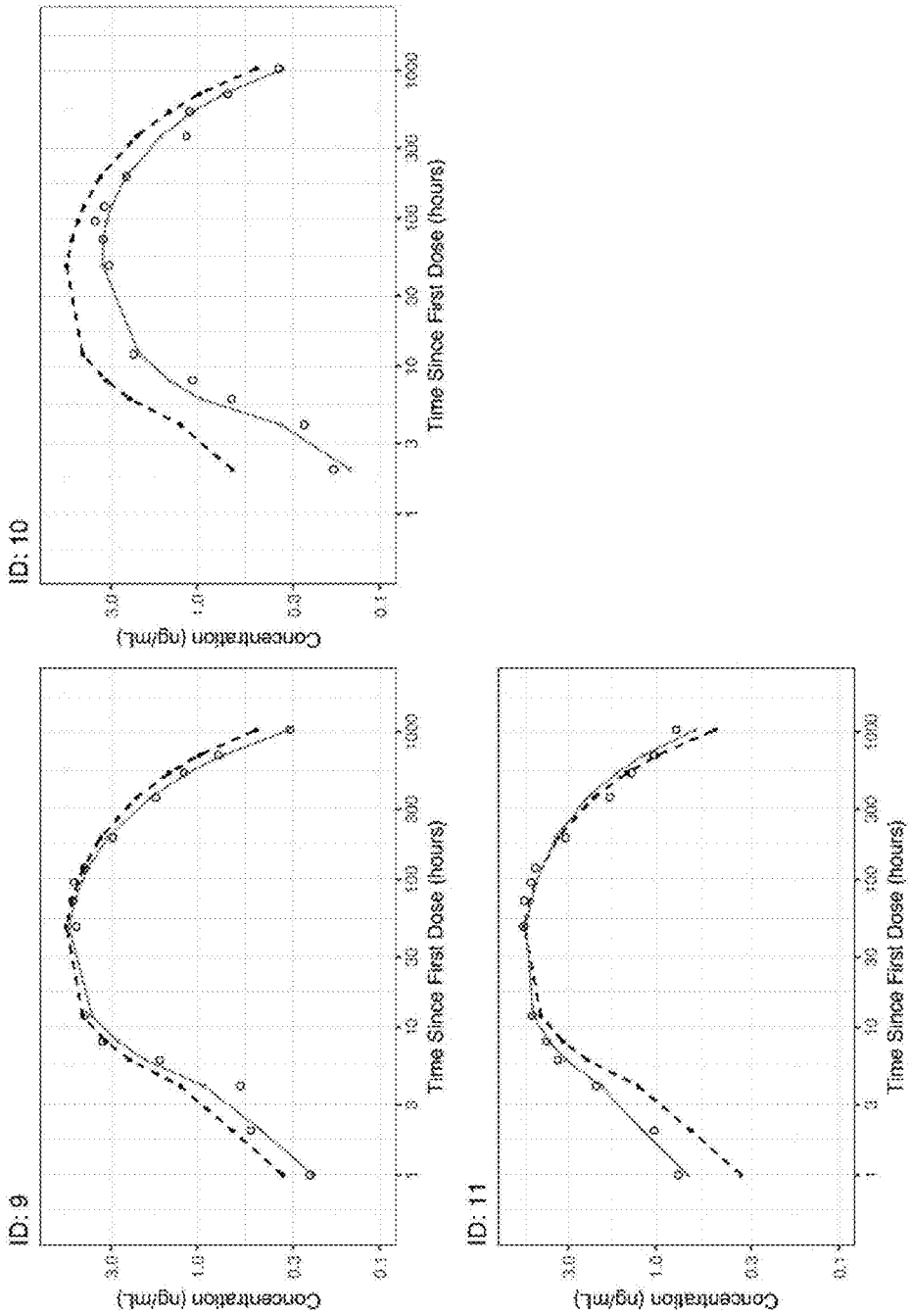

% RSE = % relative standard error,
BSV = between subject variability,
CV % = % coefficient of variation FIGS. 12A-B shows the population and individual predictions. FIG. 12A shows the population prediction. FIG. 12B shows the individual prediction. The light grey lines represent the line of identity and the dark grey lines show the trend in the data (Loess smooth). The tailing in the trend line for FIG. 12B is expected since the BLQ data are censored. Overall the model predicts the data well with minimal bias. Population predicted concentration is the representation of a typical patient. The individual predicted concentration is a post-Bayes/individualized prediction. FIG. 13(ID:1-11) shows the individual plots of observed and predicted plasma concentrations of anastrozole. The data was plotted at nominal times. The dashed black lines equal population model prediction, the solid grey lines equals individual model prediction, and the circles equals individual observed data. The final model was used to simulate 1000 replicates of the dataset to validate the model simulation characteristics. From the simulated data, the 95% CI around the median, and $10^{th}$ and $90^{th}$ prediction intervals were calculated. The median, $10^{th}$ and $90^{th}$ percentiles of the observed data was then overlaid on the simulated data to validate the model.

Figure 14:
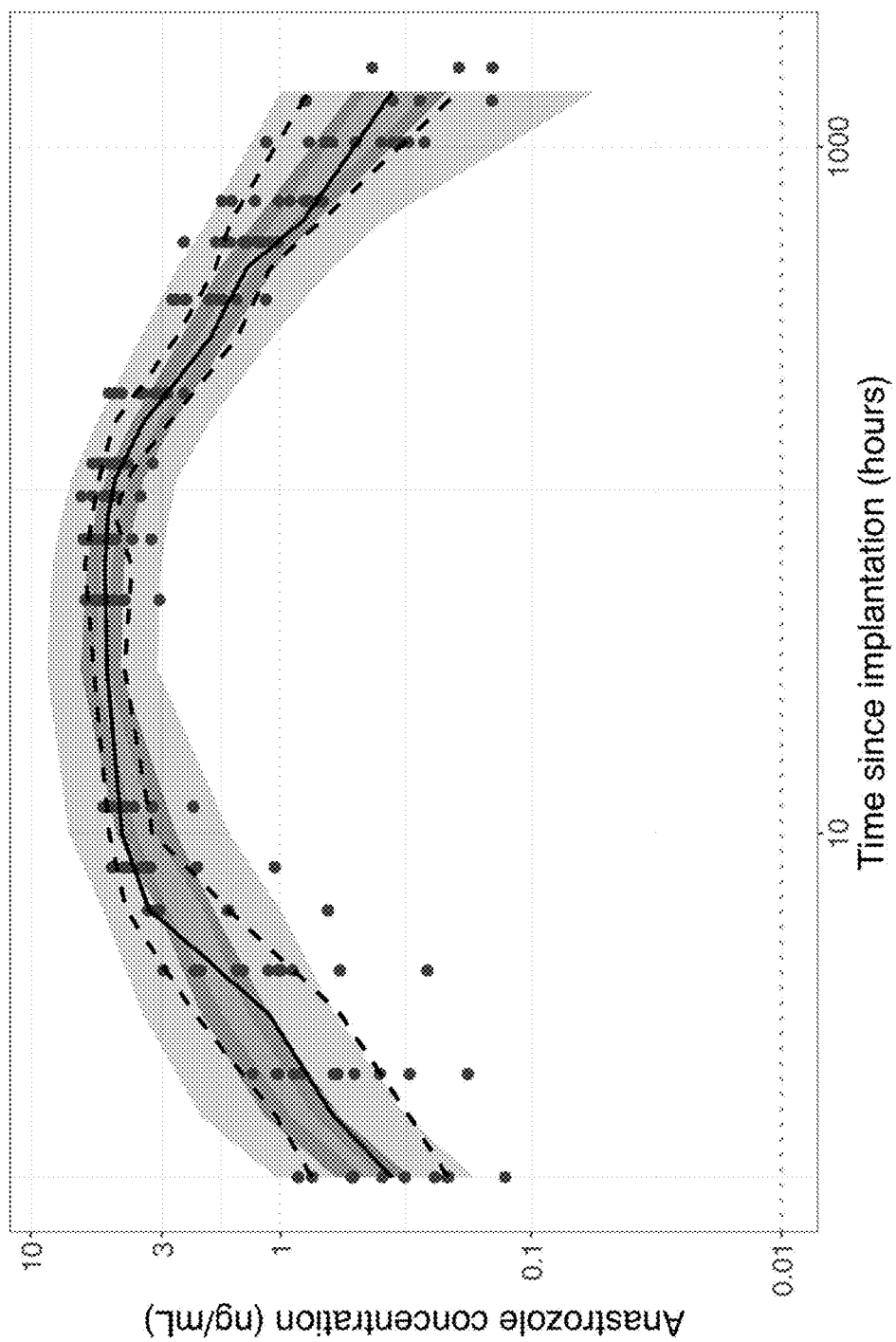
FIG. 14 shows a visual predictive check (VPC) of anastrozole concentration post implantation used in Example 3.

FIG. 14 shows a visual predictive check (VPC) of anastrozole concentration post implantation. The VPC shows that the observed data was captured well by the simulated data from the model. X-axis and Y-axis are on a log scale. Dashed black lines=observed $10^{th}$ and $90^{th}$ percentiles, solid black line=observed median, shaded grey area=80% prediction interval, light grey dotted line=lower limit of quantification.

Figure 15A:
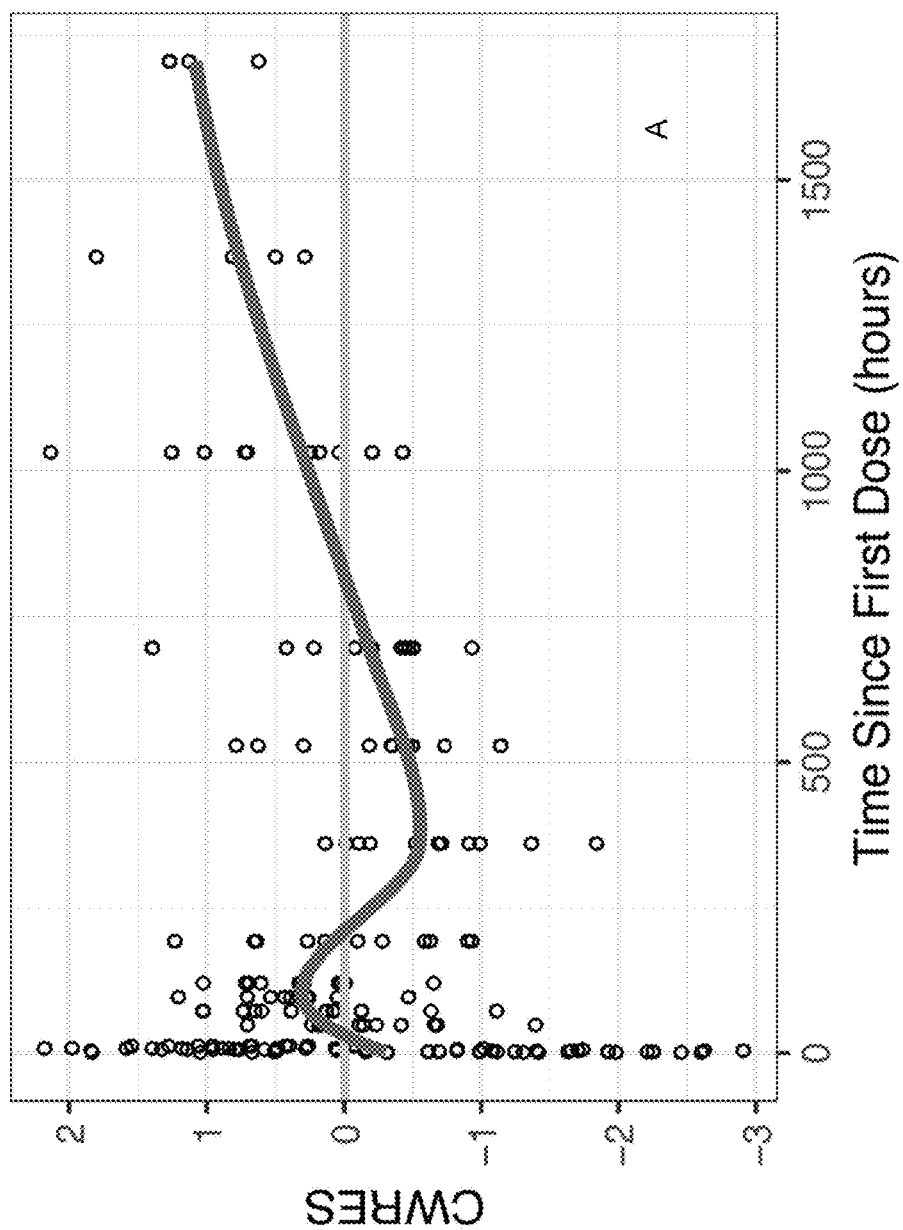
FIGS. 15A-B shows one versus two compartment model used in Example 3.
Figure 15B:
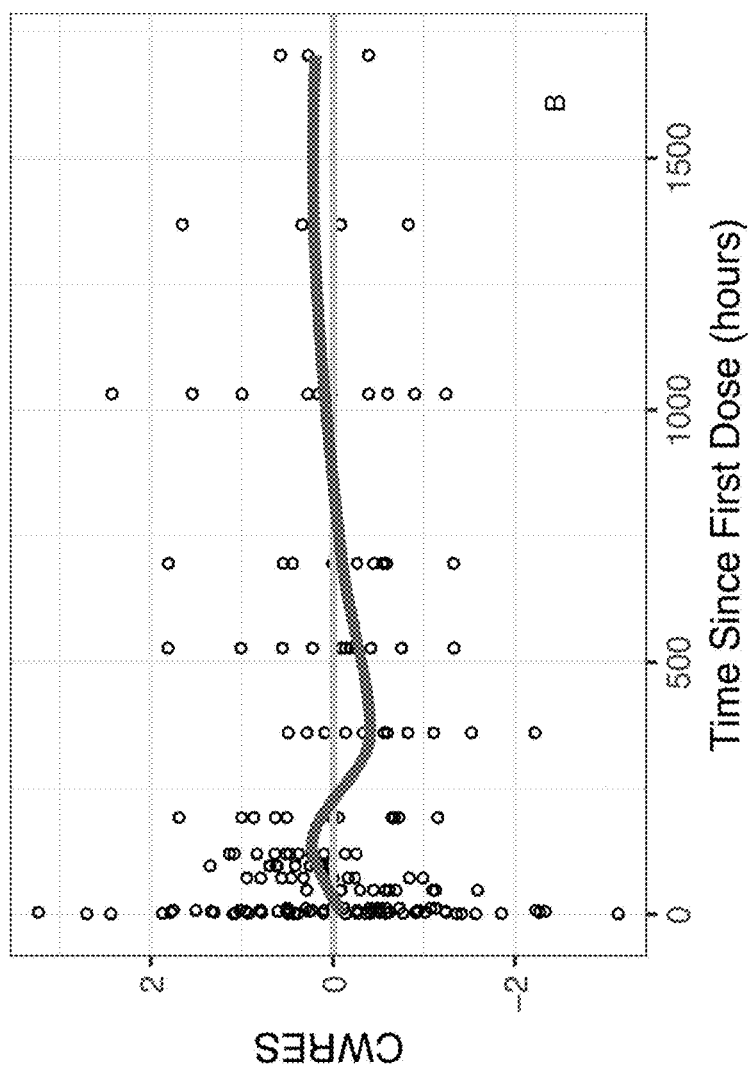

FIGS. 15A-B shows one versus two compartment model. FIG. 15A represents a one compartment disposition with first order. FIG. 15B represents a two-compartment disposition with a dual input. The distribution of conditional weighted residuals (CWRES) against time for the one compartment model (FIG. 15A) shows that there was a misspecification in the elimination phase. In contrast for the two-compartment model (FIG. 15B) shows the CWRES distribution over time is evenly distributed.

Figure 16:
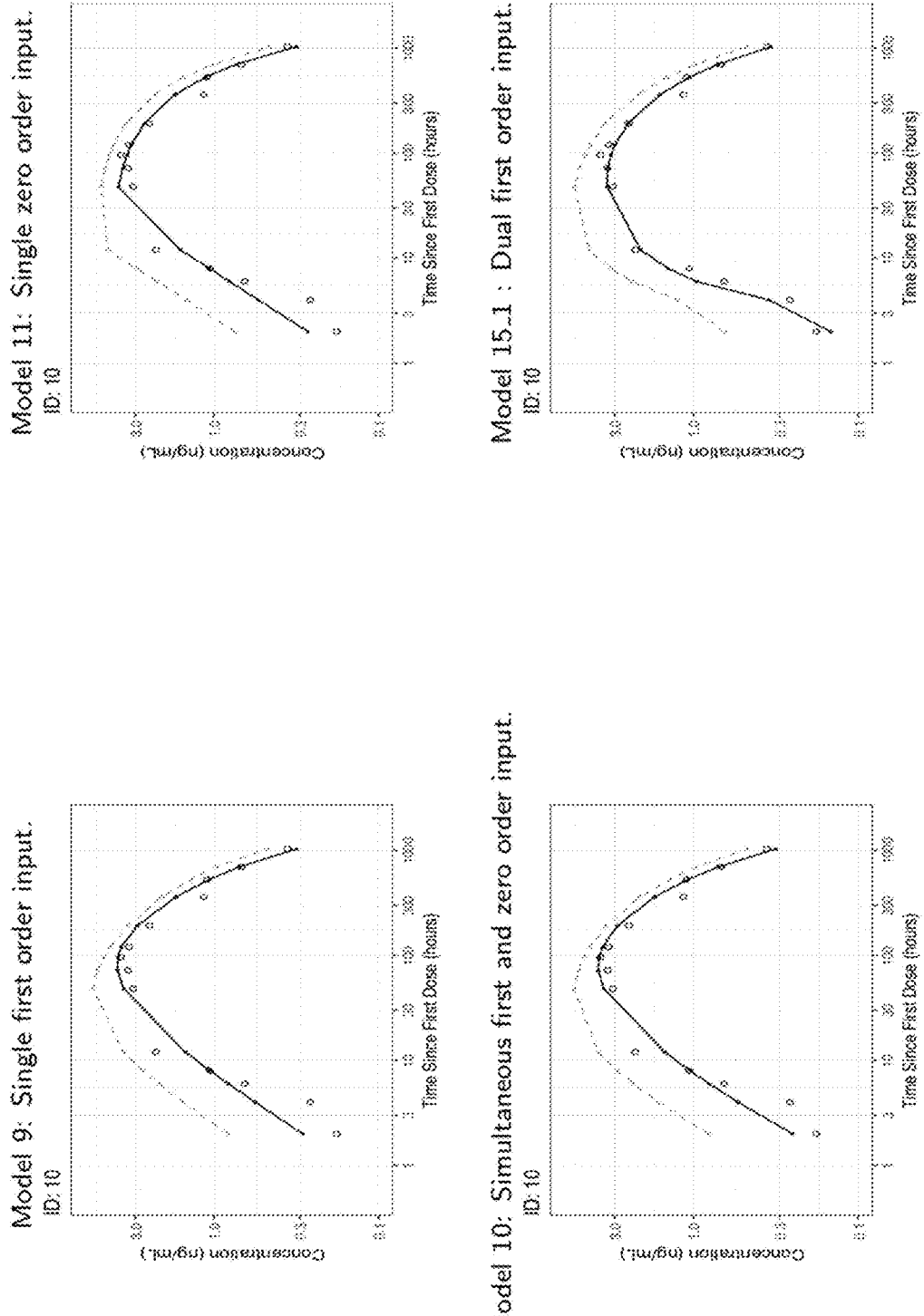
FIG. 16 displays predictions for patient 10 from several different input models used in Example 3.

FIG. 16 displays predictions for patient 10 from several different input models including: A single first order input (Model 9), a simultaneous first and zero order input (Model 10), a single zero order input (Model 11) and a dual first order input (Model 15 1). From the plots it was evident that models other than the dual first order input fails to properly capture the early phase of absorption.

Summary

The present analysis shows that anastrozole PK follows a two-compartment disposition profile. The absorption profile of anastrozole was well described by a dual input. The other input models failed to properly capture the absorption phase.

Example 4: Breast Tissue Elasticity

This example looks at the potential effect on breast tissue elasticity as assessed by shear wave ultrasound in the subjects that took part in the trial set forth in Example 1. Breast elasticity was measured by shear wave ultrasound measure on Days 1, 29, 57 and 85. Four measurements of glandular tissue elasticity and fatty tissue elasticity were taken for each breast. The calculated average of the eight measurements for each tissue type was the value used in summaries and analyses of breast elasticity. A summary of breast elasticity at each timepoint, and of the change from baseline is provided in table 8. Table 8 demonstrated breast tissue elasticity reduced progressively over time, with reductions from baseline of 28% for glandular tissues and 32% for fatty tissue.

TABLE 8

| | (n = 11) Breast Tissue Elasticity (kPa) | | | |
|---|---|---|---|---|
| | Measured Value Average (±Standard Deviation) | | Percent of Baseline Average (±Standard Deviation) | |
| Visit | Fatty Tissue | Glandular Tissue | Fatty Tissue | Glandular Tissue |
| Week 1, Day 1 | 9.98 (±3.38) | 16.49 (±4.79) | — | — |
| Week 5, Day 29 | 8.69 (±3.10) | 14.49 (±4.34) | 95.3% (±39.1) | 94.7% (±40.5) |
| Week 9, Day 57 | 7.17 (±2.63) | 12.43 (±5.02) | 86.3% (±53.0) | 86.4% (±49.5) |
| Week 13, Day 85 (EOS) | 5.74 (±1.68) | 10.65 (±2.74) | 67.8% (±45.7) | 71.8% (±35.4) |

Example 6: Expression of CD36

The breast tissue of women with autoimmune inflammatory mastitis (AIM) is high in aromatase and estradiol and thus Treg expression are heavily suppressed. Induction of CD36 in the breast tissue of women with AIM may result in tissue specific immunosuppression without systemic immunosuppression. This example shows that CD36 can be expressed in normal breast tissue by treatment with an androgenic agent in combination with an aromatase inhibitor as described herein.

Normal breast tissue was excised from 3 peri-menopausal women taken during surgery. The tissue samples were transported to the laboratory on ice, with a maximum time of one hour between excision and tissue processing. The breast tissue samples were washed in media (phenol red-free RPMI; SAFC biosciences, Kansas. USA), supplemented with 5 ml of 200 mM glutamine (SAFC biosciences, Kansas, USA), 5 ml of 100× anti-biotic/anti-mycotic (Sigma, St Louis, MO, USA), 10 µg/ml insulin (Sigma, St Louis, MO, USA), and 10 µg/ml hydrocortisone (Sigma, St Louis, MO, USA) to remove excess blood.

A representative piece of each tissue sample was immediately fixed in 4% formalin in phosphate-buffered saline (PBS) overnight at 4° C., followed by dehydration using an automatic tissue processor (Sakura Tissue-Tek VIP, USA) and paraffin wax embedding. A haematoxylin and eosin (H&E) stained section was used to assess tissue pathology. The remaining fresh tissue was cut into small (~3×3×1 mm) pieces, and placed as triplicates on 1 cm³ gelatin sponges (Spongostan; Johnson & Johnson, Skipton, UK) that were pre-soaked and then half submerged in treatment media containing 10% dextran-coated charcoal stripped fetal calf serum (DCC-FCS) (SAFC biosciences, Kansas, USA) in 24-well tissue culture plates (BD Biosciences, NJ, USA). The tissues samples were then cultured for 24 hours in a vehicle of 0.1% ethanol, 5 nM of testosterone and 25 ng/ml of anastrazole.

Western blotting whole cell lysates of and control adipose tissue were prepared by sonication at 48 C in lysis buffer (1% Triton X-100, 50 mM KCl, 25 mM HEPES, pH 7.8, 10 mg/ml of leupeptin, 20 mg/ml of aprotinin, 125 mM dithiothreitol and 1 mM phenylmethylsulfonyl fluoride) and analyzed on the same western blot. 50 mg samples of total protein were mixed with 50 ml of sodium dodecyl sulfate (SDS)-mercaptoethanol sample buffer and boiled for 10 min, then the proteins were separated on 7.5% SDS gels and transferred to a polyvinylidene fluoride membrane. The membrane was then blocked for 1 h at room temperature using 5% skimmed milk in phosphate-buffered saline (PBS) containing 0.5% Tween-20, immunoblotted with antibodies against human CD36 diluted in PBS and horseradish peroxidase-conjugated secondary antibodies (Jackson Immunoresearch) diluted in PBS, followed by detection with Chemiluminescence Reagent (Amersham Bioscience, Buckinghamshire, England). The band density was measured by densitometry, using Image Master VDS and Image Quant Analysis Software (Amersham Pharmacia Biotech, Hong Kong). The relative protein levels of CD36 and beta-actin in the original total protein lysate from the breast preparations were obtained. CD36 protein expression was normalized to beta-actin protein expression. Immunizing host produced the antibodies with a synthetic peptide derived from the sequence of human CD36, purified by peptide affinity chromatography and confirmed using control peptides. The results of the western blot analysis CD36 protein in 3 explant samples are shown in FIG. 17 at baseline and after 24 hours of cultivation. Cell lysates were immunoblotted with antibodies to CD36. The experiment was performed twice with similar results. Data are expressed relative to actin. A 2-tailed student t-test revealed significance at p=0.00757. The results are set forth in Table 9 below.

TABLE 9

Western blot band density measurements

| Patient number | Pre-treatment | Post-treatment |
| --- | --- | --- |
| 1 | 0.3235 | 0.9845 |
| 2 | 0.2135 | 1.0156 |
| 3 | 0.1478 | 0.4875 |
| Mean | 0.2283 | 0.8292 |
| SC | 0.0888 | 0.29634 |

Increasing CD36 increases conversion of fibroblasts to adipocytes (fat). The adipocytes (fat) is a semi-fluid and therefore has greater elasticity. The present example shows a significant increase in CD36 in normal breast tissue following treatment with the androgenic agent testosterone in combination with the aromatase inhibitor anastrozole. Increased CD36 expression is associated with a reduction in breast stiffness. As described herein, certain embodiments of the present disclosure are directed to use of a combination therapy of an androgenic agent and an aromatase inhibitor to increase CD36 and a reduction in breast stiffness.

The above demonstrates in normal breast tissue that the combination of testosterone and an aromatase inhibitor is highly effective in the inducing CD36 as demonstrated in the Western protein blot below which shows CD36 is heavily induced by the treatment of normal breast tissue harvested at surgery and grown in explant.

Example 7: Idiopathic Inflammatory Macromastia

Four patients with idiopathic inflammatory mastitis associated with mild to moderate macromastia were treated in accordance with the present disclosure, as discussed below.
Patient 1: 42.03416971
Presentation
A 38 year old chiropractor with rapid breast enlargement—"doubled in size", peri-areolar inflammation and with severe constant pain over 2 months unresponsive to over the counter analgesia and NSAIDs which impacted on the patient's ability to work.
Bra Cup Size Pre-Morbid
The patient had a bra cup size of 32A, and was unable to wear a bra post-morbid.
Past Medical History
Included the patient having severe pre-menstrual dysphoria partly controlled by oral contraceptive pill, had ceased taking oral contraceptive pill 2 years prior to presentation, regular 28 day cycle with 2 pregnancies and 2 live births. Severe post-partum arthritis—undiagnosed—settled after 1 year, no abnormal blood parameters noted.
VAS Pain Scale Pre-Morbid: 95 mm
Treatment
Subcutaneous implant pellet of 80 mg testosterone and 4 mg anastrozole as described in Example 1 for 3 months, repeated for two further 3 month periods
Results
  i. VAS pain scale at 4 weeks 10 mm
  ii. Inflammation undetectable at 4 weeks
  iii. Fibro-glandular tissue reduction 71%
  iv. Breast Volume reduction 58% back to pre-morbid size
  v. Complete reversal of extreme background parenchymal enhancement on MRI which persisted over the subsequent 3 years after therapy ceased
  vi. No SAEs
  vii. No change in BMI Mammograms of a breast of the patient before and after treatment are shown in FIG. 19A, and MRI images before treatment for the subsequent 3 years following treatment are shown in FIG. 19C. Breast volume and density measurements are shown in FIG. 19B.

Patient 2: 42.09761311

Presentation

A 42 year old nurse rapid breast enlargement-"very hard", diffuse inflammation and severe constant pain over 4 months which was unresponsive to over the counter analgesia and NSAIDs, impacting work and home life-could not ride her horse. Left breasts was much larger than the right breast.

Bra Cup Size: Pre-Morbid

The patient had a bra cup size of 36C and was unable to wear bra post morbid-she wore a sports bra all day and to bed.

Past Medical History

Regular 28 day cycle, 2 pregnancies and 2 live births with severe pre-eclampsia, post partum depression including hospitalization, no abnormalities in blood parameters noted.

VAS Pain Scale Pre-Morbid: 100 mm

Treatment

Subcutaneous implant pellet of 80 mg Testosterone and 4 mg anastrozole for 3 months, repeated for two further 3 month period.

Results
  i. VAS pain scale at 4 weeks 15 mm
  ii. Inflammation undetectable at 4 weeks
  iii. Fibro-glandular tissue reduction 41%
  iv. Breast Volume reduction 10% back to pre-morbid size
  v. NoSAEs
  vi. No change in BMI
  vii. No mammoplasty Mammograms of a breast of the patient before and after treatment are shown in FIG. 20A. Breast volume and density measurements are shown in FIG. 20B.

Patient 3: 42.09761311

Presentation

A 37 year old lawyer with rapid breast enlargement—inflammation especially around the nipples and severe constant pain over 2 months which was unresponsive to over the counter analgesia and NSAIDs-impacting work and home life.

Bra Cup Size

Pre-morbid 34C unable to wear bra post morbid-wore sports bra all day and to bed.

Past Medical History

Regular 28 day cycles with no pregnancies, moderate endometriosis, no abnormalities in blood parameters noted.

VAS Pain Scale Pre-Morbid: 100 mm

Treatment

Subcutaneous implant pellet of 80 mg Testosterone and 4 mg anastrozole as described in Example 1 for 3 months, repeated for two further 3 month period.

Results
  i. VAS pain scale at 4 weeks 0 mm
  ii. Inflammation undetectable at 4 weeks
  iii. Fibro-glandular tissue reduction 52%
  iv. Breast Volume reduction 32% back to pre-morbid size
  v. No SAEs
  vi. No change in BMI
  vii. No mammoplasty Mammograms of a breast of the patient before and after treatment are shown in FIG. 21A. Breast volume and density measurements are shown in FIG. 21B.

Patient 4: 42.83593371

Presentation

A 41 year old police officer with rapid breast enlargement-"very hard", diffuse inflammation and severe constant pain over 1 month which was unresponsive to over the counter analgesia and NSAIDs impacting on the patients work and home life-could not wear Kevlar protective kit.

Bra Cup Size

Pre-morbid 36B unable to wear bra post morbid-wore sports bra all day and to bed.

Past Medical History

Regular 28 day cycles with no pregnancies, severe endometriosis with multiple surgeries, no abnormalities in blood parameters noted.

VAS Pain Scale Pre-Morbid: 100 mm

Treatment

Subcutaneous implant pellet of 80 mg testosterone and 4 mg anastrozole as described in Example 1 for 3 months, repeated for two further 3 month period, mammoplasty then 2 further post operative treatments for 3 months as above.

Results
  i. VAS pain scale at 4 weeks 0 mm
  ii. Inflammation undetectable at 4 weeks
  iii. Fibro-glandular tissue reduction 36%
  iv. Breast Volume reduction 23% back to pre-morbid size
  v. Complete reversal of MRI extreme background parenchymal enhancement
  vi. No SAEs
  vii. No change in BMI MRI images of a breast of the patient before and after treatment are shown in FIG. 22A, and mammographic images before and after treatment are shown in FIG. 22B. Breast volume and density measurements are shown in FIG. 22C.

Example 8: Treatment of Autoimmune Inflammatory Mastitis

Patient: 42.04033771

Presentation

A 24 year old physical therapist with rapid breast enlargement-"extremely painful", diffuse inflammation and severe constant pain over 4 months—could not work and unresponsive to:
  i. over the counter analgesia and NSAIDs
  ii. OCP
  iii. Oral progesterone
  iv. Danazol
  v. LhRh agonist Bra Cup Size Pre-morbid 36B enlarged to 36EE.

Past Medical History

Obstetric/Gynological history included an irregular 28 day cycle—amenorrhoeic due to Zoladex, with no pregnancies. No abnormalities in blood parameters were noted.

VAS Pain Scale Pre-Morbid: 100 mm

Treatment

Figure 23:
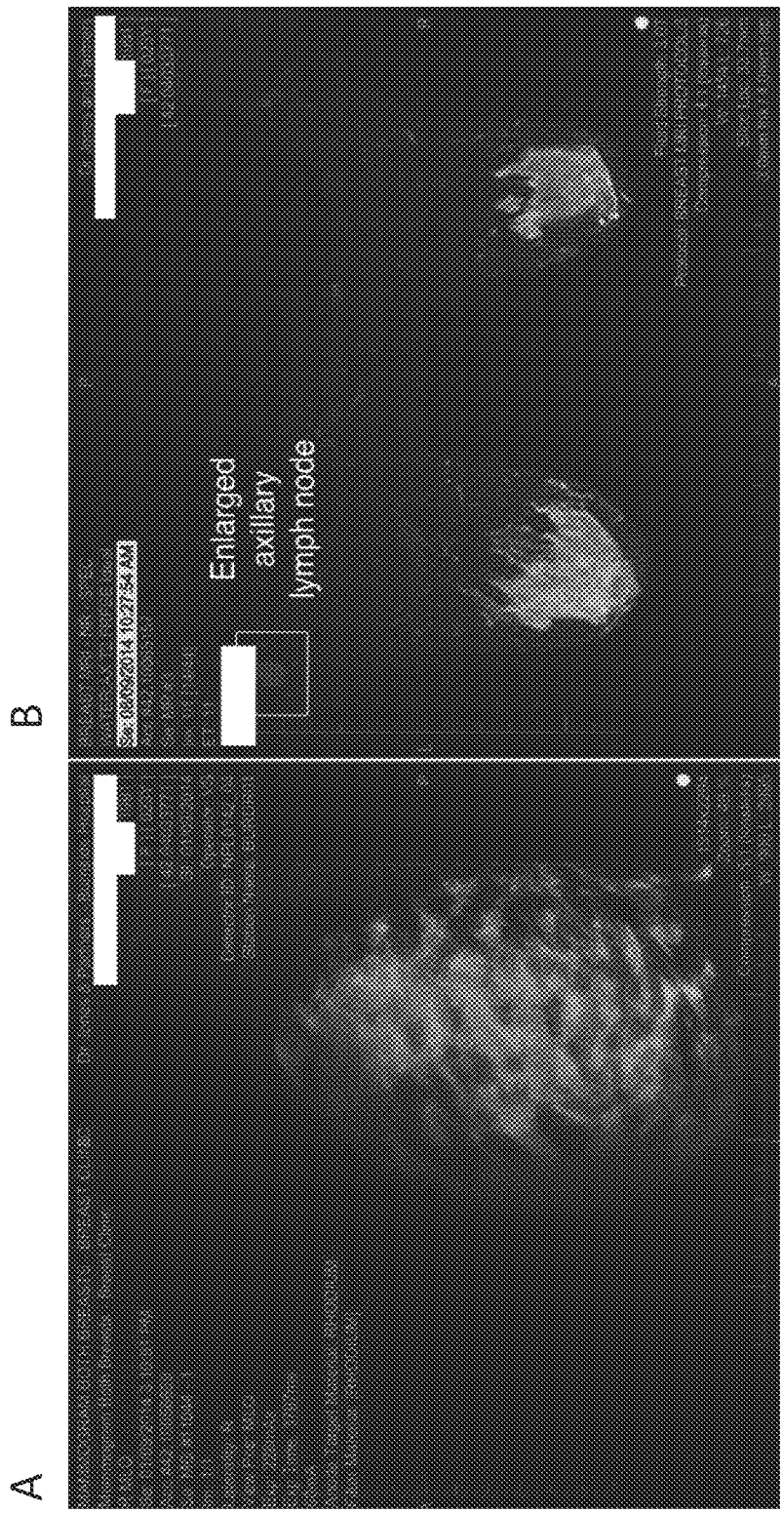
FIG. 23A shows extreme breast swelling in another patient demonstrated by mammography before treatment treatment in accordance with the present disclosure.
FIG. 23B shows a magnetic resonance image (MRI) of intense breast metabolic activity with little fat demonstrated as shown by extreme background parenchymal enhancement in the breast of the patient of FIG. 23A.

Subcutaneous implant pellet of 100 mg Testosterone and 3 mg anastrozole for 3 months, reduction mammoplasty was conducted then 2 further post operative treatments for 3 months as above Results
  i. VAS pain scale at 4 weeks 50 mm
  ii. Inflammation significantly down at 4 weeks
  iii. Mammogram intense density and MRI extreme background parenchymal enhancement reversed
  iv. No SAEs
  v. No change in BMI
  vi. Subsequently diagnosed with myasthenia gravis A mammographic image of a breast of the patient before treatment is shown in FIG. 23A. An MRI image after the treatment is shown in FIG. 23B.

Example 9: Treatment of Plasma Cell Mastitis

Plasma cell mastitis is an autoimmune inflammatory destructive process of the retro-areolar milk ducts which results in multiple fistulae and inevitably results in disfiguring surgery and a high risk of recurrence. There is no known treatment for this condition apart from surgery which has significant limitations. Plasma cell mastitis is exemplified by the invasion of the milk duct system with inflammatory cells that secrete pro-inflammatory cytokines. Recently it has been demonstrated that the IL-6 inflammatory pathways critical in this inflammatory process and has been targeted as a potential mechanism to be targeted for treatment of plasma cell mastitis (Liu, 2020). It has been demonstrated that the female breast has cells which are extremely responsive (a reduction of 53%) to treatment with testosterone in reducing IL-6 levels (Guhl, 2012).

A 43-year-old otherwise fit and well woman presented with multiple fistulae around the right nipple area of the complex which had not responded to antibiotic therapy in the first instance then high dose corticosteroids and a total duct excision as a surgical procedure only resulted in a short-term remission. There was significant inflammation around the right nipple areolar complex with four fistulae at the 4 o'clock position on the edge of the areolar. There was significant pain which measured 8 on a 0 to 10 cm visual analogue pain scale. She was commenced on T+AI therapy and received an 80 mg testosterone 4 mg anastrozole subcutaneous implant. Within three weeks her visual analogue pain scale dropped back to 3 and there was some resolution of the peri-areolar redness. After 11 months with three implants of the same strength being inserted, there was complete resolution of the fistula formation and no associated pain. A follow-up 12 months later revealed no evidence of disease recurrence.

Example 10: Granulomatous Mastitis

Granulomatous mastitis is also known as granulomatous lobular mastitis due to the inflammation occurring around the breast lobules. It is a manifestation of autoimmune inflammatory mastitis in the breast tissue which results in granuloma formation, inflammation and fistula formation. There is no known cure for this condition and women frequently undergo multiple operations and/or receive immunosuppressive treatment.

A 32-year-old woman presented for a second opinion following six months of treatment for histologically proven granulomatous mastitis. She had been given antibiotics, corticosteroids, methotrexate and had undergone surgery to remove a fistula. All of these had failed as demonstrated by an MRI taken on 23 Jul. 2017 which demonstrated multiple areas of granuloma formation with a large reactive axilla lymph node.

Between the first MRI and a second MRI taken on 23 May 2018 she had three testosterone 80 mg anastrozole 4 mg implants as described in Example 1 inserted. The inflammation reduced rapidly and the one remaining fistula healed up over a three month period. The tenderness and breast discomfort persisted for five months and then slowly subsided. Clinical examination on 23 May 2018 revealed only minor scarring in the breast from previous surgery but no other abnormalities. She remained disease-free when reviewed in February 2020.

Figure 24:
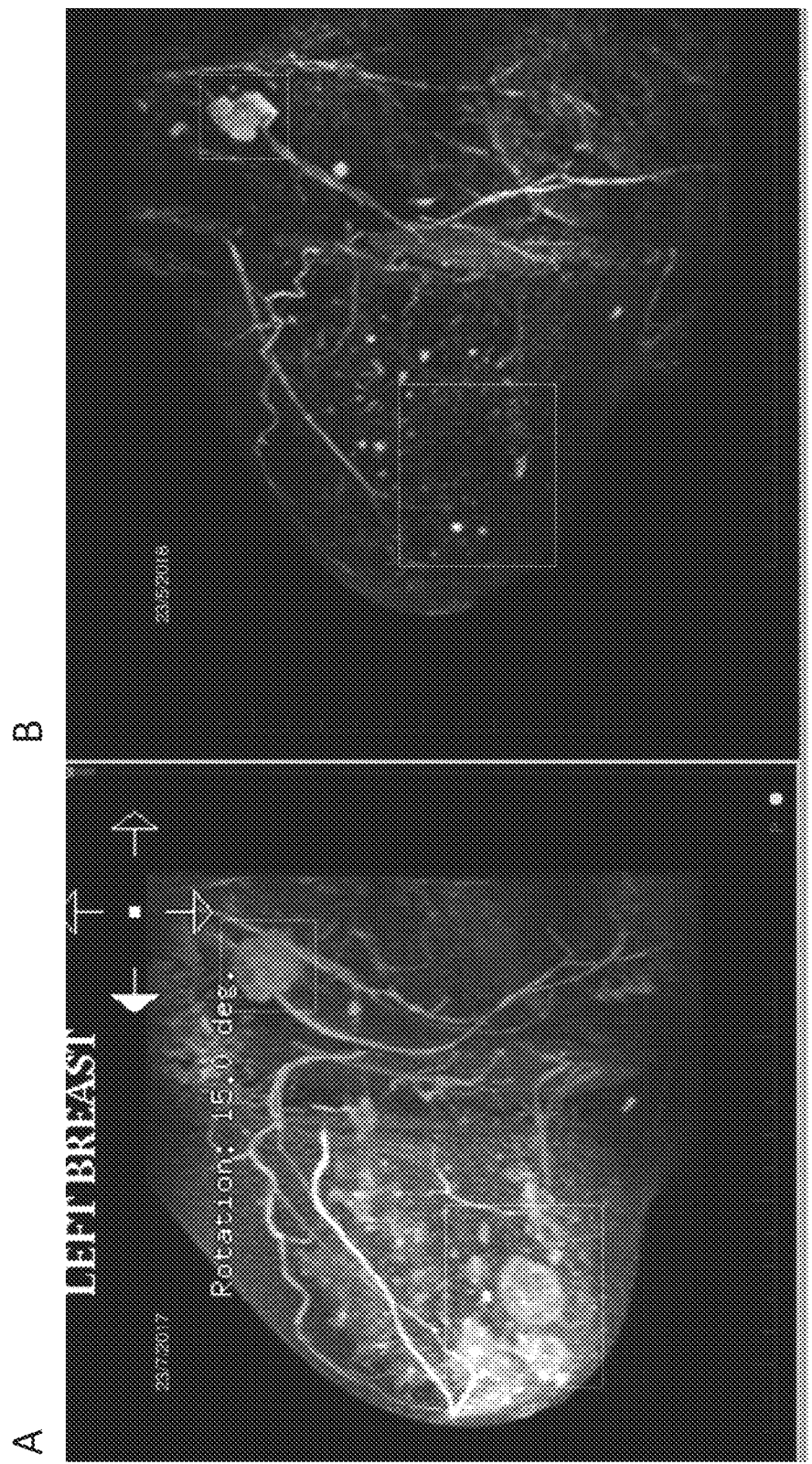
FIG. 24A shows a magnetic resonance image (MRI) of another patient with granuloma formation in the retroareolar space with an enlarged reactive axillary lymph node.
FIG. 24B is an MRI image of the breast of the patient of FIG. 24A showing resolution of the granulomata and reduction in size of the axillary lymph node after treatment in accordance with the present disclosure.

A mammographic image of a breast of the patient before treatment is shown in FIG. 24A. An MRI image obtained after treatment is shown in FIG. 23B.

Other Exemplary Non-Limiting Embodiments

Further advantages of the claimed subject matter will become apparent from the following examples describing certain embodiments of the claimed subject matter.

A Examples

1A. A pharmaceutical formulation comprising:
  an effective amount of an androgen, an effective amount of an aromatase inhibitor and a binding agent;
  the formulation upon administration to a subject provides a sustained release multi-phasic concentration pattern in the blood of the subject over time as measured by serum concentration for the androgen and plasma concentration for the aromatase inhibitor; and
  the sustained release multi-phasic concentration pattern in the serum or plasma of the subject comprising:
    a first time period in which the androgen, has a first peak in concentration (Tmax) in the serum and the aromatase inhibit is increasing in concentration in the plasma but is below its Tmax concentration in the plasma; and
    a second time period in which the androgen, has initially a decreasing serum level concentration and then an increasing serum level concentration and the aromatase inhibitor has its Tmax concentration in the plasma.

2A. A pharmaceutical formulation comprising:
  an effective amount of an androgen, an effective amount of an aromatase inhibitor and a binding agent;
  the pharmaceutical formulation is compressed into a pellet;
  the pellet upon subcutaneous administration to a subject provides a sustained release multi-phasic concentration pattern in the blood of the subject over time as measured by serum concentration for the androgen and plasma concentration for the aromatase inhibitor; and
  the sustained release multi-phasic concentration pattern in the serum or plasma of the subject comprising:
    a first time period in which the androgen, has a first peak in concentration (Tmax) in the serum and the aromatase inhibitor is increasing in concentration in the plasma but is below its Tmax concentration in the plasma; and
    a second time period in which the androgen, has initially a decreasing serum level concentration and then an increasing serum level concentration and the aromatase inhibitor has its Tmax concentration in the plasma.

3A. A pharmaceutical formulation comprising:
  an effective amount of an androgen, an effective amount of an aromatase inhibitor and a binding agent;
  the formulation upon administration to a subject provides a sustained release multi-phasic concentration pattern in the blood of the subject over time as measured by serum concentration for the androgen and plasma concentration for the aromatase inhibitor; and the sustained release multi-phasic concentration pattern in the serum or plasma of the subject comprising:
  a first time period in which the androgen, has a first peak in concentration (Tmax) in the serum and the aromatase inhibitor is increasing in concentration in the plasma but is below its Tmax concentration in the plasma;
  a second time period in which the androgen, has initially a decreasing serum level concentration and then an increasing serum level concentration and the aromatase inhibitor has its Tmax concentration in the plasma;
  a third time period in which the androgen, has a second peak concentration in the serum that is less than the Tmax and the aromatase inhibitor is gradually decreasing in concentration in the plasma and in the third time period falls below the concentration of the androgen; and
  a fourth time period in which the androgen has a gradually decreasing serum level concentration and the aromatase inhibitor has a gradually decreasing concentration in the plasma and both decreasing levels approximately parallel each other.

4A. A pharmaceutical formulation comprising:
  an effective amount of an androgen, an effective amount of an aromatase inhibitor and a binding agent:
the pharmaceutical formulation is compressed into a pellet;
  the pellet upon subcutaneous administration to a subject provides a sustained release multi-phasic concentration pattern in the blood of the subject over time as measured by serum concentration for the androgen and plasma concentration for the aromatase inhibitor; and
  the sustained release multi-phasic concentration pattern in the serum or plasma of the subject comprising:
    a first time period in which the androgen, has a first peak in concentration (Tmax) in the serum and the aromatase inhibitor is increasing in concentration in the plasma but is below its Tmax concentration in the plasma;
    a second time period in which the androgen, has initially a decreasing serum level concentration and then an increasing serum level concentration and the aromatase inhibitor has its Tmax concentration in the plasma;
    a third time period in which the androgen, has a second peak concentration in the serum that is less than the Tmax and the aromatase inhibitor is gradually decreasing in concentration in the plasma and in the third time period falls below the concentration of the androgen; and
    a fourth time period in which the androgen has a gradually decreasing serum level concentration and the aromatase inhibitor has a gradually decreasing concentration in the plasma and both decreasing levels approximately parallel each other.

5A. A pharmaceutical formulation comprising:
  60 mg to 120 mg of a testosterone, or an ester thereof, 4 mg to 6 mg of an aromatase inhibitor and stearic acid;
the pharmaceutical formulation is compressed into a pellet that has a diameter of between 4.25 mm to 4.75 mm and a length of between 4 mm to 7 mm;
  the pellet upon subcutaneous administration to a subject provides a sustained release multi-phasic concentration pattern in the blood of the subject over time as measured by serum concentration for the testosterone or an ester thereof, and plasma concentration for the aromatase inhibitor; and
  the sustained release multi-phasic concentration pattern comprising:
    a first time period in which the testosterone or an ester thereof, has a first peak in concentration (Tmax) in the serum and the aromatase inhibitor is increasing in concentration in the plasma but is below its Tmax concentration in the plasma; and
    a second time period in which the testosterone or an ester thereof, has initially a decreasing serum level concentration and then an increasing serum level concentration and the aromatase inhibitor has its Tmax concentration in the plasma.

6A. A pharmaceutical formulation comprising:
  60 mg to 120 mg of a testosterone, or an ester thereof, 4 mg to 6 mg of an aromatase inhibitor and stearic acid;
the pharmaceutical formulation is compressed into a pellet that has a diameter of between 4.25 mm to 4.75 mm and a length of between 4 mm to 7 mm;
  the pellet upon subcutaneous administration to a subject provides a sustained release multi-phasic concentration pattern in the blood of the subject over time as measured by serum concentration for the testosterone or an ester thereof, and plasma concentration for the aromatase inhibitor; and
  the sustained release multi-phasic concentration pattern comprising:
    a first time period in which the testosterone or an ester thereof, has a first peak in concentration (Tmax) in the serum and the aromatase inhibitor is increasing in concentration in the plasma but is below its Tmax concentration in the plasma;
    a second time period in which the testosterone or an ester thereof, has initially a decreasing serum level concentration and then an increasing serum level concentration and the aromatase inhibitor has its Tmax concentration in the plasma;
    a third time period in which the testosterone or an ester thereof, has a second peak concentration in the serum that is less than the Tmax and the aromatase inhibitor is gradually decreasing in concentration in the plasma and in the third time period falls below the concentration of the testosterone or an ester thereof; and
    a fourth time period in which the testosterone or an ester thereof, has a gradually decreasing serum level concentration and the aromatase inhibitor has a gradually decreasing concentration in the plasma and both decreasing levels approximately parallel each other.

7A. The pharmaceutical formulation of examples 1A, 2A, or 5A, wherein the sustained release multi-phasic concentration pattern further comprises:

a third time period in which the testosterone or an ester thereof, has a second peak concentration in the serum that is less than the Tmax and the aromatase inhibitor is gradually decreasing in concentration in the plasma and in the third time period falls below the concentration of the testosterone or an ester thereof; and a fourth time period in which the testosterone or an ester thereof, has a gradually decreasing serum level concentration and the aromatase inhibitor has a gradually decreasing concentration in the plasma and both decreasing levels approximately parallel each other.

8A. The pharmaceutical formulation of one or more of examples 1A to 7A, wherein during the first time period the aromatase inhibitor exhibits first order release.

9A. The pharmaceutical formulation of one or more of examples 1A to 8A, wherein during the first time period the aromatase inhibitor does not exhibit zero order release.

10A. The pharmaceutical formulation of one or more of examples 1A to 9A, wherein during the second time period the aromatase inhibitor does not exhibit zero order release.

11A. The pharmaceutical formulation of one or more of examples 1A to 10A, wherein during the second time period the testosterone or an ester thereof, does not exhibit zero order release.

12A. The pharmaceutical formulation of one or more of examples 1A to 11A, wherein during the third time period the aromatase inhibitor does not exhibit zero order release.

13A. The pharmaceutical formulation of one or more of examples 1A to 12A, wherein during the third time period the testosterone or an ester thereof, does not exhibit zero order release.

14A. The pharmaceutical formulation of one or more of examples 1A to 13A, wherein during the third time period the aromatase inhibitor exhibit first order release.

15A. The pharmaceutical formulation of one or more of examples 1A to 14A, wherein during the third time period the testosterone or an ester thereof, exhibit first order release.

16A. The pharmaceutical formulation of one or more of examples 1A to 15A, wherein during the fourth time period the aromatase inhibitor does not exhibit zero order release.

17A. The pharmaceutical formulation of one or more of examples 1A to 16A, wherein during the fourth time period the testosterone or an ester thereof, does not exhibit zero order release.

18A. The pharmaceutical formulation of one or more of examples 1A to 17A, wherein during the fourth time period the aromatase inhibitor exhibit first order release.

19A. The pharmaceutical formulation of one or more of examples 1A to 18A, wherein during the fourth time period the testosterone or an ester thereof, exhibit first order release.

20A. The pharmaceutical formulation of one or more of examples 1A to 19A, wherein the first time period ends right after the androgen, has a first peak in concentration (Tmax) in the serum.

21A. The pharmaceutical formulation of one or more of examples 1A to 20A, wherein the first time period ends between 5 hours to 14 hours.

22A. The pharmaceutical formulation of one or more of examples 1A to 21A, wherein the first time period ends between 5.5 hours to 13 hours.

23A. The pharmaceutical formulation of one or more of examples 1A to 22A, wherein the second time period ends right after the aromatase inhibitor has its Tmax.

24A. The pharmaceutical formulation of one or more of examples 1A to 23A, wherein the second time period ends between 23 hours to 80 hours.

25A. The pharmaceutical formulation of one or more of examples 1A to 24A, wherein the pharmaceutical formulation is an implant.

26A. The pharmaceutical formulation of one or more of examples 1A to 25A, wherein the the implant is a compressed pellet.

27A. The pharmaceutical formulation of one or more of examples 1A to 24A, wherein the pharmaceutical formulation is transdermal patch.

28A. The pharmaceutical formulation of one or more of examples 1A to 25A, wherein the implant is subcutaneously administered to a subject.

28A. The pharmaceutical formulation of one or more of examples 1A to 26A, wherein the compressed pellet is subcutaneously administered to a subject.

B Examples

1B. A pharmaceutical formulation comprising:
approximately 80 mg of a testosterone or an ester thereof, approximately 4 mg anastrozole and approximately 2 mg of a stearic acid;

the pharmaceutical formulation is compressed into a pellet that has a diameter of between 4.4 mm to 4.6 mm and a length of between 4 mm to 7 mm;

the pellet upon subcutaneous administration to a subject provides a sustained release multi-phasic concentration pattern in the blood of the subject over time as measured by serum concentration for the testosterone or an ester thereof, and plasma concentration for the anastrozole;

the sustained release multi-phasic concentration pattern comprising:
a first time period of in which the testosterone or an ester thereof, has a first peak in concentration (Tmax) in the serum and the anastrozole is increasing in concentration in the plasma but is below its Tmax concentration in the plasma;

a second time period in which the testosterone or an ester thereof, has initially a decreasing serum level concentration and then an increasing serum level concentration and the anastrozole has its Tmax concentration in the plasma;

a third time period in which the testosterone or an ester thereof, has a second peak concentration in the serum that is less than the Tmax and the anastrozole is gradually decreasing in concentration in the plasma and in the third time period falls below the concentration of the testosterone, or an ester thereof; and a fourth time period in which the testosterone or an ester thereof, has a gradually decreasing serum level concentration and the anastrozole has a gradually decreasing concentration in the plasma and both decreasing levels approximately parallel each other.

While certain embodiments have been shown and described herein, it will be obvious to those skilled in the art that such embodiments are provided by way of example only. It is intended that the following claims define the scope of the inventions and that methods and structures within the scope of these claims and their equivalents be covered thereby.

In the foregoing description of certain embodiments, specific terminology has been resorted to for the sake of clarity. However, the disclosure is not intended to be limited to the specific terms so selected, and it is to be understood that each specific term includes other technical equivalents which operate in a similar manner to accomplish a similar technical purpose. Terms such as "left" and right", "front" and "rear", "above" and "below" and the like are used as words of convenience to provide reference points and are not to be construed as limiting terms.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

In addition, the foregoing describes only some embodiments of the inventions, and alterations, modifications, additions and/or changes may be made thereto without departing from the scope and spirit of the disclosed embodiments, the embodiments being illustrative and not restrictive.

It is to be understood that the inventions are not to be limited to the disclosed embodiments, but on the contrary, is intended to cover various modifications and equivalent arrangements included within the spirit and scope of the inventions. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

The invention claimed is:

1. A pharmaceutical formulation comprising:
an effective amount of an androgenic agent that is testosterone or pharmaceutically acceptable salt or ester thereof, an effective amount of an aromatase inhibitor that is anastrozole, and a binding agent;
the pharmaceutical formulation is compressed into a pellet;
the pellet upon subcutaneous administration to a subject provides a sustained release multi-phasic concentration pattern in the blood of the subject over time as measured by serum concentration for the androgenic agent and plasma concentration for the aromatase inhibitor; and
the sustained release multi-phasic concentration pattern in the serum or plasma of the subject comprising:
a first time period in which the androgenic agent has a first peak in concentration (Tmax) in the serum and the aromatase inhibitor is increasing in concentration in the plasma but is below its Tmax concentration in the plasma; and
a second time period in which the androgenic agent has initially a decreasing serum level concentration and then an increasing serum level concentration and the aromatase inhibitor has its Tmax concentration in the plasma.

2. The pharmaceutical formulation of claim 1 wherein said sustained release multi-phasic concentration pattern in the serum or plasma of the subject further comprises:
a third time period in which the androgenic agent has a second peak concentration in the serum that is less than the Tmax and the aromatase inhibitor is gradually decreasing in concentration in the plasma and in the third time period falls below the concentration of the androgen; and
a fourth time period in which the androgenic agent has a gradually decreasing serum level concentration and the aromatase inhibitor has a gradually decreasing concentration in the plasma and both decreasing levels approximately parallel each other.

3. The pharmaceutical formulation of claim 1, wherein during the first time period the aromatase inhibitor exhibits first order release.

4. The pharmaceutical formulation of claim 1, wherein during the first time period the aromatase inhibitor does not exhibit zero order release.

5. The pharmaceutical formulation of claim 1, wherein during the second time period the aromatase inhibitor does not exhibit zero order release.

6. The pharmaceutical formulation of claim 1, wherein during the second time period the androgenic agent does not exhibit zero order release.

7. The pharmaceutical formulation of claim 2, wherein during the third time period the aromatase inhibitor does not exhibit zero order release.

8. The pharmaceutical formulation of claim 2, wherein during the third time period the androgenic agent does not exhibit zero order release.

9. The pharmaceutical formulation of claim 1, wherein the sustained release multi-phasic concentration pattern further comprises:
a third time period in which the androgenic agent has a second peak concentration in the serum that is less than the Tmax and the aromatase inhibitor is gradually decreasing in concentration in the plasma and in the third time period falls below the concentration of the testosterone or an ester thereof; and
a fourth time period in which the androgenic agent has a gradually decreasing serum level concentration and the aromatase inhibitor has a gradually decreasing concentration in the plasma and both decreasing levels approximately parallel each other.

10. The pharmaceutical formulation of claim 9, wherein during the third time period the aromatase inhibitor exhibits first order release.

11. The pharmaceutical formulation of claim 9, wherein during the third time period the androgenic agent exhibits first order release.

12. The pharmaceutical formulation of claim 9, wherein during the fourth time period the aromatase inhibitor does not exhibit zero order release.

13. The pharmaceutical formulation of claim 9, wherein during the fourth time period the androgenic agent does not exhibit zero order release.

14. The pharmaceutical formulation of claim 9, wherein during the fourth time period the aromatase inhibitor exhibits first order release.

15. The pharmaceutical formulation of claim 9, wherein during the fourth time period the androgenic agent exhibits first order release.

16. The pharmaceutical formulation of claim 1, wherein the first time period ends right after the androgenic agent has a first peak in concentration (Tmax) in the serum.

17. The pharmaceutical formulation of claim 1, wherein the first time period ends between 5 hours to 14 hours.

18. The pharmaceutical formulation of claim 1, wherein the first time period ends between 5.5 hours to 13 hours.

19. The pharmaceutical formulation of claim 1, wherein the second time period ends right after the aromatase inhibitor has its Tmax.

20. The pharmaceutical formulation of claim 1, wherein the second time period ends between 23 hours to 80 hours.

21. The pharmaceutical formulation of claim 1 being for subcutaneous delivery of the androgenic agent and the aromatase inhibitor.

22. A pharmaceutical formulation comprising:
60 mg to 120 mg of a testosterone, or an ester thereof, 2 mg to 6 mg of an aromatase inhibitor which is anastrozole and more preferably 4 mg to 6 mg of an aromatase inhibitor which is anastrozole, and stearic acid;
the pharmaceutical formulation is compressed into a pellet that has a diameter of between 4.25 mm to 4.75 mm and a length of between 4 mm to 7 mm;
the pellet upon subcutaneous administration to a subject provides a sustained release multi-phasic concentration pattern in the blood of the subject over time as measured by serum concentration for the testosterone or an ester thereof, and plasma concentration for the aromatase inhibitor; and
the sustained release multi-phasic concentration pattern comprising:
a first time period in which the testosterone or an ester thereof, has a first peak in concentration (Tmax) in the serum and the aromatase inhibitor is increasing in concentration in the plasma but is below its Tmax concentration in the plasma; and
a second time period in which the testosterone or an ester thereof, has initially a decreasing serum level concentration and then an increasing serum level concentration and the aromatase inhibitor has its Tmax concentration in the plasma.

23. A pharmaceutical formulation comprising:
60 mg to 120 mg of a testosterone, or an ester thereof, 2 mg to 6 mg of an aromatase inhibitor which is anastrozole and more preferably 4 mg to 6 mg of an aromatase inhibitor which is anastrozole, and stearic acid;
the pharmaceutical formulation is compressed into a pellet that has a diameter of between 4.25 mm to 4.75 mm and a length of between 4 mm to 7 mm;
the pellet upon subcutaneous administration to a subject provides a sustained release multi-phasic concentration pattern in the blood of the subject over time as measured by serum concentration for the testosterone or an ester thereof, and plasma concentration for the aromatase inhibitor; and
the sustained release multi-phasic concentration pattern comprising:
a first time period in which the testosterone or an ester thereof, has a first peak in concentration (Tmax) in the serum and the aromatase inhibitor is increasing in concentration in the plasma but is below its Tmax concentration in the plasma;
a second time period in which the testosterone or an ester thereof, has initially a decreasing serum level concentration and then an increasing serum level concentration and the aromatase inhibitor has its Tmax concentration in the plasma;
a third time period in which the testosterone or an ester thereof, has a second peak concentration in the serum that is less than the Tmax and the aromatase inhibitor is gradually decreasing in concentration in the plasma and in the third time period falls below the concentration of the testosterone or an ester thereof; and
a fourth time period in which the testosterone or an ester thereof, has a gradually decreasing serum level concentration and the aromatase inhibitor has a gradually decreasing concentration in the plasma and both decreasing levels approximately parallel each other.

* * * * *